United States Patent
Saeki et al.

(12)

(10) Patent No.: US 12,254,009 B2
(45) Date of Patent: Mar. 18, 2025

(54) SEARCH APPARATUS, SEARCH METHOD, AND STORAGE MEDIUM

(71) Applicant: INFORMEX, INC., Tokyo (JP)

(72) Inventors: Joji Saeki, Tokyo (JP); Takuya Saeki, Tokyo (JP); Shinya Saeki, Tokyo (JP)

(73) Assignee: INFORMEX, INC., Tokyo (JP)

( * ) Notice: Subject to any disclaimer, the term of this patent is extended or adjusted under 35 U.S.C. 154(b) by 187 days.

(21) Appl. No.: 17/777,219

(22) PCT Filed: Aug. 27, 2021

(86) PCT No.: PCT/JP2021/031457
§ 371 (c)(1),
(2) Date: May 16, 2022

(87) PCT Pub. No.: WO2023/276168
PCT Pub. Date: Jan. 5, 2023

(65) Prior Publication Data
US 2023/0281197 A1    Sep. 7, 2023

(30) Foreign Application Priority Data

Jun. 30, 2021 (JP) ................... 2021-108235
Jun. 30, 2021 (JP) ................... 2021-108326
Aug. 5, 2021 (JP) ................... 2021-128808

(51) Int. Cl.
*G06F 16/2453* (2019.01)
(52) U.S. Cl.
CPC .............. *G06F 16/2453* (2019.01)
(58) Field of Classification Search
CPC .................................. G06F 16/2453
(Continued)

(56) References Cited

U.S. PATENT DOCUMENTS

| 2008/0002740 A1* | 1/2008 | Ramachandran ....... H04L 69/32 370/469 |
| 2011/0276559 A1* | 11/2011 | Moe ....................... G06F 16/31 707/706 |

(Continued)

FOREIGN PATENT DOCUMENTS

| CN | 108647280 A | 10/2018 |
| JP | 2000-172714 A | 6/2000 |

(Continued)

OTHER PUBLICATIONS

International Search Report dated Oct. 5, 2021 issued in International Patent Application No. PCT/JP2021/031457, with English translation.

(Continued)

*Primary Examiner* — Hosain T Alam
*Assistant Examiner* — Saba Ahmed
(74) *Attorney, Agent, or Firm* — Rimon P.C.

(57) ABSTRACT

A search apparatus includes: an array index storage in which an array index having attribute position information for specifying a position at which an attribute value is located is stored for each of one or more records out of records and for each of one or more attributes of each record; a condition accepting unit that accepts a search condition including an attribute identifier corresponding to an attribute value; a search unit that retrieves attribute position information corresponding to the attribute identifier included in the search condition, from the array index, and retrieves an attribute value corresponding to the attribute identifier included in the search condition, using the attribute position information, from a data source storage in which a data source including two or more records having two or more attribute values is stored; and a result output unit that outputs a search result including the attribute value.

11 Claims, 47 Drawing Sheets

(58) Field of Classification Search
USPC .......................................................... 707/715
See application file for complete search history.

(56) References Cited

U.S. PATENT DOCUMENTS

| | | | |
|---|---|---|---|
| 2019/0251062 A1 | 8/2019 | Hakamata et al. | |
| 2020/0334382 A1 | 10/2020 | Yang et al. | |
| 2020/0379804 A1* | 12/2020 | Dalmia | G06F 9/545 |
| 2022/0188028 A1* | 6/2022 | Mesnier | G06F 3/067 |
| 2023/0281197 A1* | 9/2023 | Saeki | G16B 50/30 |
| | | | 707/715 |

FOREIGN PATENT DOCUMENTS

| | | | |
|---|---|---|---|
| JP | 2000-222434 A | 8/2000 | |
| JP | 2006-092409 A | 4/2006 | |
| JP | 2006-099427 A | 4/2006 | |
| JP | 2015-207026 A | 11/2015 | |
| JP | 2019-204337 A | 11/2019 | |
| WO | 2014/034383 A1 | 3/2014 | |
| WO | 2018/066144 A1 | 4/2018 | |

OTHER PUBLICATIONS

Extended European Search Report dated Jan. 5, 2024 issued in the European Patent Application No. 21893108.7.
Elmasri Ramez et al., "Indexing Structures for Files", pp. 631-675.
Ioannis Alagiannis et al., "NoDB: Efficient Query Execution on Raw Data Files", pp. 241-252.
Manos Karpathiotakis et al., "Adaptive Query Processing on RAW Data", pp. 1119-1130.
Singapore Search Report dated Mar. 5, 2024 issued in the corresponding Singapore Patent Application No. 11202203604Q.

* cited by examiner

<Source identifier> Sales database
<Table identifier> Sales table

| ID | Source attribute defining information | | |
|---|---|---|---|
| | Source attribute identifier | Data type | Size |
| 1 | Product ID | int | 4byte |
| 2 | Customer ID | int | 4byte |
| 3 | Unit selling price | int | 4byte |
| 4 | Sales quantity | int | 4byte |

FIG.24

<Source identifier> Sales database
<Table identifier> Product table

| ID | Source attribute defining information | | |
|---|---|---|---|
| | Source attribute identifier | Data type | Size |
| 1 | Product ID | Text | Undefined length |
| 2 | Product name | Text | Undefined length |
| 3 | Product category | Text | Undefined length |

FIG.25

<Source identifier>  Purchase database
<Table identifier>   Purchase table

| ID | Source attribute defining information |
|---|---|
|    | Source attribute identifier |
| 1  | Product ID |
| 2  | Supplier |
| 3  | Unit purchase price |

<Source identifier>  Sales database
<Source type identifier>  SQL database
<Connection information>
    <JDBC connection URL>
        jdbc:oracle:thin:@localhost:1521:AAA
    <Driver class>
        oracle.jdbc.driver.OracleDriver
</Connection information>
<Command base information>
    SELECT $extraction portion$
    FROM $table identifier 1$
      INNER JOIN $table identifier 2$
      ON $table identifier 1$. $table attribute identifier$ =
    $table identifier 2$. $table attribute identifier2$;
      WHERE $condition portion$ $remaining portion$
```

```
<Source identifier>  Purchase database
<Source type identifier>  REST API
<Connection information>
    <Base URL>
        https://xxx.yyyy-portal.co.jp
    <API key>
        XXXXXXXX
</Connection information>
<Command base information>
    Base URL+"/"+ endpoint
```

<View identifier> Sales view

| ID | View attribute defining informaton ||||
| | View attribute identifier | View attribute value base informaton |||
| | | Source identifier | Source attribute identifier | Operation expression, etc. |
|---|---|---|---|---|
| 1 | Product ID | Sales table | Product ID | — |
| | | Product table | Product ID | |
| 2 | Product Name | Product table | Product Name | — |
| 3 | Product category | Product table | Product category | — |
| 4 | Unit selling price | Sales table | Unit selling price | — |
| 5 | Sales quantity | Sales table | Sales quantity | — |
| 6 | Sales total | Sales table | Unit selling price | P1 / P1×P2 |
| | | Sales table | Sales quantity | P2 |

FIG.28

<View identifier> Purchase view

| ID | View attribute defining information | | | |
|---|---|---|---|---|
| | View attribute identifier | View attribute value base information | | |
| | | Source identifier | Source attribute identifier | Operation expression, etc. |
| 1 | Product ID | Purchase table | Product ID | — |
| 2 | Supplier | Purchase table | Supplier | — |
| 3 | Unit purchase price | Purchase table | Unit purchase price | — |

FIG.29

<User table identifier>  Product sales profit table

| ID | User attribute defining information | | | |
|---|---|---|---|---|
| | User attribute identifier | User attribute value base information | | |
| | | View identifier | View attribute identifier | Operation expression, etc. |
| 1 | Product ID | Sales view | Product ID | — |
| | | Purchase view | Product ID | |
| 2 | Product name | Sales view | Product name | — |
| 3 | Unit selling price | Sales view | Unit selling price | — |
| 4 | Sales quantity | Sales view | Sales quantity | — |
| 5 | Sales total | Sales view | Sales total | — |
| 6 | Unit purchase price | Purchase view | Unit purchase price | — |
| 7 | Purchase total | Sales view | Sales quantity | P1 | P1×P2 |
| | | Purchase view | Unit purchase price | P2 |
| 8 | Sales profit | Sales view | Sales total | P1 | sub(P1,P2) |
| | | Product sales profit table | Purchase total | P2 |

FIG.30

| [No.]<br>(Pos.) | PID | Age | Region | ... | TestA | TestB | ... |
|---|---|---|---|---|---|---|---|
| [1]<br>(1) | 236 | 40 | Tokyo | ... | 0.11 | 0.4 | ... |
| [2]<br>(121) | 029 | 50 | Nagoya | ... | 0.3 | 0.51 | |
| [3]<br>(241) | 155 | 30 | Tokyo | ... | 0.2 | 0.24 | ... |
| [4]<br>(361) | 103 | 20 | Osaka | ... | 0.423 | 0.38 | ... |
| [5]<br>(481) | 278 | 40 | Kyoto | ... | 0.272 | 0.3535 | ... |
| ... | ... | ... | ... | ... | ... | ... | ... |

FIG.44

SEARCH APPARATUS, SEARCH METHOD, AND STORAGE MEDIUM

CROSS-REFERENCE OF RELATED APPLICATIONS

This application is the U.S. National Phase under 35 U.S.C. § 371 of International Patent Application No. PCT/JP2021/031457, filed on Aug. 27, 2021, which in turn claims the benefit of Japanese Patent Application No. 2021-108325, filed on Jun. 30, 2021, Japanese Patent Application No. 2021-108326, filed on Jun. 30, 2021, and Japanese Patent Application No. 2021-128808, filed on Aug. 5, 2021, the entire disclosures of which Applications are incorporated by reference herein.

TECHNICAL FIELD

The present invention relates to a search apparatus and the like for searching for information.

BACKGROUND ART

Conventionally, there are search systems that use indexes to achieve high-speed search (see Patent Document 1, for example).

CITATION LIST

Patent Document

Patent Document 1: JP 2006-99427A

SUMMARY OF INVENTION

Technical Problem

However, according to conventional techniques, for example, it is difficult to perform high-speed search in a data source in which one record is very long.

For example, in data dealing with general genetic/genomic information, data such as nucleic acid sequences of genes and amino acid sequences of proteins is huge and often stored as arrays in the column direction of records, and thus the length of one record may be even several GBs. In many cases, data dealing with genetic/genomic information is stored and distributed in flat files (general text files) in a relatively simple layout.

Such data dealing with general genetic/genomic information can be dealt with in a conventional database as well, for example, if the data is converted into records in the row direction through expansion of arrays in the column direction and stored, but the data size further increases (e.g., by several dozen times), and thus this processing takes long time to perform conversion and storing processing, which extremely inefficient. In some cases, the entire file is read directly into a memory and processed using a dedicated program, or a non-relational database is used, but a large amount of memory resources are required to read the entire record, limiting the amount of data that can be processed at a time. Since the processing for data dealing with genetic/genomic information is not flexible, it is not easy to use the data flexibly in combination with other information such as personal attributes and medical history. In addition, special hardware and operations are required to process large amounts of data at high speed, and engineers with advanced skills are indispensable.

As described above, for example, according to conventional techniques, it is difficult to perform high-speed search in a data source in which one record is very long.

In view of this sort of problem, it is an object of the present invention, for example, to provide a technique with which even a data source in which one record is very long can be searched for information at high speed. Although the present invention can be also applied to data sources that do not have long record lengths, it is more effective for data sources with long record lengths.

Solution to Problem

A first aspect of the present invention is directed to a search apparatus including: an array index storage unit in which an array index having attribute position information for specifying a position at which an attribute value is located is stored for each of one or more records out of two or more records and for each of one or more attributes of each record; a condition accepting unit that accepts a search condition including an attribute identifier corresponding to an attribute value; a search unit that retrieves attribute position information corresponding to the attribute identifier included in the search condition, from the array index, and retrieves an attribute value corresponding to the attribute identifier included in the search condition, using the attribute position information, from a data source storage unit in which a data source including two or more records having two or more attribute values is stored; and a result output unit that outputs a search result including the attribute value retrieved by the search unit.

With this configuration, it is possible to search for information at high speed.

Furthermore, a second aspect of the present invention is directed to the search apparatus according to the first aspect, wherein an array index having attribute position information of each of one or more attribute values out of two or more attribute values included in each of the one or more records constituting part of the two or more records is stored in the array index storage unit, and the search unit retrieves first attribute position information corresponding to an attribute identifier for identifying an attribute value located before an attribute value identified with the attribute identifier included in the search condition and second attribute position information corresponding to an attribute identifier for identifying an attribute value located after the attribute value identified with the attribute identifier included in the search condition, and retrieves an attribute value located between a position specified with the first attribute position information and a position specified with the second attribute position information and corresponding to the attribute identifier included in the search condition, from the data source.

With this configuration, it is possible to search for information at higher speed.

Furthermore, a third aspect of the present invention is directed to the search apparatus according to the first or second aspect, further including: an array label index storage unit in which an array label index having attribute order information for specifying an order in which attribute position information of an attribute value is located is stored for each of two or more attributes, wherein the search unit retrieves attribute order information corresponding to the attribute identifier included in the search condition, from the array label indexes, retrieves attribute position information corresponding to the attribute identifier included in the search condition, from the array index, using the attribute order information, and retrieves an attribute value corresponding to the attribute identifier included in the search condition, from the data source, using the attribute position information.

With this configuration, it is possible to search for information at higher speed.

Furthermore, a fourth aspect of the present invention is directed to the search apparatus according to any one of the first to third aspects, further including: a record index storage unit in which a record index is stored, the record index being an index corresponding to a record of the data source and being two or more combinations of a key item value and record position information for specifying a position of a record including the key item value, wherein the data source includes two or more records having a key item value and two or more attribute values, the search condition has a key item value, and the search unit retrieves record position information that is paired with the key item value included in the search condition, from the record index, determines a record corresponding to a position specified with the record position information, and retrieves an attribute value included in the record and corresponding to the attribute identifier included in the search condition, from the data source.

With this configuration, it is possible to search for information at higher speed.

Furthermore, a fifth aspect of the present invention is directed to the search apparatus according to the fourth aspect, further including: a secondary index storage unit in which a secondary index is stored for each of one or more records constituting part of the two or more records, the secondary index being a combination of record index record position information for specifying a portion that is included in the record indexes and at which record position information is located, and a key item value of the record, wherein the search unit retrieves first record index record position information and second record index record position information corresponding to the key item value included in the search condition, from the secondary index, determines record index record position information between the first record index record position information and the second record index record position information, from the record indexes, retrieves record position information that is paired with the record index record position information, from the record indexes, determines a record corresponding to a position specified with the record position information, and retrieves an attribute value included in the record and corresponding to the attribute identifier included in the search condition, from the data source.

With this configuration, it is possible to search for information at higher speed.

Furthermore, a sixth aspect of the present invention is directed to the search apparatus according to any one of the first to fifth aspects, wherein the search condition has a key item value, two or more data sources each associated with a source identifier for identifying a data source are stored in the data source storage unit, the search apparatus further includes a source index storage unit in which a source index having a source identifier, a smallest key item value included in a data source identified with the source identifier, and a largest key item value included in the data source identified with the source identifier is stored for each of the two or more data sources, and the search unit retrieves a source identifier that matches the key item value included in the search condition or that is paired with a smallest key item value and a largest key item value between which the key item value is located, from the source index, retrieves attribute position information corresponding to the attribute identifier included in the search condition, from the array index, and retrieves an attribute value included in a record and corresponding to the attribute identifier included in the search condition, from the data source identified with the source identifier, using the attribute position information.

With this configuration, it is possible to search for information at higher speed.

Furthermore, a seventh aspect of the present invention is directed to the search apparatus according to any one of the first to fifth aspects, wherein two or more data sources each associated with a source identifier for identifying a data source are stored in the data source storage unit, the search apparatus further includes a source index storage unit in which a source index having a source identifier, a smallest attribute identifier included in the data source identified with the source identifier, and a largest attribute identifier included in the data source identified with the source identifier is stored for each of the two or more data sources, and the search unit retrieves a source identifier that matches the attribute identifier included in the search condition or that is paired with a smallest attribute identifier and a largest attribute identifier between which the attribute identifier is located, from the source index, retrieves attribute position information corresponding to the attribute identifier included in the search condition, from the array index, and retrieves an attribute value included in a record and corresponding to the attribute identifier included in the search condition, from the data source identified with the source identifier, using the attribute position information.

With this configuration, it is possible to search for information at higher speed.

Furthermore, an eighth aspect of the present invention is directed to the search apparatus according to any one of the first to seventh aspects, further including: an array index generating unit that retrieves attribute position information for specifying a position at which each of one or more attribute values is located, for each of one or more records out of two or more records in the data sources and for each attribute, generates the array index having the attribute position information, and accumulates the array index in the array index storage unit.

With this configuration, it is possible to automatically generate an index for searching for information at high speed.

Furthermore, a ninth aspect of the present invention is directed to the search apparatus according to the seventh aspect, wherein two or more data sources each associated with a source identifier for identifying a data source are stored in the data source storage unit, and the search apparatus further includes: an array label index generating unit that retrieves attribute order information for specifying a portion at which attribute position information is located, for each of two or more attributes, generates an array label index having the attribute order information, and accumulates the array label index in the array label index storage unit; a record index generating unit that refers to the data sources, generates a record index, which is a combination of a key item value and record position information of each of two or more records of the data sources, and accumulates the record index in the record index storage unit; a secondary index generating unit that retrieves a combination of record index record position information for specifying a portion at which record position information is located and a key item value of the record, for each of one or more records constituting part of the two or more records, generates a secondary index, and accumulates the secondary index in the secondary index storage unit, and a source index generating unit that retrieves a source identifier, a smallest key item value included in a data source identified with the source identifier, and a largest key item value included in the data source identified with the source identifier, for each of the two or more data sources, generates the source index having the source identifier, the smallest key item value, and the largest key item value, and accumulates the source index in the source index storage unit.

With this configuration, it is possible to automatically generate an index for searching for information at higher speed.

Furthermore, a tenth aspect of the present invention is directed to the search apparatus according to any one of the first to ninth aspects, wherein last updated time information for specifying a last updated time is associated with the data source, generated time information for specifying a time at which an array index is generated is associated with the array index, and the search apparatus further includes an index updating unit that, in a case in which a predetermined condition is satisfied, determines whether or not the last updated time indicated by the last updated time information is after the generated time indicated by the generated time information, and, in a case in which the last updated time is after the generated time, operates the array index generating unit to configure the array index.

With this configuration, it is possible to keep an index in the latest state.

Furthermore, the present invention is directed to a search apparatus for searching for information referring to a data dictionary having; source layer defining information, which is information defining each of two or more data sources including one or more records having one or more attribute values, and is information having a source identifier, which is an identifier of a data source, and one or more pieces of source attribute defining information each containing a source attribute identifier, which is an attribute identifier of a data source; user layer defining information, which is information defining a user table that is to be searched based on a search condition and that includes one or more records having one or more attribute values, and is information having a user table identifier for identifying the user table and one or more pieces of user attribute defining information each containing a user attribute identifier, which is an attribute identifier of the user table; and conversion rule defining information, which is information for generating a search command that is to be issued to each of the two or more data sources, based on the search condition, retrieving search results corresponding to the search command, and generating integrated data corresponding to the search condition using the two or more search results, including: a condition accepting unit that accepts a search condition for the user table; a search unit that determines two or more data sources corresponding to the search condition referring to the data dictionary, generates a search command for each of the two or more data sources, using the conversion rule defining information, retrieves search results based on the search command, and integrates the search results respectively corresponding to the two or more data sources using the conversion rule defining information and the user layer defining information, thereby retrieving integrated data corresponding to the search condition; and a result output unit that outputs the integrated data retrieved by the search unit.

With this configuration, it is possible to properly search two or more data sources for information and integrate search results.

Furthermore, the present invention is directed to the search apparatus according to the above-described aspect, wherein the conversion rule defining information has one or more pieces of conversion view information defining a conversion view configured using one or more data sources out of two or more data sources, the conversion view information is information defining a conversion view that may contain one or more records having one or more view attribute values, and has one or more pieces of view attribute defining information having a view attribute identifier corresponding to a view attribute value and view attribute value base information for specifying a method for retrieving a view attribute value, the user attribute defining information has user attribute value base information for specifying a method for retrieving a user attribute value using one or more view attribute values of one or more conversion views, and the search unit includes: a source determining part that retrieves one or more user attribute identifiers included in the search condition, retrieves user attribute value base information corresponding to the one or more user attribute identifiers, retrieves one or more view attribute identifiers corresponding to the user attribute value base information, and retrieves source identifiers corresponding to the one or more view attribute identifiers from the view attribute defining information; a command generating part that generates a search command for each of data sources identified with the two or more source identifiers retrieved by the source determining part, using the search condition and the view attribute value base information; a source search part that retrieves search results based on the search command from the two or more data sources; and an integrating part that retrieves integrated data obtained by integrating the search results of the respective two or more data sources retrieved by the source search part, using the search condition and the user layer defining information.

With this configuration, it is possible to properly search two or more data sources for information and integrate search results.

Furthermore, the present invention is directed to the search apparatus according to the above-described aspect, wherein any one piece of view attribute value base information out of the one or more pieces of view attribute value base information has one or more attribute identifiers out of source attribute identifiers of any two or more data sources and view attribute identifiers of any one or more conversion views, and an operation expression in which attribute values corresponding to the one or more attribute identifiers are taken as parameters or a program identifier, and, in a case of retrieving a view attribute value corresponding to the view attribute value base information, the search unit retrieves attribute values respectively corresponding to one or more attribute identifiers contained in the view attribute value base information, from the data sources or the conversion views, gives the retrieved one or more attribute values to the operation expression or a program identified with the program identifier, and executes the operation expression or the program, thereby retrieving a view attribute value.

With this configuration, it is possible to properly search two or more data sources for information and integrate search results.

Furthermore, the present invention is directed to the search apparatus according to the above-described aspect, wherein the conversion rule defining information has two or more pieces of conversion view information, and further has a join method identifier for specifying a method for joining two or more search results retrieved based on the two or more pieces of conversion view information, and the integrating part joins two or more search results according to a join method specified with the join method identifier, thereby retrieving integrated data.

With this configuration, it is possible to properly search two or more data sources for information and properly integrate search results.

Furthermore, the present invention is directed to the search apparatus according to the above-described aspect, wherein the conversion rule defining information has one of two or more join method identifiers out of three or more join method identifiers "UNION", "CHOICE", and "LOOKUP", wherein "UNION" is information indicating processing for joining two or more search results through merging processing that puts two or more search results into a group with a key item and aggregates two or more attribute values of non-key items, thereby configuring one record, "CHOICE" is information indicating processing for joining two or more search results through selection processing that selects an attribute value of a key item included in one or more search results out of two or more search results according to a priority order and aggregates two or more attribute values of non-key items, thereby configuring one record, and "LOOKUP" is information indicating processing for joining two or more search results through complementation processing that adds, to an attribute value of a key item of one search result out of two or more search results, an attribute value of a key item that is included in another search result different from the one search result and is not included in the one search result according to a reference condition and aggregates two or more attribute values of non-key items, thereby configuring one record.

With this configuration, it is possible to properly search two or more data sources for information and properly integrate search results.

Furthermore, the present invention is directed to the search apparatus according to the above-described aspect, wherein any one piece of user attribute value base information out of the one or more pieces of user attribute value base information has one or more attribute identifiers out of view attribute identifiers of any one or more conversion views and source attribute identifiers of any two or more data sources, and an operation expression in which attribute values corresponding to the one or more attribute identifiers are taken as parameters or a program identifier, and, in a case of retrieving a user attribute value corresponding to the user attribute value base information, the search unit retrieves attribute values respectively corresponding to one or more attribute identifiers contained in the user attribute value base information, from the conversion views or the data sources, gives the retrieved one or more attribute values to the operation expression or a program identified with the program identifier, and executes the operation expression or the program, thereby retrieving a user attribute value.

With this configuration, it is possible to properly search two or more data sources for information and integrate search results.

Furthermore, the present invention is directed to the search apparatus according to the above-described aspect, wherein the source layer defining information has command base information for generating a search command for data sources, pieces of command base information respectively corresponding to the two or more data sources are at least two or more different types of command base information, and the search unit generates a search command for retrieving information from each of the two or more data sources according to pieces of command base information respectively corresponding to the two or more data sources, retrieves search results based on the search command, and integrates the two or more search results, thereby retrieving integrated data.

With this configuration, it is possible to properly search two or more data sources for information and integrate search results.

Furthermore, the present invention is directed to the search apparatus according to the above-described aspect, wherein the two or more different types of command base information include information for generating a search command in an SQL statement and information for generating a search module, the search unit generates a search command that is an SQL statement according to command base information for a data source corresponding to the SQL statement and generates a search command that is an interface of a search module according to command base information, for a data source corresponding to the search module, according to pieces of command base information respectively corresponding to the two or more data sources, retrieves search results based on the search command, from the two or more data sources, and integrates the two or more search results, thereby retrieving integrated data.

With this configuration, it is possible to properly search two or more data sources for information and integrate search results.

Furthermore, the present invention is directed to the search apparatus according to the above-described aspect, wherein the source layer defining information has connection information for accessing each of the two or more data sources, and the search unit accesses the data sources corresponding to the connection information using the connection information, retrieves search results based on the search command from the data sources, and integrates the two or more search results, thereby retrieving integrated data.

With this configuration, it is possible to properly search two or more data sources for information and integrate search results.

Furthermore, the present invention is directed to the search apparatus according to the above-described aspect, wherein an array index having attribute position information for specifying a position at which an attribute value is located is stored for at least one or more data sources out of the two or more data sources, for each of one or more records out of two or more records included in the data sources and for each of one or more attributes of each record, and the search unit retrieves attribute position information corresponding to the attribute identifier included in the search condition, from the array index, and retrieves an attribute value corresponding to the attribute identifier included in the search condition from data sources, using the attribute position information, and configures integrated data having the attribute value.

With this configuration, it is possible to search for information at high speed.

Furthermore, the present invention is directed to the search apparatus, further including: a record index storage unit in which two or more record indexes respectively corresponding to combinations of different key items are stored, the record indexes being indexes corresponding to records of a data source including two or more records having key item values respectively corresponding to two or more key items and attribute values respectively corresponding to one or more attribute identifiers, and being two or more record indexes constituting a group of combinations of one or more key item values corresponding to a combination of one or more key items and record position information for specifying a position of a record including the one or more key item values; a condition accepting unit that accepts a search condition having a key item value; a search unit that selects one record index corresponding to a combination of one or more key items including a key item corresponding to the key item value included in the search condition, out of the two or more record indexes, retrieves record position information that is paired with the key item value included in the search condition, from the selected record index, and retrieves an attribute value in a record corresponding to a position specified with the record position information, from the data source; and a result output unit that outputs a search result including the attribute value retrieved by the search unit.

With this configuration, it is possible to search for information at high speed for a wide variety of search conditions.

Furthermore, the present invention is directed to the search apparatus according to the above-described aspect, further including: an array index storage unit in which an array index having attribute position information for specifying a position at which an attribute value is located is stored for each of one or more records out of two or more records and for each of one or more attributes of each record, wherein the search condition further has an attribute identifier, and the search unit retrieves attribute position information corresponding to the attribute identifier included in the search condition, from the array index, and retrieves an attribute value corresponding to the attribute identifier included in the search condition, from the data source, using the attribute position information.

With this configuration, it is possible to search for information at higher speed for a wide variety of search conditions.

Furthermore, the present invention is directed to the search apparatus according to the above-described aspect, wherein, in each of two or more record indexes, two or more combinations of one or more key item values and record position information are sorted using a combination of one or more key item values as a key, and, in a case in which a key item at a beginning of a record index matches a key item corresponding to the key item value included in the search condition, the search unit selects the record index out of the two or more record indexes, retrieves record position information that is paired with the key item value included in the search condition, from the selected record index, and retrieves an attribute value in a record corresponding to a position specified with the record position information, from the data source.

With this configuration, it is possible to search for information at high speed for a wide variety of search conditions.

Furthermore, the present invention is directed to the search apparatus according to the above-described aspect, wherein, in a case in which there are two or more record indexes in which a key item at a beginning of a record index matches a key item corresponding to the key item value included in the search condition, the search unit determines whether or not a key item following the two or more record indexes matches the key item included in the search condition, selects one record index in which a largest number of key items from the beginning of the record index are included in the key item included in the search condition, retrieves record position information that is paired with the key item value included in the search condition, from the selected record index, and retrieves an attribute value in a record corresponding to a position specified with the record position information, from the data source.

With this configuration, it is possible to search for information at high speed for a wide variety of search conditions.

Furthermore, the present invention is directed to the search apparatus according to the above-described aspect, further including a record index generating unit that refers to the data source, generates two or more record indexes that are each a combination of a key item value and record position information of each of two or more records of the data source, the two or more record indexes each corresponding to a combination of one or more different key items, and accumulates the record indexes in the record index storage unit.

With this configuration, it is possible to generate an index for searching for information at high speed for a wide variety of search conditions.

Furthermore, the present invention is directed to the search apparatus according to the above-described aspect, wherein the record index generating unit determines two or more combinations of one or more key items that satisfy a selecting condition, generates a record index, which is a combination of a key item value and record position information of each of two or more records corresponding to a combination of one or more key items of each of the two or more combinations, and accumulates the record index in the record index storage unit.

With this configuration, it is possible to generate a proper index for searching for information at high speed for a wide variety of search conditions.

Furthermore, the present invention is directed to the search apparatus according to the above-described aspect, wherein the selecting condition is being a combination of one or more key items including a key item corresponding to an attribute value in which a variance of attribute values included in two or more records of a data source is greater than or equal to a threshold or is greater than the threshold, or being a combination of one or more key items including a key item corresponding to an attribute value included at a frequency that is greater than or equal to a threshold or is greater than the threshold in previous one or more search conditions.

With this configuration, it is possible to generate a proper index for searching for information at high speed for a wide variety of search conditions.

Advantageous Effects of Invention

With the search apparatus according to the present invention, it is possible to search for information at high speed.

BRIEF DESCRIPTION OF DRAWINGS

FIG. 24 is a diagram showing an example of source layer defining information in the embodiment.

FIG. 25 is a diagram showing an example of source layer defining information in the embodiment.

FIG. 26 is a diagram showing an example of source layer defining information in the embodiment.

FIG. 27 is a diagram showing an example of data source-specific information in the embodiment.

FIG. 28 is a diagram showing conversion view information for a sales view in the embodiment.

FIG. 29 is a diagram showing conversion view information for a purchase view in the embodiment.

FIG. 30 is a diagram showing an example of user layer defining information in the embodiment.

FIG. 44 is a diagram showing an example of a data source in the embodiment.

DESCRIPTION OF EMBODIMENT

Figure 1:
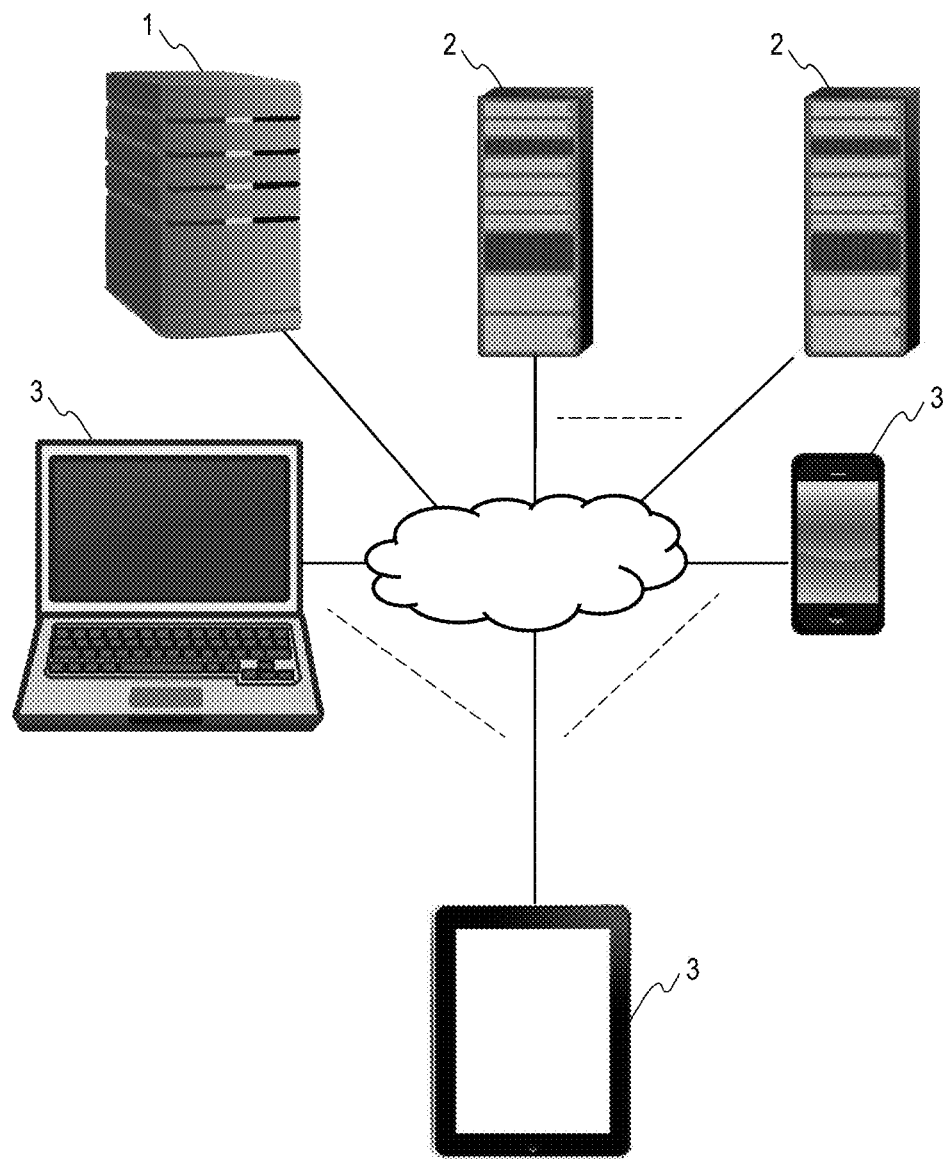
FIG. 1 is a conceptual diagram of a search system A in Embodiment 1.

Hereinafter, embodiments of a search apparatus and the like will be described with reference to the drawings. It should be noted that constituent elements denoted by the same reference numerals in the embodiments perform similar operations, and thus a description thereof may not be repeated.

Embodiment 1

In this embodiment, a search system including a search apparatus that searches a data source for information using one or more types of indexes will be described. The one or more types of indexes are, for example, a later-described array index, a later-described array label index, a later-described record index, a later-described secondary index, or a later-described source index.

Furthermore, in this embodiment, a search system including a search apparatus that generates one or more types of indexes corresponding to a data source, using the data source will be described.

Moreover, in this embodiment, a search system including a search apparatus that automatically updates an index will be described.

FIG. 1 is a conceptual diagram of a search system A in in this embodiment. The search system A includes, for example, a search apparatus 1, one or at least two data source management apparatuses 2, and one or at least two terminal apparatuses 3.

The search apparatus 1 is an apparatus that searches a data source for information. The data source management apparatuses 2 are apparatuses in which one or at least two data sources are stored. The terminal apparatuses 3 are terminals that are used by users when searching for information.

The search apparatus 1 and the data source management apparatuses 2 are, for example, so-called servers such as cloud servers, ASP servers, or the like. There is no limitation on the type of the search apparatus 1 and the data source management apparatuses 2. The search apparatus 1 may be a stand-alone apparatus. In this case, the search system A does not have to include the data source management apparatuses 2 and the terminal apparatuses 3. In this case, data sources are stored in the search apparatus 1.

Figure 2:
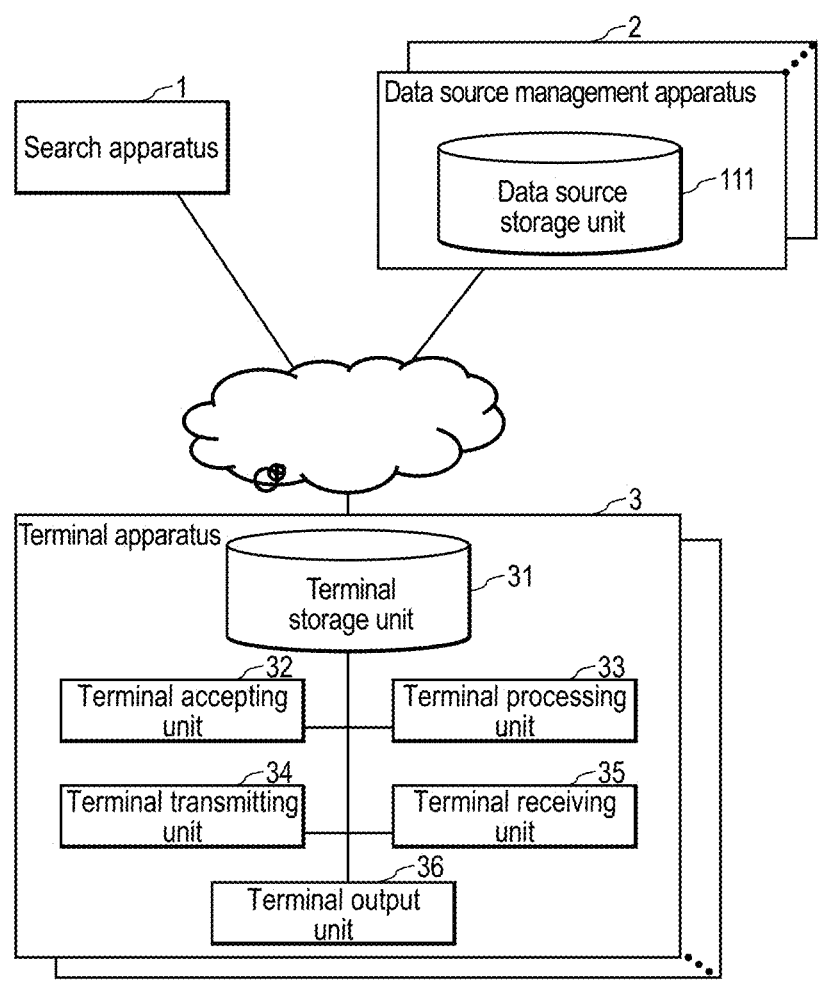
FIG. 2 is a block diagram of the search system A in the embodiment.
Figure 3:
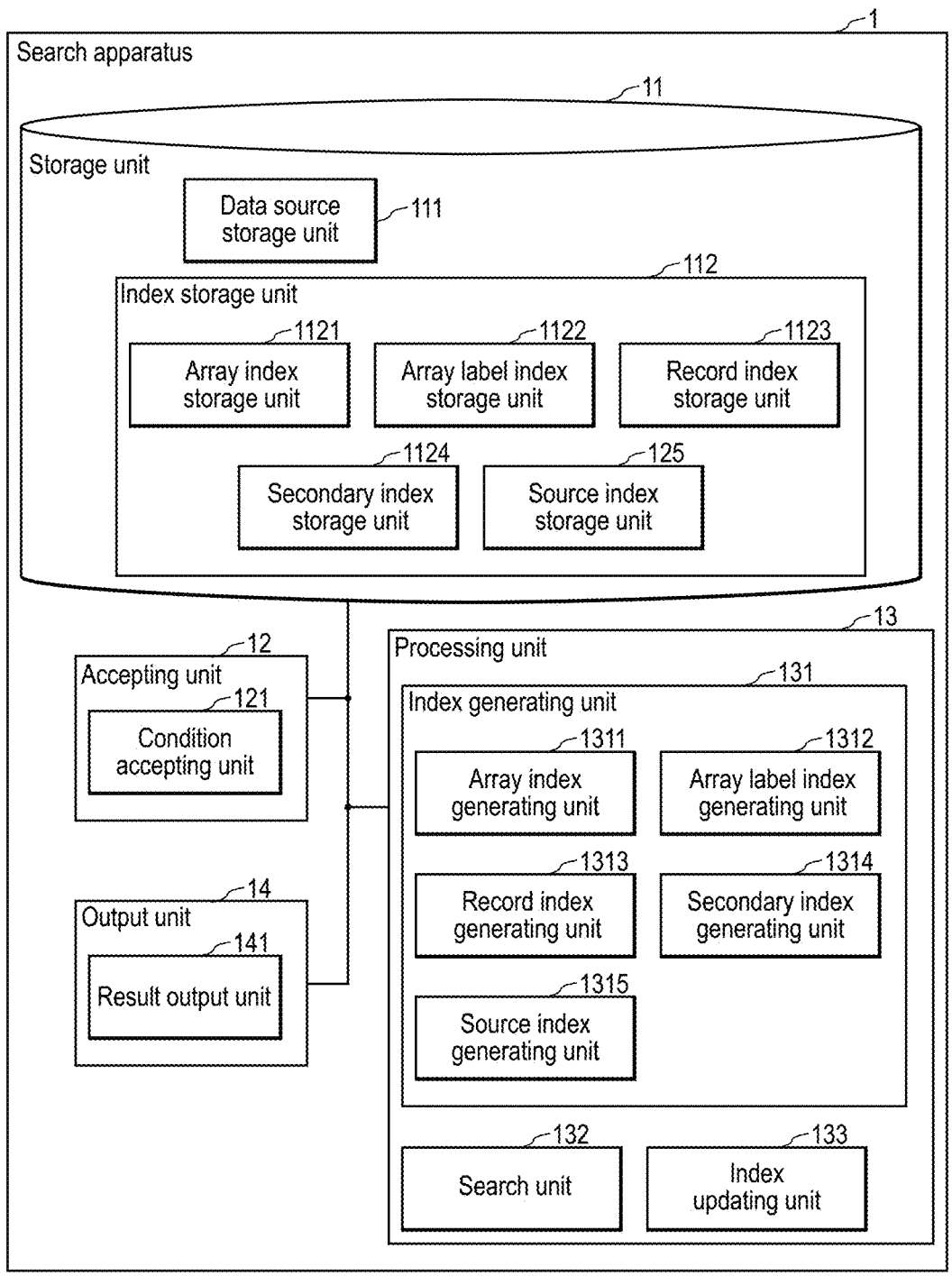
FIG. 3 is a block diagram of a search apparatus 1 constituting the search system A in the embodiment.

FIG. 2 is a block diagram of the search system A in this embodiment. FIG. 3 is a block diagram of the search apparatus 1 constituting the search system A.

The search apparatus 1 includes a storage unit 11, an accepting unit 12, a processing unit 13, and an output unit 14. The storage unit 11 includes a data source storage unit 111 and an index storage unit 112. The index storage unit 112 includes an array index storage unit 1121, an array label index storage unit 1122, a record index storage unit 1123, a secondary index storage unit 1124, and a source index storage unit 1125. The accepting unit 12 includes a condition accepting unit 121. The processing unit 13 includes an index generating unit 131, a search unit 132, and an index updating unit 133. The index generating unit 131 includes an array index generating unit 1311, an array label index generating unit 1312, a record index generating unit 1313, a secondary index generating unit 1314, and a source index generating unit 1315. The output unit 14 includes a result output unit 141.

Each data source management apparatus 2 includes a data source storage unit 111.

Each terminal apparatus 3 includes a terminal storage unit 31, a terminal accepting unit 32, a terminal processing unit 33, a terminal transmitting unit 34, a terminal receiving unit 35, and a terminal output unit 36.

Various types of information are stored in the storage unit 11 constituting the search apparatus 1. The various types of information are, for example, a later-described data source or later-described one or more types of indexes.

One or at least two data sources are stored in the data source storage unit 111. The search apparatus 1 does not have to include the data source storage unit 111. In this case, a data source targeted for search is stored in the data source management apparatus 2.

A data source is a group of data targeted for search. Data may also be said to be information. The data source is typically one file. Note that the data source may be, for example, one database, a table in a database, or the like. The data source typically has one or at least two records. A record may also be said to be, for example, a row, a tuple, or the like. Records are each defined, for example, by a first delimiter or the like, and thus a boundary therebetween can be recognized. The first delimiter is, for example, a return code, a TAB code, a space, or the like, but there is no limitation on the type thereof. The data source may have data other than that targeted for search. The data other than that targeted for search is, for example, an item label or an attribute identifier. The item label is a label of an item, but may be an item name. The item has, for example, a key item and a detailed item. A key item is an identifier for a key item value. Two or more key items may be located in one record. A detailed item is an item including a key item. The key item and the detailed item may be considered to be attribute identifiers. That is to say, the key item value and the detailed item value may be considered to be attribute values constituting a record. An attribute identifier is information for identifying an attribute. The attribute identifier is, for example, an attribute name or an attribute ID. A record typically has two or more attribute values. The record may have a key item value and a detailed item value. Note that the record may be one attribute value. Attribute values in a record are each defined, for example, by a second delimiter, and thus a boundary therebetween can be recognized. The second delimiter is, for example, a comma ",", a colon ":", a semicolon ";", a space, a TAB code, or the like, but there is no limitation on the type thereof. A data source is associated with a source identifier. The source identifier is information for identifying a data source, and is, for example, a file name or a file ID. The key item value is, for example, predetermined. The state of being predetermined typically means that the value has been determined through designation by a user when an index is generated.

An attribute value in a data source typically has a length that is not fixed but variable. A record in a data source also typically has a length that is not fixed but variable. Note that the attribute value or the record in a data source may have a fixed length.

It is preferable that a data source is associated with one or more source attribute values. A source attribute value is an attribute value of a data source. The source attribute value is, for example, last updated time information, an updater identifier, a size, or a type identifier. The last updated time information is information for specifying a time when a data source was last updated, and is expressed in, for example, year/month/day/hour/minute/second or month/day/hour/minute. The updater identifier is information for identifying an updater (typically a last updater) of a data source. The size is a data size of a data source, and is expressed in, for example, the number of bytes or the number of bits. The type identifier is information for specifying the type of data source, and is, for example, "file", "RDB", or "table". The "file" indicates that the data source is a file. The "RDB" indicates that the data source is an RDB (a relational database). The "table" indicates that the data source is tabular information.

One or at least two types of indexes are stored in the index storage unit 112. An index is information that is referred to during search in a data source for desired information. The index is, for example, a later-described array index, a later-described array label index, a later-described record index, a later-described secondary index, or a later-described source index.

The one or more types of indexes are, for example, files. Note that the indexes may be information in a database such as an RDB, and there is no limitation on the physical structure thereof. The information in a database is, for example, a table.

It is preferable that an index is associated with generated time information. The generated time information is information for specifying a time when an index was generated, and is expressed in, for example, year/month/day/hour/minute/second or month/day/hour/minute.

An array index is stored in the array index storage unit 1121. The array index is stored in the array index storage unit 1121 typically for each data source. That is to say, the array index is typically associated with a source identifier for identifying a data source. In the case in which the number of data sources targeted for search is one, the array index does not have to be associated with a source identifier.

The array index is information for specifying a position of an attribute value in a record. The array index has one or more array index records, which are information for each record included in a data source. An array index record has attribute position information for each attribute of each record. The attribute position information is information for specifying a position at which an attribute value is located. The attribute position information is typically an offset of an attribute value in a record. Note that the attribute position information may be an offset or the like in a data source. The attribute position information is associated with, for example, a record identifier for identifying a record and an attribute identifier.

It is preferable that the array index has attribute position information of some attribute values corresponding to all records, but it may have attribute position information of all attribute values corresponding to all records included in a data source, may have attribute position information of all attribute values corresponding to some records, or may have attribute position information of some attribute values corresponding to some records.

In the case in which the array index only has attribute position information of some attribute values, the array index has attribute position information in the order of attribute values in a record of a data source.

An array label index is stored in the array label index storage unit 1122. The array label index is stored in the array label index storage unit 1122 typically for each data source. That is to say, the array label index is typically associated with a source identifier. In the case in which the number of data sources targeted for search is one, the array label index does not have to be associated with a source identifier.

The array label index is information for specifying the order of attributes in a record of a data source. The array label index has one or more array label index records, which are information for each record included in a data source. An array label index record is information indicating the order of attributes in a record. The array label index record is, for example, a combination of an attribute identifier and attribute order information. The two or more array label index records may be, for example, attribute identifiers arranged in the order in a record. It is preferable that the array label index is information for specifying the order of all attributes in a record. It is preferable that the attribute identifiers are sorted in the array label index.

A record index is stored in the record index storage unit 1123. The record index is stored in the record index storage unit 1123 typically for each data source. That is to say, the record index is typically associated with a source identifier. In the case in which the number of data sources targeted for search is one, the record index does not have to be associated with a source identifier.

The record index is an index corresponding to a record of the data source. The record index has one or more record index records for specifying a position of a record of a data source. A record index record has a key item value or a combination of two or more key item values, and record position information. The record index record may be a combination of a key item value, record position information, and record index record position information.

Furthermore, it is preferable that there is another record index having different key item values in the same record, or a combination of key item values and record position information.

A key item value is an attribute value included in a record, and is an attribute value functioning as a key. It is preferable that the key item value is unique information with which a record can be identified, but it does not have to be unique information.

The record position information is information for specifying a position of a record including the key item value. The record position information is, for example, an offset in a data source, for specifying a position of a record. The record position information is, for example, an offset of the beginning of a record. The record position information may be, for example, an offset of the last piece of information in a record.

The record index record position information is information for specifying a position of a record index record in a record index. The record index record position information is, for example, an offset of a record index record in a record index.

It is preferable that the key item values are sorted in the record index.

Furthermore, it is preferable that a record index record is associated with an array index record. The record index record and the array index record are associated with each other, for example, via a key item value.

A secondary index is stored in the secondary index storage unit 1124. The secondary index is stored in the secondary index storage unit 1124 typically for each data source. That is to say, the secondary index is typically associated with a source identifier. In the case in which the number of data sources targeted for search is one, the secondary index does not have to be associated with a source identifier.

The secondary index is an index for accessing a record index at high speed. The secondary index is information corresponding to one or more records, which are some two or more records included in a data source. The secondary index has a secondary index record for each record. The secondary index record is a combination of a key item value and record index record position information. The record index record position information is information for specifying a portion that is in a record index and at which record position information is located. The key item value is a key item value included in a record.

It is preferable that the key item values are sorted in the secondary index.

A source index is stored in the source index storage unit 1125. The source index is an index for each data source. The source index is, for example, a group of source index records for each data source.

A source index record is, for example, a combination of a source identifier, the smallest key item value, and the largest key item value. The smallest key item value is the smallest key item value included in a data source identified with the source identifier. The largest key item value is the largest key item value included in a data source identified with the source identifier. In this case, typically, different records are stored in the two or more data sources.

The source index record is, for example, a combination of a source identifier, the smallest attribute identifier, and the largest attribute identifier. The smallest attribute identifier is the smallest attribute identifier included in a data source identified with the source identifier. The largest attribute identifier is the largest attribute identifier included in a data source identified with the source identifier. In this case, typically, attribute values of different attributes are stored in the two or more data sources.

The source index record is, for example, a combination of a source identifier, the smallest key item value, the largest key item value, the smallest attribute identifier, and the largest attribute identifier. In this case, typically, attribute values of some attributes of some records are stored in the two or more data sources.

The accepting unit 12 accepts various types of instructions and information. The various types of instructions and information are, for example, a later-described search condition, a data source, or part of the information constituting the data source.

The accepting is typically receiving from the terminal apparatus 3, but may be a concept that encompasses accepting information input from an input device such as a keyboard, a mouse, or a touch panel, and accepting information read from a storage medium such as an optical disk, a magnetic disk, or a semiconductor memory.

The condition accepting unit 121 accepts a search condition. The search condition includes, for example, one or at least two attribute identifiers. The search condition includes, for example, one or at least two key item values. The search condition includes, for example, one or more attribute identifiers and one or more key item values.

The processing unit 13 performs various types of processing. The various types of processing are, for example, processing that is performed by the index generating unit 131, the search unit 132, and the index updating unit 133.

In the case in which the accepting unit 12 accepts a data source, the processing unit 13 accumulates the data source in the data source storage unit 111. At that time, the processing unit 13 retrieves last updated time information from an unshown clock, and associates the last updated time information with the data source.

In the case in which the accepting unit 12 accepts part of the information constituting the data source, the processing unit 13 updates a data source using the part of the information. At that time, the processing unit 13 retrieves last updated time information from an unshown clock, and associates the last updated time information with the data source.

The index generating unit 131 generates an index from each of the one or at least two data sources.

The array index generating unit 1311 generates an array index for each of the one or more data sources, and accumulates it in the array index storage unit 1121.

The array index generating unit 1311 retrieves attribute position information for each record in a data source and for each of the one or more attribute values.

It is preferable that the array index generating unit 1311 retrieves an array index record having attribute position information of some attribute values, for each of all records in the data source, configures an array index having the one or more array index records, and accumulates it in the array index storage unit 1121. Note that the array index generating unit 1311 may retrieve an array index record having attribute position information of each of all attribute values, for each of all records in the data source, configure an array index having the one or more array index records, and accumulate it in the array index storage unit 1121.

It is preferable that the array index record is information only having attribute position information of some attribute values, out of all attribute values in a record. There is no limitation on the method for selecting such some attribute values. It is preferable that some attribute values are selected, for example, at every predetermined number of values (e.g., every four values, such as the $1^{-st}$ value, the $5^{-th}$ value, the $9^{-th}$ value, etc.), but a predetermined number of attribute values may be selected at random.

The array index generating unit 1311 retrieves attribute position information for each of one or more records out of two or more records in the data source and for each of one or more attribute values. Then, the array index generating unit 1311 generates an array index having attribute position information for each record and for each attribute value, and accumulates it in the array index storage unit 1121.

For example, the array index generating unit 1311 accumulates the retrieved attribute position information in the array index storage unit 1121 such that it is associated with a record identifier or a key item value and an attribute value identifier.

The array index generating unit 1311 typically scans a data source, recognizes a record at every first delimiter, scans the record, recognizes an attribute value at every second delimiter, and retrieves, as the attribute position information of the attribute value, for example, a position following the second delimiter from the beginning of the record.

The array label index generating unit 1312 generates an array label index for each of the one or more data sources, and accumulates it in the array label index storage unit 1122.

For example, the array label index generating unit 1312 retrieves an attribute value identifier and attribute order information for each of two or more attributes, from a data source, retrieves an array label index record, which is a combination of the attribute value identifier and the attribute order information, configures an array label index having the two or more array label index records, and accumulates the array label index in the array label index storage unit 1122.

It is preferable that the array label index generating unit 1312 sorts the array label index records using the attribute value identifiers as a key, and configures an array label index.

Furthermore, in the case in which an array index record has attribute position information of all attribute values, the array label index is not necessary.

The record index generating unit 1313 refers to a data source, and retrieves, for each of two or more records, a record index record having a key item value and record position information of the record of the data source. Then, the record index generating unit 1313 generates a record index having a group of record index records for the respective records, and accumulates it in the record index storage unit 1123.

It is preferable that the record index generating unit 1313 retrieves, for each of the one or more record index records, record index record position information for specifying a position of a record index record in the record index, and configures a record index record having the record index record position information.

It is preferable that the record index generating unit 1313 sorts the record index records using the key item values as a key, and configures a record index.

The secondary index generating unit 1314 retrieves, for each data source and for each of one or more records constituting part of the two or more records included in the data source, a secondary index record, which is a combination of record index record position information and a key item value of the record, configures a secondary index having the one or more secondary index records, and accumulates it in the secondary index storage unit 1124.

Furthermore, in the case in which attribute value position information of an array index is information for specifying a position in a data source, the record index is not absolutely necessary.

For example, the secondary index generating unit 1314 refers, for each data source, a record index corresponding to the data source, retrieves a secondary index record, which is a combination of record index record position information included in each of two or more records, the records being some records included in the record index, and a key item value, generates a secondary index having the two or more secondary index records, and accumulates it in the secondary index storage unit 1124.

A secondary index record corresponds to some record index records, but there is no limitation on the method for selecting such some record index records. It is preferable that some record index records are selected, for example, at every predetermined number of records (e.g., every four values, such as the $1^{-st}$ record, the $5^{-th}$ record, the $9^{-th}$ record, etc.), but a predetermined number of records may be selected at random.

A secondary index makes it possible to search for a record at high speed, but it is not absolutely necessary.

The source index generating unit 1315 retrieves a source index record for each of the two or more data sources, generates a source index having the two or more source index records, and accumulates it in the source index storage unit 1125. The source index record is, for example, a combination of a source identifier, the smallest key item value, and the largest key item value. The source index record is, for example, a combination of a source identifier, the smallest attribute identifier, and the largest attribute identifier. The source index record is, for example, a combination of a source identifier, the smallest key item value, the largest key item value, the smallest attribute identifier, and the largest attribute identifier.

In the case in which the number of data sources is one, the source index generating unit 1315 is not necessary.

The search unit 132 retrieves attribute position information corresponding to the attribute identifier included in the search condition, from the array index, and retrieves an attribute value corresponding to the attribute identifier included in the search condition, from a data source including one or at least two records having key item values and two or more attribute values, using the attribute position information.

For example, the search unit 132 retrieves first attribute position information corresponding to an attribute identifier for identifying an attribute value located before an attribute value identified with the attribute identifier included in the search condition accepted by the condition accepting unit 121 and second attribute position information corresponding to an attribute identifier for identifying an attribute value located after the attribute value identified with the attribute identifier included in the search condition, from the array index. Next, the search unit 132 retrieves an attribute value located between a position specified with the first attribute position information and a position specified with the second attribute position information and corresponding to the attribute identifier included in the search condition, from the data source.

For example, the search unit 132 retrieves attribute order information corresponding to the attribute identifier included in the search condition accepted by the condition accepting unit 121, from the array label indexes. Next, the search unit 132 retrieves attribute position information corresponding to the attribute identifier included in the search condition, from the array index, using the attribute order information. Next, the search unit 132 retrieves an attribute value corresponding to the attribute identifier included in the search condition, from the data source, using the attribute position information.

For example, the search unit 132 retrieves attribute order information corresponding to the attribute identifier included in the search condition accepted by the condition accepting unit 121, from the array label indexes. The search unit 132 retrieves first attribute position information corresponding to an attribute identifier for identifying an attribute value located before the order indicated by the attribute order information and second attribute position information corresponding to an attribute identifier for identifying an attribute value located after the order indicated by the attribute order information, from the array index. Next, the search unit 132 retrieves an attribute value located between a position specified with the first attribute position information and a position specified with the second attribute position information and corresponding to the attribute identifier included in the search condition, from the data source.

For example, the search unit 132 retrieves record position information that is paired with the key item value included in the search condition, from the record indexes. Next, the search unit 132 determines a record corresponding to a position specified with the record position information, and retrieves an attribute value included in the record and corresponding to the attribute identifier included in the search condition, from the data source. In the case in which the search condition does not indicate the attribute identifier, it may be considered that the attribute identifier included in the search condition is all attribute identifiers.

For example, the search unit 132 retrieves two key item values between which the key item value included in the search condition is located, from the secondary index. Next, the search unit 132 retrieves first record index record position information and second record index record position information that are paired with the retrieved two key item values, from the secondary index. Next, the search unit 132 searches for a record index record between the first record index record position information and the second record index record position information, determines a record index record including the key item value included in the search condition, and retrieves record position information in the record index record. Next, the search unit 132 retrieves an attribute value included in a record corresponding to a position specified with the record position information and corresponding to the attribute identifier included in the search condition, from the data source. It is preferable that the search unit 132 retrieves attribute position information of an attribute value corresponding to the attribute identifier included in the search condition, using the array index, and retrieves an attribute value at a position specified with the attribute position information from the data source.

Furthermore, in the case in which the key item values are sorted in the record index, the search method by which the search unit 132 determines a record index record including the key item value included in the search condition is preferably binary search, but may be sequential search.

For example, the search unit 132 retrieves a source identifier that matches the key item value included in the search condition or that is paired with the smallest key item value and the largest key item value between which the key item value is located, from the source index. Next, the search unit 132 retrieves attribute position information corresponding to the attribute identifier included in the search condition, from the array index, from a data source identified with the source identifier. Next, the search unit 132 retrieves an attribute value included in a record and corresponding to the attribute identifier included in the search condition, using the attribute position information.

For example, the search unit 132 retrieves a source identifier that matches the attribute identifier included in the search condition or that is paired with the smallest attribute identifier and the largest attribute identifier between which the attribute identifier is located, from the source index. The search unit 132 retrieves attribute position information corresponding to the attribute identifier included in the search condition, from the array index corresponding to the data source identified with the source identifier. The search unit 132 retrieves, the attribute value being included in a record and corresponding to the attribute identifier included in the search condition a data source identified with the source identifier, using the attribute position information.

For example, the search unit 132 retrieves a source identifier corresponding to the key item value included in the search condition and the attribute identifier included in the search condition, from the source index. The search unit 132 retrieves two key item values between which the key item value included in the search condition is located, from the secondary index corresponding to the data source identified with the source identifier. Next, the search unit 132 retrieves first record index record position information and second record index record position information that are paired with the retrieved two key item values, from the secondary index.

Next, the search unit 132 searches for a record index record between the first record index record position information and the second record index record position information, determines a record index record including the key item value included in the search condition, and retrieves record position information in the record index record. The search unit 132 retrieves attribute order information corresponding to the attribute identifier included in the search condition, from the array label indexes. Next, the search unit 132 retrieves attribute position information corresponding to the attribute identifier included in the search condition, from the array index, using the attribute order information. Next, the search unit 132 retrieves an attribute value included in a record specified with the retrieved record position information, the attribute value being specified with the attribute position information, from the data source.

In the case in which a predetermined condition is satisfied, the index updating unit 133 determines whether or not the last updated time indicated by the last updated time information retrieved from the data source is after the generated time indicated by the generated time information corresponding to each of the one or more types of indexes, and, in the case in which the last updated time is after the generated time, the index updating unit operates the index generating unit 131 to configure each of the one or more types of indexes. The index updating unit 133 typically overwrites old indexes in the index storage unit 112 to the configured respective one or more types of indexes. The one or more types of indexes are one or more of an array index, an array label index, a record index, a secondary index, and a source index. The predetermined condition is, for example, that an instruction from a user has been accepted, that it has reached predetermined time, or that it has a data source has been updated.

The output unit 14 retrieves various types of information. The various types of information are, for example, a later-described search result. The output is typically transmission to the terminal apparatus 3, but may be a concept that encompasses display on a display screen, projection using a projector, printing by a printer, accumulation in a storage medium, delivery of a processing result to another processing apparatus or another program, and the like.

The result output unit 141 outputs a search result including the attribute value retrieved by the search unit 132. The search result typically has an attribute value.

The data source management apparatus 2 manages one or more data sources. The data source management apparatus 2 includes the data source storage unit 111.

Various types of information are stored in the terminal storage unit 31 constituting the terminal apparatus 3. The various types of information are, for example, a search condition or a data source.

The terminal accepting unit 32 accepts various types of instructions and information. The various types of instructions and information are, for example, a search condition, a data source, or part of information in a data source.

The accepting is a concept that encompasses accepting information input from an input device such as a keyboard, a mouse, or a touch panel, receiving information transmitted via a wired or wireless communication line, accepting information read from a storage medium such as an optical disk, a magnetic disk, or a semiconductor memory, and the like.

The terminal processing unit 33 performs various types of processing. The various types of processing are, for example, processing that converts the data structure of instructions or information accepted by the terminal accepting unit 32 to that of instructions or information to be transmitted. The various types of processing are, for example, processing that converts the data structure of information received by the terminal receiving unit 35 to that of information to be output.

The terminal transmitting unit 34 transmits various types of information or instructions. The terminal transmitting unit 34 typically transmits various types of information or instructions to the search apparatus 1. The various types of information or instructions are, for example, a search condition or a data source.

The terminal receiving unit 35 receives various types of information. The terminal receiving unit 35 receives various types of information from the search apparatus 1. The various types of information are, for example, a search result.

The terminal output unit 36 outputs various types of information. The various types of information are, for example, a search result.

The storage unit 11, the data source storage unit 111, the index storage unit 112, the array index storage unit 1121, the array label index storage unit 1122, the record index storage unit 1123, the secondary index storage unit 1124, the source index storage unit 1125, and the terminal storage unit 31 are preferably non-volatile storage media, but can also be realized by volatile storage media.

There is no limitation on the procedure in which information is stored in the storage unit 11 and the like. For example, information may be stored in the storage unit 11 and the like via a storage medium, information transmitted via a communication line or the like may be stored in the storage unit 11 and the like, or information input via an input device may be stored in the storage unit 11 and the like.

The accepting unit 12, the condition accepting unit 121, and the terminal receiving unit 35 are typically realized by wired or wireless communication parts, but may also be realized by broadcast receiving parts.

The processing unit 13, the index generating unit 131, the search unit 132, the index updating unit 133, the array index generating unit 1311, the array label index generating unit 1312, the record index generating unit 1313, the secondary index generating unit 1314, the source index generating unit 1315, and the terminal processing unit 33 may be realized typically by processors, memories, or the like. Typically, the processing procedure of the processing unit 13 and the like is realized by software, and the software is stored in a storage medium such as a ROM. Note that the processing procedure may be realized by hardware (a dedicated circuit). The processors are, for example, CPUs, MPUs, or GPUs, but there is no limitation on the type thereof.

The output unit 14, the result output unit 141, and the terminal transmitting unit 34 are typically realized by wired or wireless communication parts, but may also be realized by broadcasting parts.

The terminal accepting unit 32 may be realized by a device driver for an input device such as a touch panel or a keyboard, control software for a menu screen, or the like.

The terminal output unit 36 may be considered to include or to not include an output device such as a display screen or a speaker. The terminal output unit 36 may be realized by driver software for an output device, a combination of driver software for an output device and the output device, or the like.

Next, an operation example of the search system A will be described. First, an operation example of the search apparatus 1 will be described with reference to the flowchart in FIG. 4.

(Step S401) The index generating unit 131 determines whether or not it is time to generate an index. If it is time to generate an index, the procedure advances to step S402, or otherwise the procedure advances to step S406.

(Step S402) The index generating unit 131 substitutes 1 for a counter i.

(Step S403) The index generating unit 131 determines whether or not there is an $i^{-th}$ data source for which an index is to be generated. If there is an $i^{-th}$ data source, the procedure advances to step S404, or otherwise the procedure returns to step S401.

(Step S404) The index generating unit 131 generates an index corresponding to the $i^{-th}$ data source. Below, an example of index generating processing will be described with reference to the flowchart in FIG. 5.

(Step S405) The index generating unit 131 increments the counter i by 1. The procedure returns to step S403.

(Step S406) The index updating unit 133 determines whether or not it is time to update the index. If it is time to update the index, the procedure advances to step S407, or otherwise the procedure advances to step S414.

(Step S407) The index updating unit 133 substitutes 1 for a counter i.

(Step S408) The index updating unit 133 determines whether or not there is an $i^{-th}$ data source. If there is an $i^{-th}$ data source, the procedure advances to step S409, or otherwise the procedure returns to step S401.

(Step S409) The index updating unit 133 retrieves last updated time information that is an attribute value of the $i^{-th}$ data source.

(Step S410) The index updating unit 133 retrieves generated time information of the index (e.g., array index) corresponding to the $i^{-th}$ data source from the array index storage unit 1121.

(Step S411) The index updating unit 133 determines whether or not the time indicated by the last updated time information retrieved in step S409 is after the time indicated by the generated time information retrieved in step S410. If the time indicated by the last updated time information is after the time indicated by the generated time information, the procedure advances to step S412, or otherwise the procedure advances to step S413.

Figure 5:
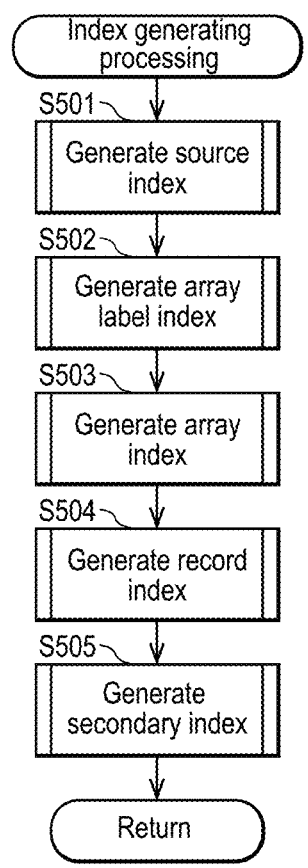
FIG. 5 is a flowchart illustrating of an example of index generating processing in the embodiment.

(Step S412) The index updating unit 133 instructs the index generating unit 131 to operate. As a result, the index generating unit 131 generates an index, and accumulates the index in association with the $i^{-th}$ data source. Through this processing, the index corresponding to the $i^{-th}$ data source is updated. The flowchart in FIG. 5 shows an example of the index generating processing.

(Step S413) The counter i is incremented by 1. The procedure returns to step S408.

(Step S414) The condition accepting unit 121 determines whether or not it has accepted a search condition. If it has accepted a search condition, the procedure advances to step S415, or otherwise the procedure returns to step S401.

(Step S415) The search unit 132 performs search using the search condition. Below, an example of the search processing will be described with reference to the flowchart in FIG. 11.

(Step S416) The result output unit 141 outputs the search result retrieved in step S415. The procedure returns to step S401.

Figure 4:
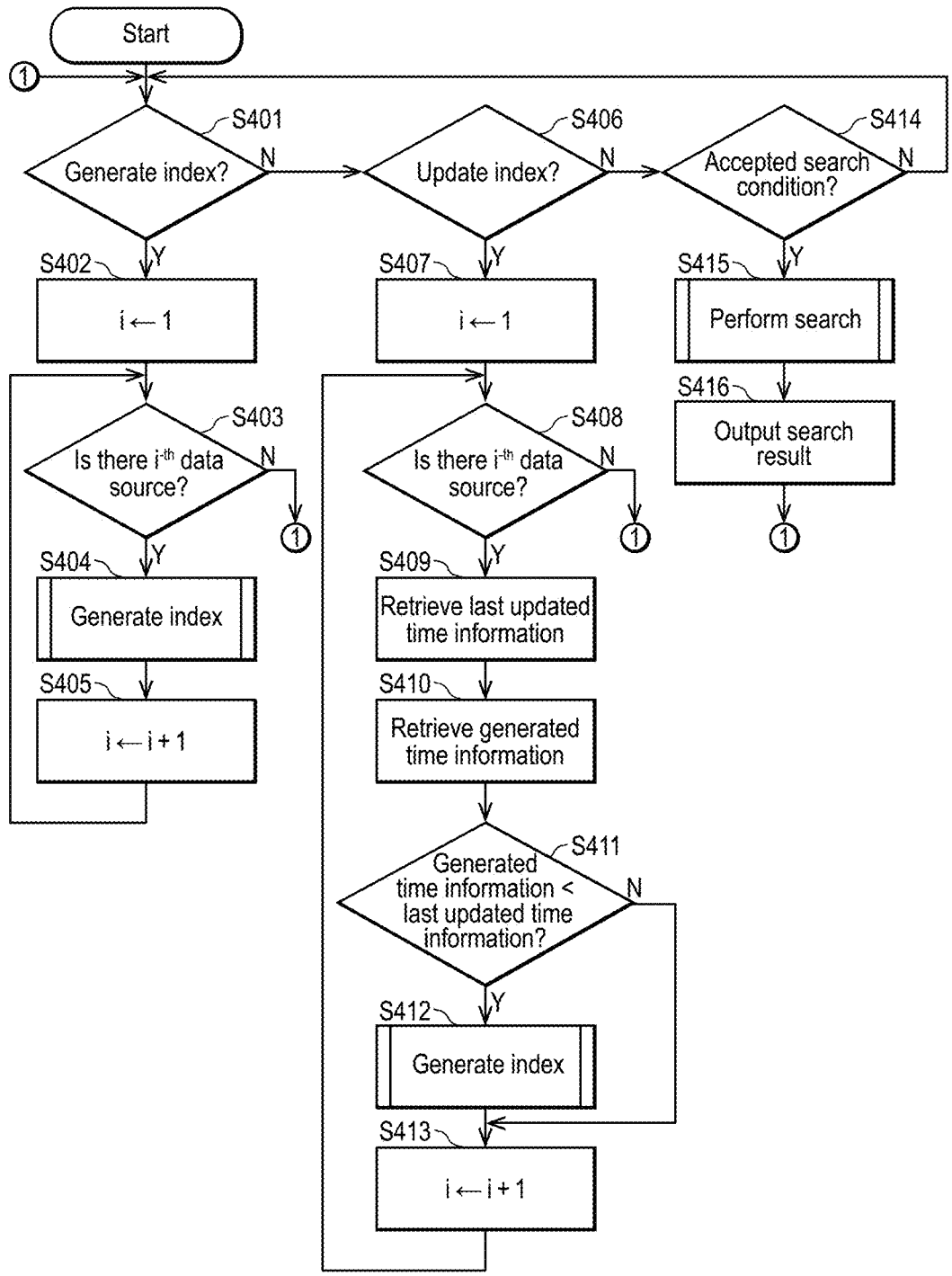
FIG. 4 is a flowchart illustrating an operation example of the search apparatus 1 in the embodiment.

In the flowchart in FIG. 4, the processing ends at power off or at an interruption of termination processing.

Next, an example of the index generating processing in step S404 will be described with reference to the flowchart in FIG. 5.

(Step S501) The source index generating unit 1315 generates a source index. Below, an example of the source index generating processing will be described with reference to the flowchart in FIG. 6.

(Step S502) The array label index generating unit 1312 generates an array label index. Below, an example of the array label index generating processing will be described with reference to the flowchart in FIG. 7.

(Step S503) The array index generating unit 1311 generates an array index. Below, an example of the array index generating processing will be described with reference to the flowchart in FIG. 8.

(Step S504) The record index generating unit 1313 generates a record index. Below, an example of the record index generating processing will be described with reference to the flowchart in FIG. 9.

(Step S505) The secondary index generating unit 1314 generates a secondary index. Below, an example of the secondary index generating processing will be described with reference to the flowchart in FIG. 10.

In the flowchart in FIG. 5, for example, the record index and the array index may be generated together for each record. That is to say, there is no limitation on the procedure, the order, and the like for generating various types of indexes.

Figure 6:
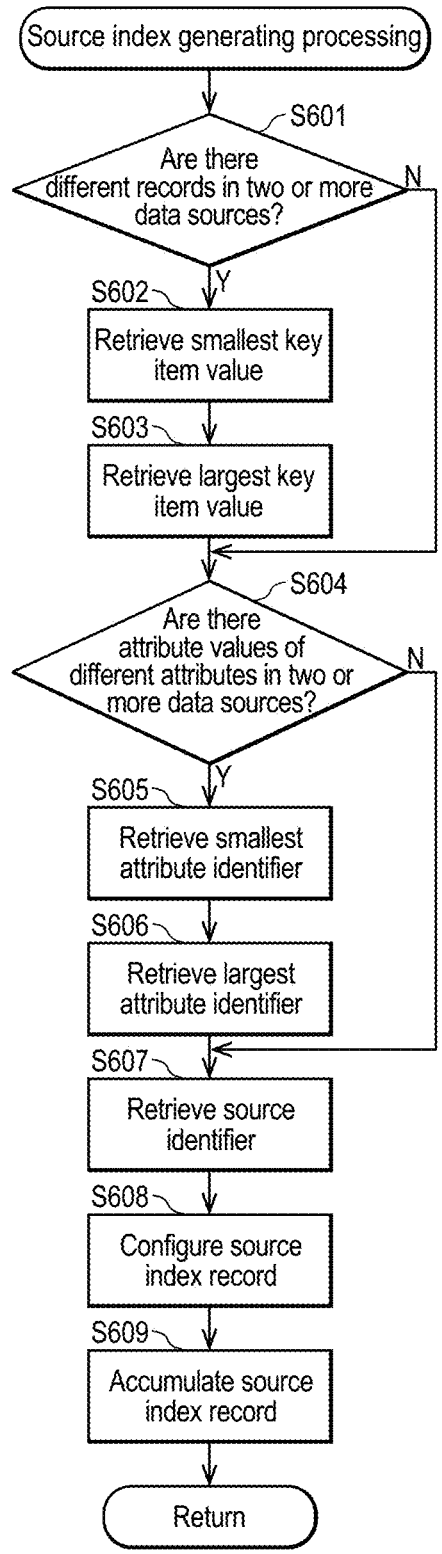
FIG. 6 is a flowchart illustrating of an example of source index generating processing in the embodiment.

Next, an example of the source index generating processing in step S501 will be described with reference to the flowchart in FIG. 6.

(Step S601) The source index generating unit 1315 determines whether or not there are different records in each of two or more data sources. If there are different records, the procedure advances to step S602, or otherwise, the procedure advances to step S604.

(Step S602) The source index generating unit 1315 refers to a data source for which an index is to be generated, and retrieves the smallest key item value of the data source.

(Step S603) The source index generating unit 1315 refers to the data source for which an index is to be generated, and retrieves the largest key item value of the data source.

(Step S604) The source index generating unit 1315 determines whether or not there are attribute values of different attributes in each of two or more data sources. If there are attribute values of different attributes, the procedure advances to step S605, or otherwise the procedure advances to step S607.

(Step S605) The source index generating unit 1315 refers to the data source for which an index is to be generated, and retrieves the smallest attribute identifier of the data source.

(Step S606) The source index generating unit 1315 refers to the data source for which an index is to be generated, and retrieves the largest attribute identifier of the data source.

(Step S607) The source index generating unit 1315 retrieves a source identifier of the data source for which an index is to be generated.

(Step S608) The source index generating unit 1315 configures a source index record. The source index record has, for example, the smallest key item value and the largest key item value. The source index record has, for example, the smallest attribute identifier and the largest attribute identifier. The source index record has, for example, the smallest key item value, the largest key item value, the smallest attribute identifier, and the largest attribute identifier. The source index record corresponds to a source identifier. It will be appreciated that the state of corresponding to a source identifier may be a state of having a source identifier.

(Step S609) The source index generating unit 1315 adds the source index record configured in step S608 to the source index storage unit 1125. The procedure returns to the upper-level processing.

Next, an example of the array label index generating processing in step S502 will be described with reference to the flowchart in FIG. 7.

(Step S701) The array label index generating unit 1312 substitutes 1 for a counter i.

(Step S702) The array label index generating unit 1312 retrieves an attribute identifier of an $i^{-th}$ attribute of the data source for which an index is to be generated.

For example, the array label index generating unit 1312 retrieves an attribute identifier of the $i^{-th}$ attribute or a record in the first row in the data source for which an index is to be generated. For example, the array label index generating unit 1312 may retrieve an attribute identifier of the $i^{-th}$ attribute from the data source schema information stored in the storage unit 11. The data source schema information is information for specifying the structure of a data source, and has, for example, two or more attribute identifiers.

(Step S703) The array label index generating unit 1312 determines whether or not an attribute identifier of the $i^{-th}$ attribute has been retrieved in step S702. If an attribute identifier has been retrieved, the procedure advances to step S704, or otherwise the procedure returns to the upper-level processing.

(Step S704) The array label index generating unit 1312 configures an array label index record having the attribute identifier of the $i^{-th}$ attribute retrieved in step S702 and i (attribute order information). The array label index record is information for configuring an array label index.

(Step S705) The array label index generating unit 1312 adds the array label index record configured in step S704, in association with the data source for which an index is to be generated, in the array label index storage unit 1122.

(Step S706) The array label index generating unit 1312 increments the counter i by 1. The procedure returns to step S702.

Figure 7:
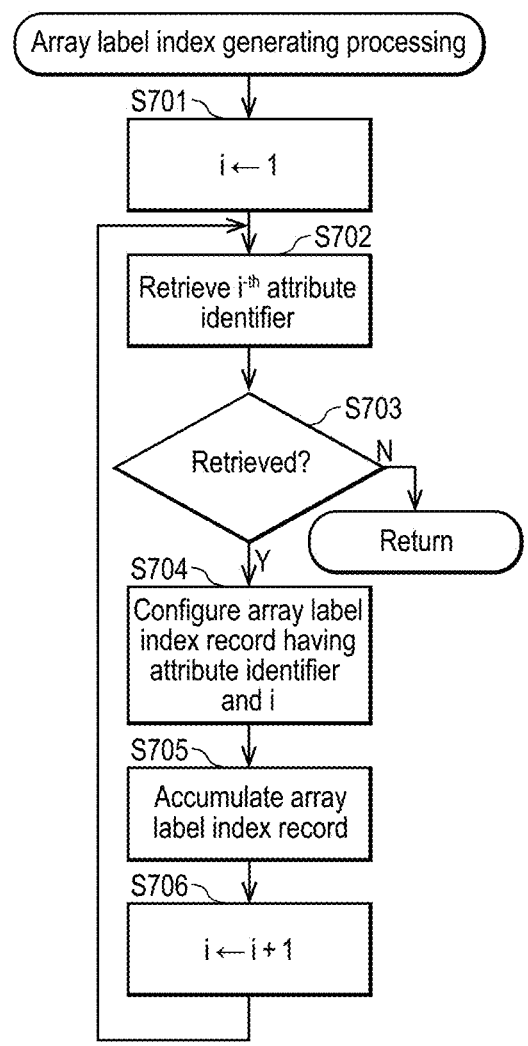
FIG. 7 is a flowchart illustrating of an example of array label index generating processing in the embodiment.

In the flowchart in FIG. 7, it is preferable to sort the array label index records are sorted using the attribute identifiers as a key, and configure an array label index.

Figure 8:
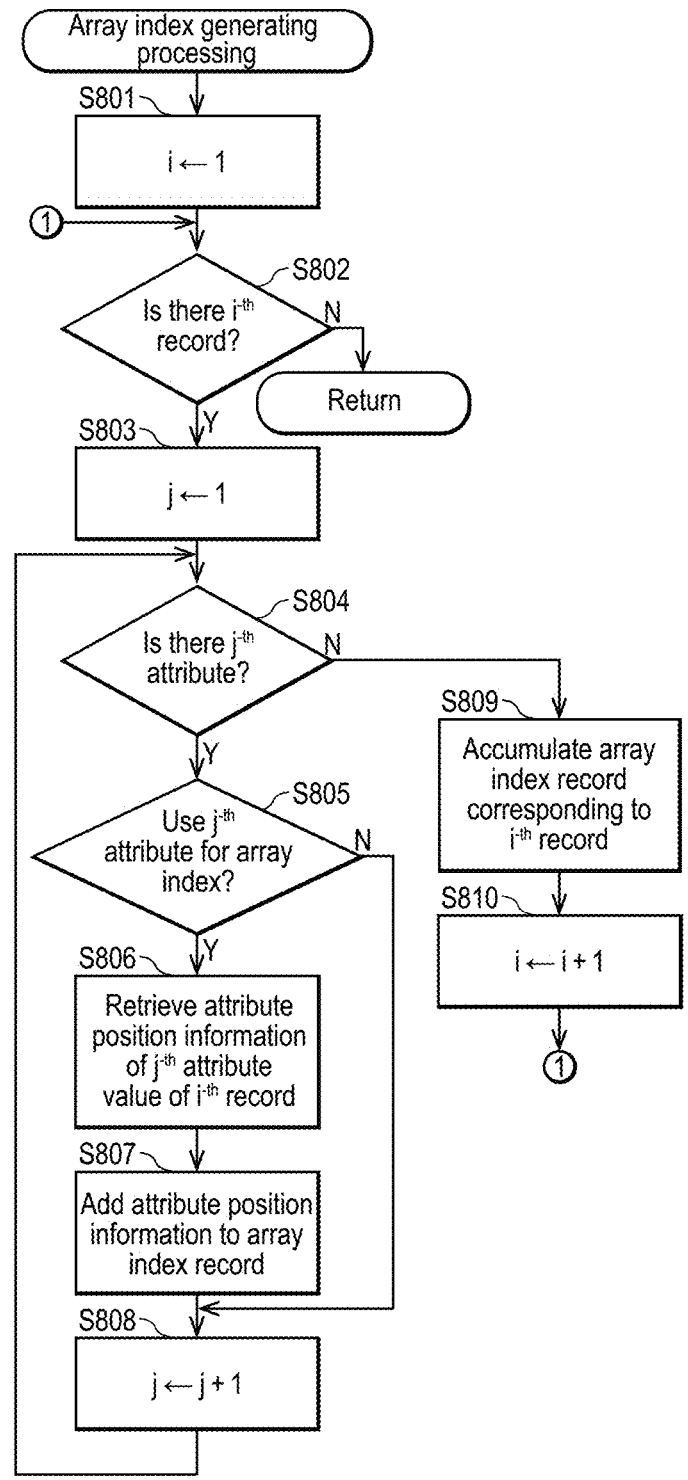
FIG. 8 is a flowchart illustrating of an example of array index generating processing in the embodiment.

Next, an example of the array index generating processing in step S503 will be described with reference to the flowchart in FIG. 8.

(Step S801) The array index generating unit 1311 substitutes 1 for a counter i.

(Step S802) The array index generating unit 1311 determines whether or not there is an $i^{-th}$ record in the data source for which an index is to be generated. If there is an $i^{-th}$ record, the procedure advances to step S803, or otherwise the procedure returns to the upper-level processing.

(Step S803) The array index generating unit 1311 substitutes 1 for a counter j.

(Step S804) The array index generating unit 1311 determines whether or not there is a $j^{-th}$ attribute in the data source for which an index is to be generated. If there is a $j^{-th}$ attribute, the procedure advances to step S805, or otherwise the procedure advances to step S809.

(Step S805) The array index generating unit 1311 determines whether or not to use the $j^{-th}$ attribute for the array index. If the $j^{-th}$ attribute is to be used for the array index, the procedure advances to step S806, or otherwise the procedure advances to step S808.

(Step S806) The array index generating unit 1311 retrieves attribute position information of the attribute value of the $j^{-th}$ attribute of the $i^{-th}$ record, from the data source for which an index is to be generated.

(Step S807) The array index generating unit 1311 adds the attribute position information retrieved in step S806 to the buffer of the array index record.

(Step S808) The array index generating unit 1311 increments the counter j by 1. The procedure returns to step S804.

(Step S809) The array index generating unit 1311 adds the array index record in the buffer of the array index record to the array index storage unit 1121.

(Step S810) The array index generating unit 1311 increments the counter i by 1. The procedure returns to step S802.

Next, an example of the record index generating processing in step S504 will be described with reference to the flowchart in FIG. 9.

(Step S901) The record index generating unit 1313 substitutes 1 for a counter i.

(Step S902) The record index generating unit 1313 determines whether or not there is an $i^{-th}$ record in the data source for which an index is to be generated. If there is an $i^{-th}$ record, the procedure advances to step S903, or otherwise the procedure returns to the upper-level processing.

(Step S903) The record index generating unit 1313 refers to the data source for which an index is to be generated, and retrieves record position information of the $i^{-th}$ record.

(Step S904) The record index generating unit 1313 refers to the data source for which an index is to be generated, and retrieves a key item value of the $i^{-th}$ record.

(Step S905) The record index generating unit 1313 retrieves record index record position information, which is position information in the record index, of the $i^{-th}$ record index record.

(Step S906) The record index generating unit 1313 configures an $i^{-th}$ record index record having the record position information retrieved in step S903, the key item value retrieved in step S904, and the record index record position information retrieved in step S905.

(Step S907) The record index generating unit 1313 adds the record index record configured in step S906 to the record index storage unit 1123.

(Step S908) The record index generating unit 1313 increments the counter i by 1. The procedure returns to step 902.

Figure 9:
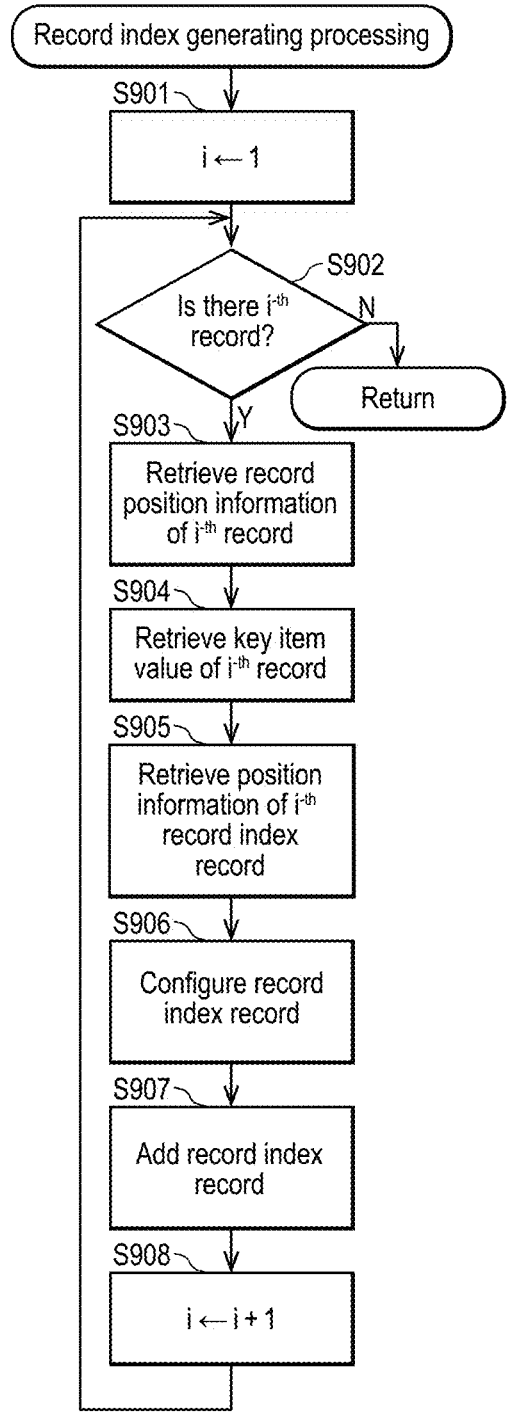
FIG. 9 is a flowchart illustrating of an example of record index generating processing in the embodiment.

It is preferable that, in the flowchart in FIG. 9, the record index generating unit 1313 sorts the record index records using the key item values as a key. In this case, it will be appreciated that the record index generating unit 1313 retrieves record index record position information in a sorted state for each record index record.

Next, an example of the secondary index generating processing in step S505 will be described with reference to the flowchart in FIG. 10.

(Step S1001) The secondary index generating unit 1314 substitutes 1 for a counter i.

(Step S1002) The secondary index generating unit 1314 determines whether or not there is an $i^{-th}$ record index record in the record index. If there is an $i^{-th}$ record index record, the procedure advances to step S1003, or otherwise the procedure returns to the upper-level processing.

(Step S1003) The secondary index generating unit 1314 determines whether or not to use the $i^{-th}$ record index record for the secondary index. If the record is to be used for the secondary index, the procedure advances to step S1004, or otherwise the procedure advances to step S1006.

The secondary index generating unit 1314 uses some record index records out of all record index records. For example, the secondary index generating unit 1314 determines to use a record index record corresponding to the number in which, when the total number of record index records is divided by N (N is a natural number of 2 or more), the remainder is M (M is an integer, 0≤M<N−1). For example, the secondary index generating unit 1314 determines to use predetermined some record index records.

(Step S1004) The secondary index generating unit 1314 retrieves a key item value and record index record position information from the $i^{-th}$ record index record, and configures a secondary index record having the information.

(Step S1005) The secondary index generating unit 1314 adds the secondary index record configured in step S1004 to the secondary index storage unit 1124.

(Step S1006) The secondary index generating unit 1314 increments the counter i by 1. The procedure returns to step 1002.

Figure 10:
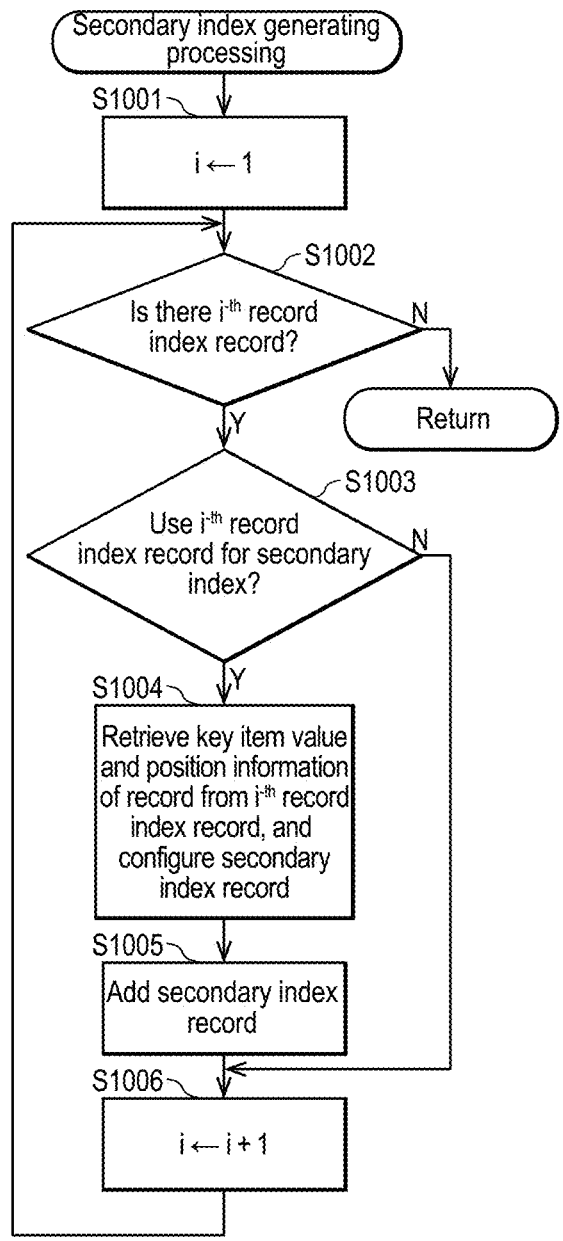
FIG. 10 is a flowchart illustrating of an example of secondary index generating processing in the embodiment.

It is preferable that, in the flowchart in FIG. 10, the secondary index records are sorted using the key item values as a key.

Figure 11:
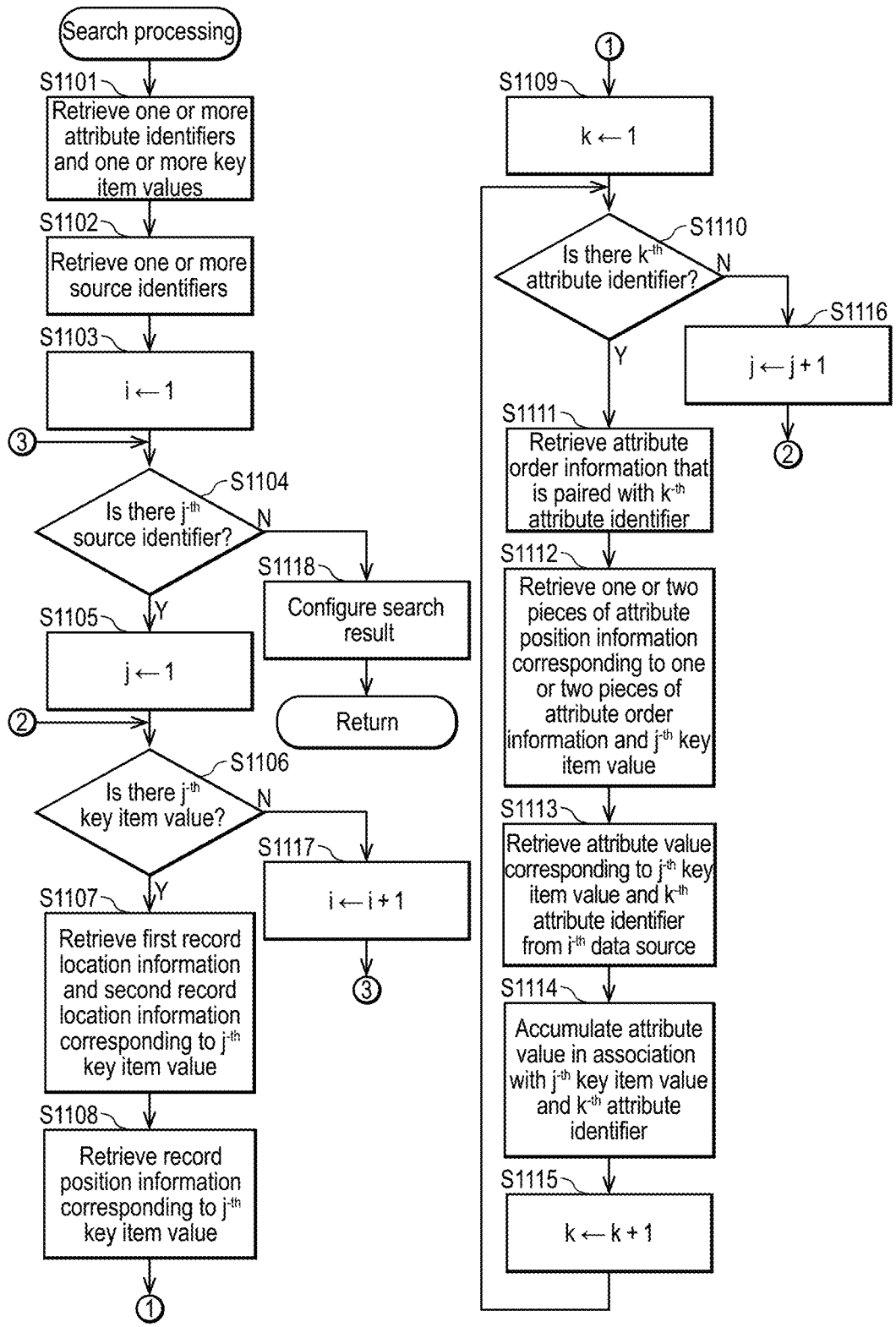
FIG. 11 is a flowchart illustrating of an example of search processing in the embodiment.

Next, an example of the search processing in step S415 will be described with reference to the flowchart in FIG. 11.

(Step S1101) The search unit 132 retrieves one or more attribute identifiers and one or more key item values corresponding to the accepted search condition. The one or more attribute identifiers are information for specifying an attribute value that is to be retrieved as a search result. The one or more key item values are information for specifying a record from which information is to be retrieved as a search result. That is to say, the search unit 132 retrieves attribute values included in records of the retrieved one or more key item values and identified with the retrieved one or more attribute identifiers.

(Step S1102) The search unit 132 refers to source indexes, and retrieves one or more source identifiers corresponding to the one or more attribute identifiers and one or more key item values retrieved in step S1101. The search unit 132 associates the retrieved one or more source identifiers with one or more attribute identifiers of attribute values included in data sources identified with the source identifiers and one or more key item values of records included in data sources identified with the source identifiers.

(Step S1103) The search unit 132 substitutes 1 for a counter i.

(Step S1104) The search unit 132 determines whether or not there is an $i^{-th}$ source identifier in the one or more source identifiers retrieved in step S1102. If there is an $i^{-th}$ source identifier, the procedure advances to step S1105, or otherwise the procedure advances to step S1118.

(Step S1105) The search unit 132 substitutes 1 for a counter j.

(Step S1106) The search unit 132 determines whether or not there is a $j^{-th}$ key item value in the one or more key item values associated with the $i^{-th}$ source identifier in step S1102. If there is a $j^{-th}$ key item value, the procedure advances to step S1107, or otherwise the procedure advances to step S1117.

(Step S1107) The search unit 132 refers to the secondary index corresponding to the $i^{-th}$ source identifier, and retrieves first record index record position information and second record index record position information corresponding to the $j^{-th}$ key item value. The first record index record position information is record index record position information that is paired with the key item value that is the largest among the key item values that are smaller than the $j^{-th}$ key item value. The second record index record position information is record index record position information that is paired with the key item value that is the smallest among the key item values that are larger than the $j^{-th}$ key item value. The search unit 132 may retrieve one piece of record index record position information that is paired with the $j^{-th}$ key item value from the secondary index.

(Step S1108) In the case in which first record index record position information and second record index record position information are retrieved in step S1107, the search unit 132 searches for a record index record between the first record index record position information and the second record index record position information (e.g., through binary search or sequential search), and detects the $j^{-th}$ key item value. Next, the search unit 132 retrieves record position information that is paired with the $j^{-th}$ key item value from the record index.

Furthermore, in the case in which one piece of record index record position information is retrieved in step S1107, the search unit 132 retrieves record position information that is paired with the record index record position information from the record index.

(Step S1109) The search unit 132 substitutes 1 for a counter k.

(Step S1110) The search unit 132 determines whether or not there is a $k^{-th}$ attribute identifier corresponding to the $i^{-th}$ source identifier. If there is a $k^{-th}$ attribute identifier, the procedure advances to step S1111, or otherwise the procedure advances to step S1116.

(Step S1111) The search unit 132 refers to the array label index corresponding to the $i^{-th}$ source identifier, and retrieves attribute order information that is paired with the $k^{-th}$ attribute identifier from the array label indexes.

(Step S1112) The search unit 132 refers to the array index corresponding to the $i^{-th}$ source identifier, determines whether or not there is attribute order information that matches the attribute order information retrieved in step S1111, in the array index. If there is attribute order information that matches the attribute order information, the search unit 132 retrieves attribute position information that is paired with the attribute order information and is paired with the $j^{-th}$ key item value, from the array index.

If there is no attribute order information that matches the attribute order information, the search unit 132 retrieves two pieces of attribute order information between which the attribute order information is located. That is to say, the search unit 132 retrieves first attribute order information, which is attribute order information with a value smaller than that of the attribute order information and has the smallest difference from the attribute order information. The search unit 132 retrieves second attribute order information, which is attribute order information with a value larger than that of the attribute order information and has the smallest difference from the attribute order information. The first attribute order information and the second attribute order information are pieces of information between which the attribute order information is located. Next, the search unit 132 retrieves attribute position information that is paired with the first attribute order information and is paired with the $j^{-th}$ key item value, from the array index. The search unit 132 retrieves attribute position information that is paired with the second attribute order information and is paired with the $j^{-th}$ key item value, from the array index.

(Step S1113) In the case in which one piece of attribute position information is retrieved in step S1112, the search unit 132 retrieves an attribute value at the position indicated by the one piece of attribute position information retrieved in step S1112, from the record at the position indicated by the record position information that is paired with the $j^{-th}$ key item value retrieved in step S1108, from the data source identified with the $i^{-th}$ source identifier.

Furthermore, in the case in which two pieces of attribute position information are retrieved in step S1112, the search unit 132 inspects an attribute value at a position specified with each of the two pieces of attribute position information, from the record at the position indicated by the record position information that is paired with the $j^{-th}$ key item value retrieved in step S1108, for example, through sequential search, and retrieves an attribute value located at the order of attribute order information that is paired with the $k^{-th}$ attribute identifier, from the data source identified with the $i^{-th}$ source identifier.

(Step S1114) The search unit 132 temporarily accumulates the attribute value retrieved in step S1113, in an unshown buffer, in association with the $j^{-th}$ key item value and the $k^{-th}$ attribute identifier.

(Step S1115) The search unit 132 increments the counter k by 1. The procedure returns to step 1110.

(Step S1116) The search unit 132 increments the counter j by 1. The procedure returns to step 1106.

(Step S1117) The search unit 132 increments the counter i by 1. The procedure returns to step 1104.

(Step S1118) The search unit 132 configures a search result including the one or more attribute values temporarily accumulated in the unshown buffer. The procedure returns to the upper-level processing. There is no limitation on the method for configuring a search result. It is preferable that an attribute identifier corresponding to an attribute value included in the search result is included in the search result such that it is clearly seen the attribute identifier corresponds to the attribute value. It is preferable that the search result includes the $j^{-th}$ key item value.

Next, an operation example of the data source management apparatus 2 will be described. The data source management apparatus 2 reads data source in the data source storage unit 111 in response to access from the search apparatus 1, and transmits it to the search apparatus 1. In this case, the data source management apparatus 2 may read and transmit only part of a data source.

Next, an operation example of the terminal apparatus 3 will be described. The terminal accepting unit 32 of the terminal apparatus 3 accepts a search condition. Next, the terminal processing unit 33 configures a search condition that is to be transmitted. Next, the terminal transmitting unit 34 transmits the search condition to the search apparatus 1. Then, in response to transmission of the search condition, the terminal receiving unit 35 receives a search result. Next, the terminal processing unit 33 configures a search result that is to be output, using the received search result. Next, the terminal output unit 36 outputs the search result.

Hereinafter, a specific operation example of the search system A in this embodiment will be described.

Figure 12:
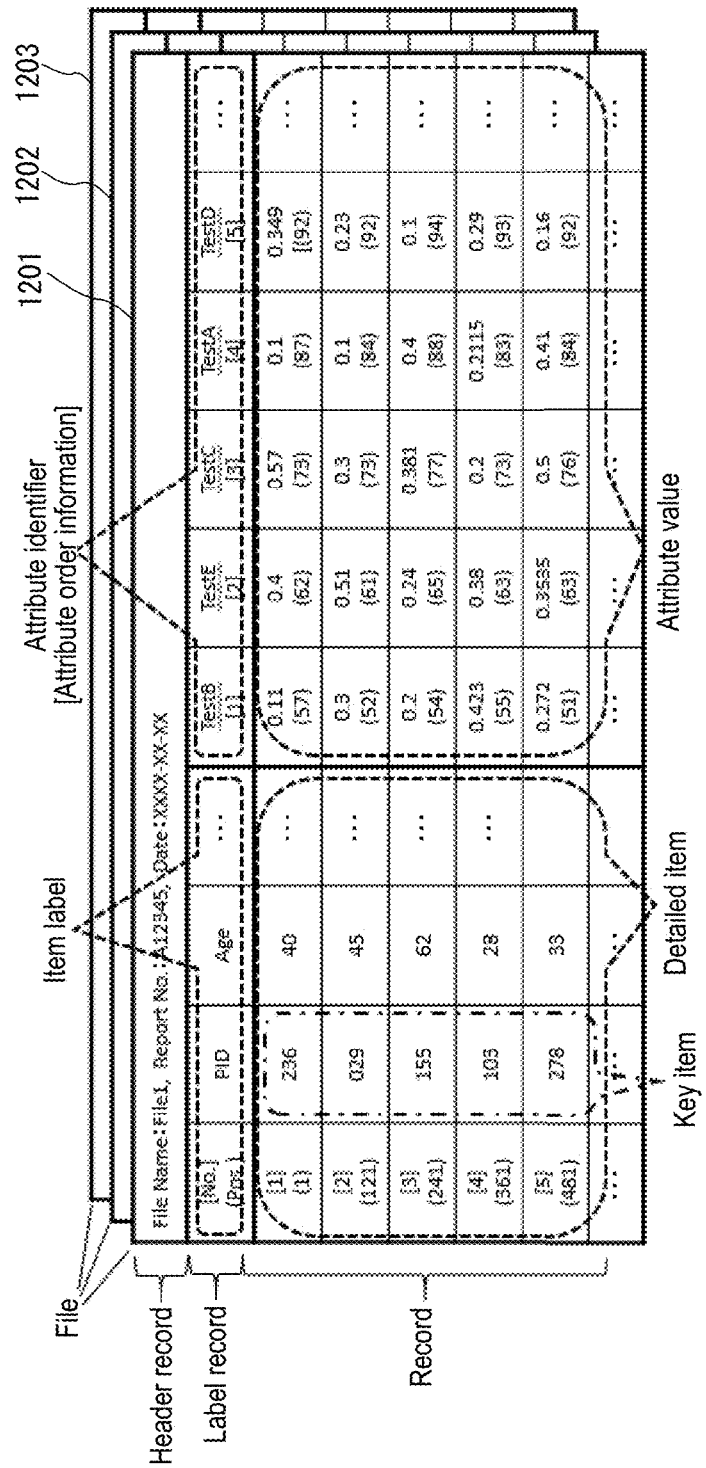
FIG. 12 is a diagram showing an example of a data source in the embodiment.

It is assumed that three or more data sources including three data sources (1201, 1202, and 1203) shown in FIG. 12 are stored in the data source storage unit 111 of the search apparatus 1 or the data source storage unit 111 of the data source management apparatus 2. It is assumed that each of the three data sources is in the form of one file.

Each data source in FIG. 12 has a header record, a label record, and a large number of records. The label record and each of the records are defined by a first delimiter. The first delimiter in this example is, for example, a return code.

The header record is a so-called header of a file, and has one or more source attribute values. The source attribute values in this example are each a source identifier, a report No., and last updated time information. The source identifier in FIG. 12 is a File Name, and has a value of "File 1". The report No. is a number for identifying a source from which the data source is obtained, and has a value of "A12345". The last updated time information in FIG. 12 is Date, and has a value of "XXXX-XX-XX".

The label record is, for example, the first row of a file. If the header record is the first row of a file, the label record is the second row of the file. The label record is a group of item labels and a group of attribute identifier. The item label are each a label of a key item or a label of a detailed item. The key item is an attribute functioning as a key of a record, and is "PID (personal ID)" in this example. "PID" is an ID for identifying a user. The detailed item is an attribute value of a user corresponding to "PID", and the detailed item in this example includes "No." and "Age". "No." is a record ID, and has a value of [1], [2], [3], or the like in 1201 of FIG. 12. (Pos.) below "No." is record position information of each record (an offset of the beginning of the record in the data source, in this example). "Age" is the age of a user. The attribute identifier in FIG. 12 is "Test B", "Test E", "Test C", or the like. In FIG. 12, the attribute order information is shown below the attribute identifier. The attribute order information is [1], [2], [3], or the like below the attribute identifier.

Each record in FIG. 12 has a key item value, a detailed item value, and an attribute value. The key item value is a value of a key item, and a PID (e.g., 236, 029) of each user in this example. Which value is to be taken as a key item value is preferably such that the value can be designated as a parameter for generating an index, and the value may be another value (e.g., "Age", or "a combination of PID and Age") or also may have two or more key item values. The detailed item value in this example is, for example, a value of "No." or a value of "Age". The value of "No." in this example is [1], [2], or the like. The values (e.g., (1), (121), (241), etc.) shown below "No." ([1], [2], [3], etc.) are record position information of each record.

The record corresponding to the record identifier [1] has an attribute value of 0.11, 0.4, 0.57, or the like. In FIG. 12, attribute value position information ((57), (62), (73), etc.) of each attribute value is shown below attribute value (0.11, 0.4, 0.57, etc.).

It is assumed that the data source in this example includes a group of genetic/genomic information. The data dealing with general genetic/genomic information contains data such as nucleic acid arrays of genes and amino acid arrays of proteins and may have a length of one record of, for example, several GBs. The number of attribute values included in one record can be huge, and the data size is often huge. In many cases, data dealing with genetic/genomic information is stored and distributed in flat files (general text files) in a relatively simple layout, and a data source in this specific example (see FIG. 12) is an example thereof.

In this situation, the following three specific examples will be described. Specific Example 1 is an example of the index generating processing. Specific Example 2 is an example of the search processing in the case in which a source index has a combination of the smallest key item value and the largest key item value but does not have a combination of the smallest attribute identifier and the largest attribute identifier. Specific Example 3 is an example of the search processing in the case in which a source index has a combination of the smallest key item value, the largest key item value, the smallest attribute identifier, and the largest attribute identifier.

Specific Example 1

Hereinafter, an example of the processing in which the index generating unit 131 of the search apparatus 1 generates various types of indexes will be described with reference to FIG. 13. It is assumed that the key item in this example is "PID".

(1) Source Index Generating Processing

The source index generating unit 1315 accesses the file "data source 1301", and retrieves a source identifier (a file name, in this example) "file 1" of the data source 1301. The source index generating unit 1315 opens the data source 1301. Next, the source index generating unit 1315 retrieves the smallest key item value "029", which is a PID that is the smallest among the PIDs in the data source 1301, and the largest key item value "451", which is a PID that is the largest thereamong. In the data source 1301, in the case in which the PIDs are sorted, the source index generating unit 1315 retrieves the first PID and the last PID. In the case in which the PIDs are not sorted, the source index generating unit 1315 sequentially inspects the PIDs, and retrieves the smallest key item value and the largest key item value from the data source 1301.

Furthermore, the source index generating unit 1315 retrieves the smallest attribute identifier "Test A" and the largest attribute identifier "Test E" from among the attribute value identifiers of the label record in the data source 1301. In the data source 1301, in the case in which the attribute identifier are sorted, the source index generating unit 1315 retrieves the first attribute identifier and the last attribute identifier from the label record. In the case in which the attribute identifier are not sorted, the source index generating unit 1315 sequentially inspects the attribute identifiers, and retrieves the smallest attribute identifier and the largest attribute identifier from the label record.

Next, the source index generating unit 1315 configures a source index record "file 1, 029, 451, Test A, Test E" from the retrieved source identifier, smallest key item value, largest key item value, smallest attribute identifier, and largest attribute identifier, and accumulates it in the source index storage unit 1125.

The source index generating unit 1315 configures a source index record in a similar manner also for other data sources (the files "file 2", "file 3", etc.), and accumulates it in the source index storage unit 1125.

Figure 13:
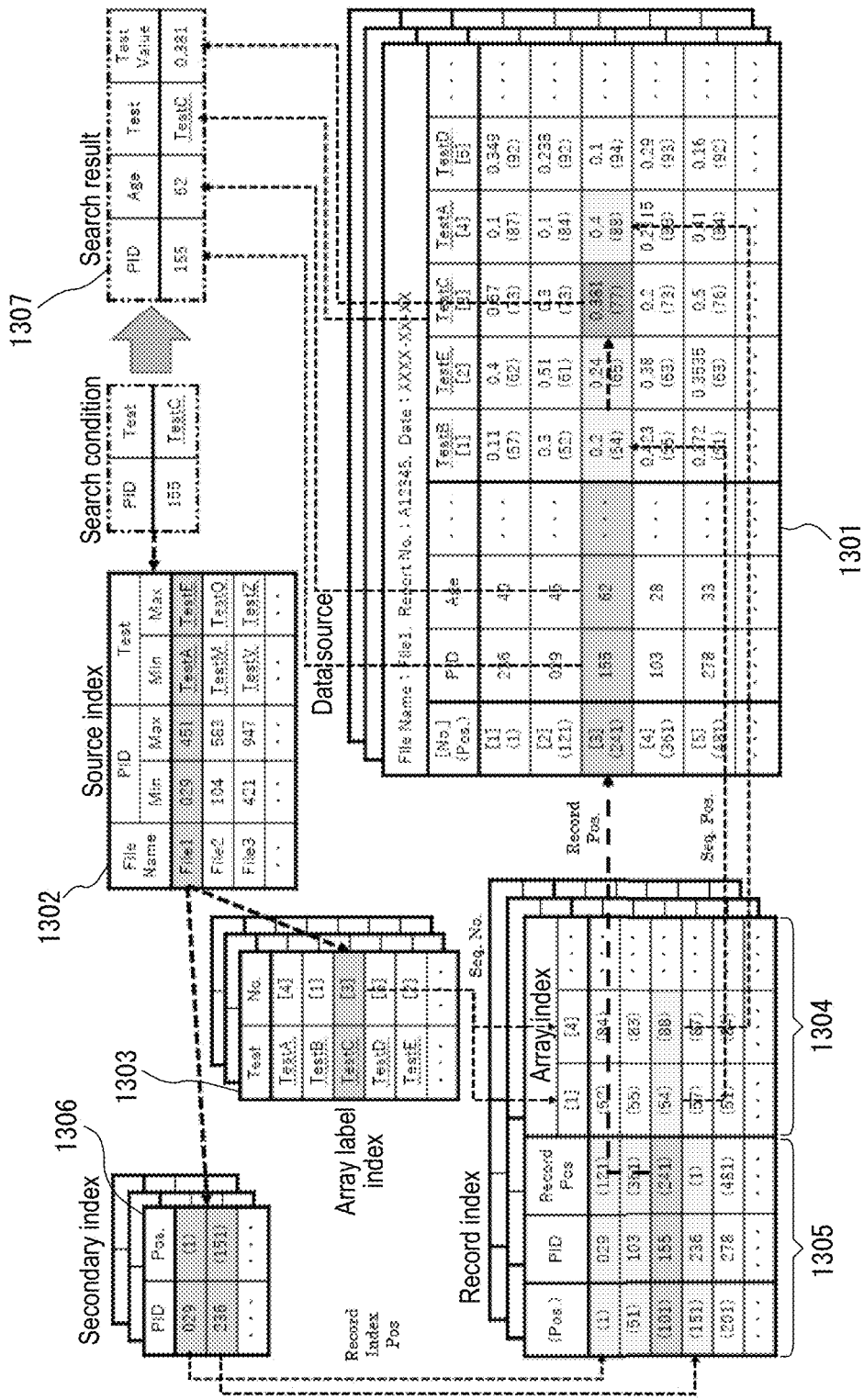
FIG. 13 is a diagram illustrating an example of index generating processing and an example of search processing in the embodiment.

Through the above-described processing, the source index 1302 in FIG. 13 is accumulated in the source index storage unit 1125.

(2) Array Label Index Generating Processing

The array label index generating unit 1312 accesses the file "data source 1301", and retrieves a source identifier (file name) "file 1" of the data source 1301. The source index generating unit 1315 opens the data source 1301.

Next, the array label index generating unit 1312 retrieves attribute identifiers together with attribute order information indicating the order thereof, in the order in which the attribute identifiers are arranged in the label index of the data source 1301. Then, an array label index record, which is a combination of an attribute identifier and attribute order information is configured for each attribute identifier.

Next, the array label index generating unit 1312 sorts the array label index records, for example, in the ascending order using the attribute identifiers as a key. Then, the array label index generating unit 1312 accumulates the sorted array label index records in the array label index storage unit 1122.

The array label index generating unit 1312 configures an array label index in a similar manner also for other data sources (the files "file 2", "file 3", etc.), and accumulates it in the array label index storage unit 1122.

Through the above-described processing, the array label index 1303 in FIG. 13 is accumulated in the array label index storage unit 1122.

(3) Array Index Generating Processing

The array index generating unit 1311 accesses the file "data source 1301", and retrieves a source identifier (file name) "file 1" of the data source 1301. The source index generating unit 1315 opens the data source 1301.

For example, the array index generating unit 1311 retrieves attribute order information of the data source 1301 at every predetermined number of values (at every three values, in this example), such as the $1^{-st}$ value, the $4^{-th}$ value, and the $7^{-th}$ value. For example, the array index generating unit 1311 detects a second delimiter for each record, advances a file pointer to an attribute value at the order of the retrieved attribute order information, and, for example, retrieves attribute position information, which is an offset of the attribute value at the order in the record. Next, for each record in the data source 1301, the array index generating unit 1311 links the retrieved attribute position information in the order indicated by the attribute order information in association with the PID of the record, and configures an array index record.

Next, for example, the array index generating unit 1311 sorts the array index records, for example, in the ascending order using the corresponding PIDs as a key, configures an array index, and accumulates it in the array index storage unit 1121.

Furthermore, the array index generating unit 1311 configures an array index in a similar manner also for other data sources (the files "file 2", "file 3", etc.), and accumulates it in the array index storage unit 1121.

Through the above-described processing, the array index 1304 in FIG. 13 is accumulated in the array index storage unit 1121.

(4) Record Index Generating Processing

The record index generating unit 1313 accesses the file "data source 1301", and retrieves a source identifier (file name) "file 1" of the data source 1301. The source index generating unit 1315 opens the data source 1301.

For each record in the data source 1301, the record index generating unit 1313 retrieves a key item value and record position information, which an offset of the record in the data source 1301 from the data source 1301, and configures a record index record.

Then, the record index generating unit 1313 sorts the combinations of a key item value and record position information, for example, in the ascending order using the key item values as a key. Next, the record index generating unit 1313 retrieves position information (Pos.) of each record index record in the record index. The position information (Pos.) is record index record position information.

It is preferable that the record index record position information (Pos.) is information (Pos.) of a record having a combination of a key item value and record position information of the position information (Pos.) and the array index record. That is to say, it is preferable that the record index record and the array index record are linked to each other for each record in a data source.

Next, the record index generating unit 1313 accumulates the record index record for each record in the data source 1301, in the record index storage unit 1123.

Furthermore, the record index generating unit 1313 configures a record index in a similar manner also for other data sources (the files "file 2", "file 3", etc.), and accumulates it in the record index storage unit 1123.

Through the above-described processing, the record index 1305 in FIG. 13 is accumulated in the record index storage unit 1123.

(5) Secondary Index Generating Processing

The secondary index generating unit 1314 reads a record index in the record index storage unit 1123.

Next, for example, the secondary index generating unit 1314 retrieves a secondary index record, which is a combination of a key item value (a PID, in this example) and record index record position information (Pos.) included in a record index record, at every predetermined number of records (at every three records, in this example), such as the $1^{st}$ record, the $4^{th}$ record, and the $7^{th}$ record.

Next, the secondary index generating unit 1314 adds the retrieved secondary index record to the secondary index storage unit 1124. In the secondary index, the secondary index records are sorted using the PIDs as a key.

Furthermore, the secondary index generating unit 1314 configures a secondary index in a similar manner also for other data sources (the files "file 2", "file 3", etc.), and accumulates it in the secondary index storage unit 1124.

Through the above-described processing, the secondary index 1306 in FIG. 13 is accumulated in the secondary index storage unit 1124.

Specific Example 2

Figure 14:
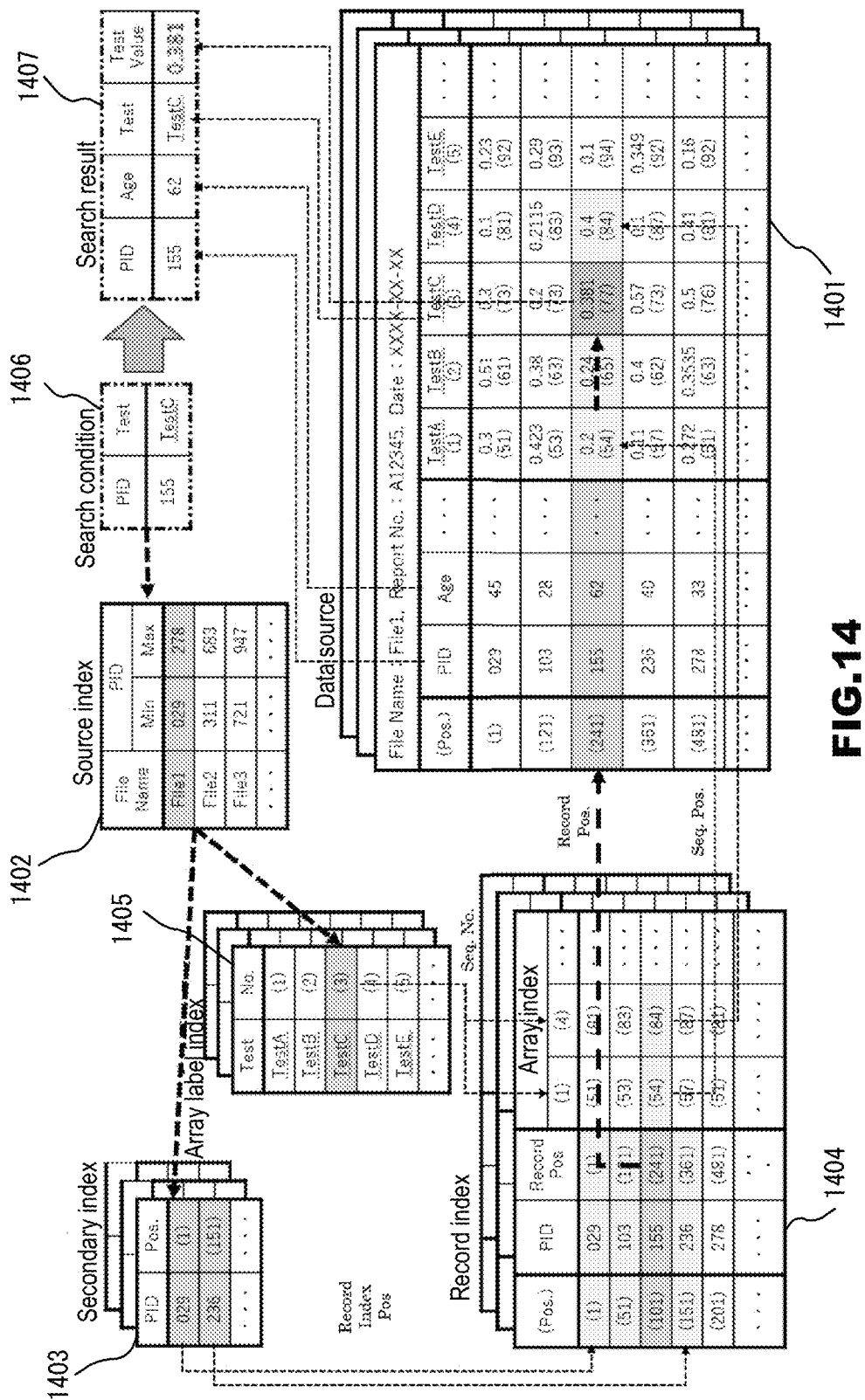
FIG. 14 is a diagram illustrating an example of search processing in the embodiment.

It is assumed that a data source 1401 in FIG. 14 is stored in the data source storage unit 111 of the data source management apparatus 2 or the data source storage unit 111 of the search apparatus 1.

In this case, it is assumed that a user inputs a search condition "Select PID, Age, Test, Test Value from data source where PID=155 AND Test=Test C" to the terminal apparatus 3. It is assumed that "Test" of "PID, Age, Test, Test Value" is an attribute value identifier, and "Test Value" is an attribute value.

Then, the terminal accepting unit 32 of the terminal apparatus 3 accepts this search condition. Next, the terminal processing unit 33 configures a search condition that is to be transmitted. Next, the terminal transmitting unit 34 transmits the search condition to the search apparatus 1.

Next, the condition accepting unit 121 of the search apparatus 1 receives the search condition "Select PID, Age, Test, Test Value from data source where PID=155 AND Test=Test C".

Next, the search unit 132 of the search apparatus 1 retrieves "PID", "Age", the attribute identifier "Test C", and the attribute value of Test C in the record corresponding to "PID=155 AND Test=Test C" as follows.

That is to say, first, the search unit 132 retrieves "PID=155" included in the search condition. The search unit 132 retrieves the attribute value identifier "Test C" included in the search condition (1406 in FIG. 14).

Next, the search unit 132 refers to the source index (1402), detects a source index record in which the retrieved "PID=155" is located between Min (smallest key item value) and Max (largest key item value), and retrieves a source identifier "File 1" included in the source index record.

Furthermore, the search unit 132 refers to the secondary index (1403) corresponding to the source identifier "File 1", detects PIDs "029" and "236" between which "PID=155" is located, and retrieves record index record position information (1) and (151) that are paired with the PIDs "029" and "236" from the secondary index (1403).

Next, the search unit 132 refers to the record index (1404) corresponding to the source identifier "File 1", and performs, for example, binary search in record index record position information (1) to (151), using "PID=155" as a key, thereby detecting a record index record including "PID=155". Then, the search unit 132 retrieves record position information (241) that is paired with "PID=155" from the record index record. The search unit 132 may detect a record index record including "PID=155" through not binary search but sequential search.

Next, the search unit 132 temporarily accumulates the retrieved record position information (241) and the record index record position information (101) in an unshown buffer.

Next, the search unit 132 refers to the array label index (1405) corresponding to the source identifier "File 1", performs binary search in the array label index, using the attribute identifier "Test C" included in the search condition as a key, thereby detecting an attribute identifier "Test C", and retrieves an attribute order information (3) that is paired with the attribute identifier "Test C". The search unit 132 may retrieve an attribute order information (3) through not binary search but sequential search.

Next, the search unit 132 refers to the array index corresponding to the source identifier "File 1", and retrieves first attribute order information (1) and second attribute order information (4) between which the attribute order information (3) is located, in the array index.

Next, the search unit 132 retrieves attribute value position information (54) corresponding to the record index record position information (101) and corresponding to the first attribute order information (1) in an unshown buffer, from the record index, and temporarily accumulates it in the unshown buffer. The search unit 132 retrieves attribute value position information (84) corresponding to the record index record position information (101) and corresponding to the second attribute order information (4) from the record index, and temporarily accumulates it in the unshown buffer.

Next, the search unit 132 accesses a data source identified with the source identifier "File 1", and opens the file.

Next, the search unit 132 retrieves the record position information (241), the attribute value position information (54), and the attribute value position information (84) from the unshown buffer, and retrieves an attribute value "0.381" located between the attribute value position information (54) and the attribute value position information (84) and corresponding to the attribute order information (3), in the record at the position specified with the record position information (241), from the file. The search unit 132 retrieves Age "62" in the record at the position specified with the record position information (241), from the file.

Then, the search unit 132 configures a search result having PID "155", Age "62", the attribute value identifier "Test C", and the attribute value "0.381".

Next, the result output unit 141 transmits the configured search result to the terminal apparatus 3. This search result is, for example, 1407 in FIG. 14.

Next, the terminal receiving unit 35 of the terminal apparatus 3 receives a search result. Next, the terminal processing unit 33 configures a search result that is to be output, using the received search result. Next, the terminal output unit 36 outputs the search result.

Specific Example 3

It is assumed that a data source 1301 in FIG. 13 is stored in the data source storage unit 111 of the data source management apparatus 2 or the data source storage unit 111 of the search apparatus 1.

In this case, it is assumed that a user inputs search condition "Select PID, Age, Test, Test Value from data source where PID=155 AND Test=Test C" to the terminal apparatus 3.

Then, the terminal accepting unit 32 of the terminal apparatus 3 accepts this search condition. Next, the terminal processing unit 33 configures a search condition that is to be transmitted. Next, the terminal transmitting unit 34 transmits the search condition to the search apparatus 1.

Next, the condition accepting unit 121 of the search apparatus 1 receives the search condition "Select PID, Age, Test, Test Value from data source where PID=155 AND Test=Test C".

Next, the search unit 132 of the search apparatus 1 retrieves "PID", "Age", the attribute identifier "Test C", and the attribute value of Test C in the record corresponding to "PID=155 AND Test=Test C" as follows.

That is to say, first, the search unit 132 retrieves "PID=155" included in the search condition. The search unit 132 retrieves the attribute value identifier "Test C" included in the search condition.

Next, the search unit 132 refers to the source index (1302), and retrieves a source identifier "File 1" corresponding to the retrieved "PID=155" and "Test C".

Subsequently, the search unit 132 obtains a search result through processing as described in Specific Example 2.

Next, the result output unit 141 transmits the configured search result to the terminal apparatus 3. This search result is, for example, 1307 in FIG. 13.

Next, in response to transmission of the search condition, the terminal receiving unit 35 receives a search result. Next, the terminal processing unit 33 configures a search result that is to be output, using the received search result. Next, the terminal output unit 36 outputs the search result.

As described above, according to this embodiment, it is possible to search for a desired attribute value at high speed from a data source with a large data size.

Furthermore, according to this embodiment, in particular, it is possible to search for a desired attribute value at high speed from a data source in which one record is very long.

Furthermore, according to this embodiment, it is possible to automatically generate an index for searching for information at high speed.

Furthermore, according to this embodiment, in particular, it is possible to automatically generate an index for searching for information at high speed from a data source in which one record is very long.

Moreover, according to this embodiment, it is possible to keep an index in the latest state.

The processing in this embodiment may be realized by software. The software may be distributed by software downloads or the like. Furthermore, the software may be distributed in a form where the software is stored in a storage medium such as a CD-ROM. The same applies to other embodiments in this specification. The software that realizes the search apparatus 1 in this embodiment is the following sort of program. Specifically, this program is a program for causing a computer capable of accessing: a data source storage unit in which a data source including two or more records having a key item value and two or more attribute values is stored; and an array index storage unit in which an array index having attribute position information for specifying a position at which an attribute value is located is stored for each of one or more records out of two or more records and for each of one or more attributes of each record, to function as: a condition accepting unit that accepts a search condition including an attribute identifier; a search unit that retrieves attribute position information corresponding to the attribute identifier included in the search condition, from the array index, and retrieves an attribute value corresponding to the attribute identifier included in the search condition, using the attribute position information, from the data source; and a result output unit that outputs a search result including the attribute value retrieved by the search unit.

Embodiment 2

In this embodiment, a search system including a search apparatus will be described that retrieves information from two or more data sources using a data dictionary having a three-layered schema structure, integrates the information, and outputs the integrated information.

Figure 15:
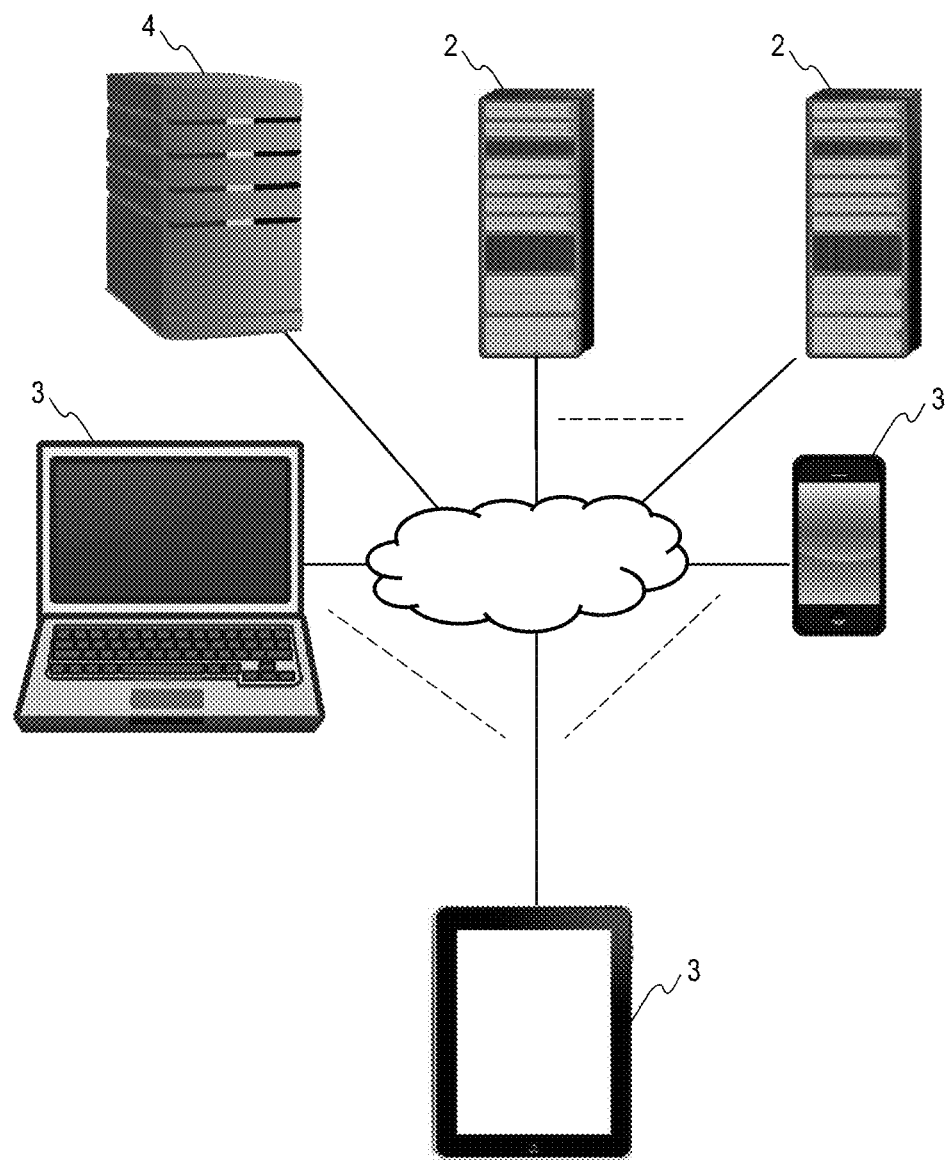
FIG. 15 is a conceptual diagram of a search system B in Embodiment 2.

FIG. 15 is a conceptual diagram of a search system B in this embodiment. The search system B includes a search apparatus 4, one or at least two data source management apparatuses 2, and one or at least two terminal apparatuses 3.

The search apparatus 4 is an apparatus that searches a data source for information. The search apparatus 4 is, for example, a so-called server such as a cloud server, an ASP server, or the like. There is no limitation on the type of the search apparatus 4.

The one or at least two data source management apparatuses 2 are typically apparatuses different from the search apparatus 4.

Moreover, the search apparatus 4 and the one or more data source management apparatuses 2 can communicate with each other through a network such as the Internet or a LAN. The search apparatus 4 and the terminal apparatuses 3 can communicate with each other through a network such as the Internet or a LAN.

Figure 16:
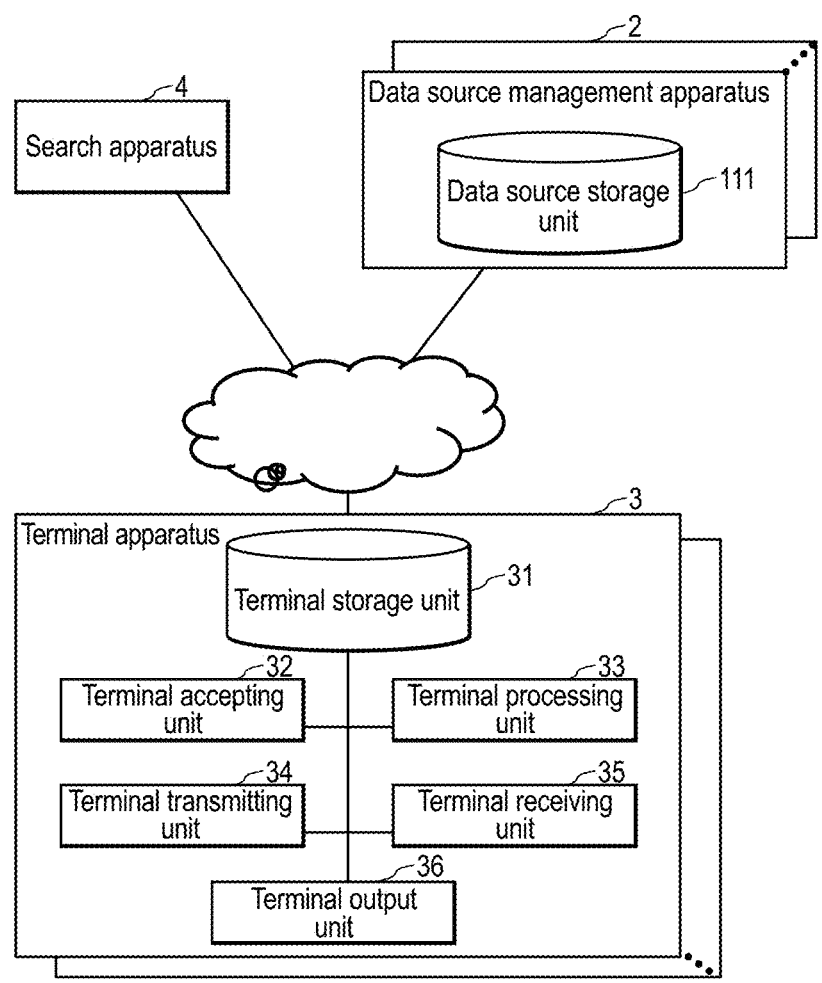
FIG. 16 is a block diagram of the search system B in the embodiment.
Figure 17:
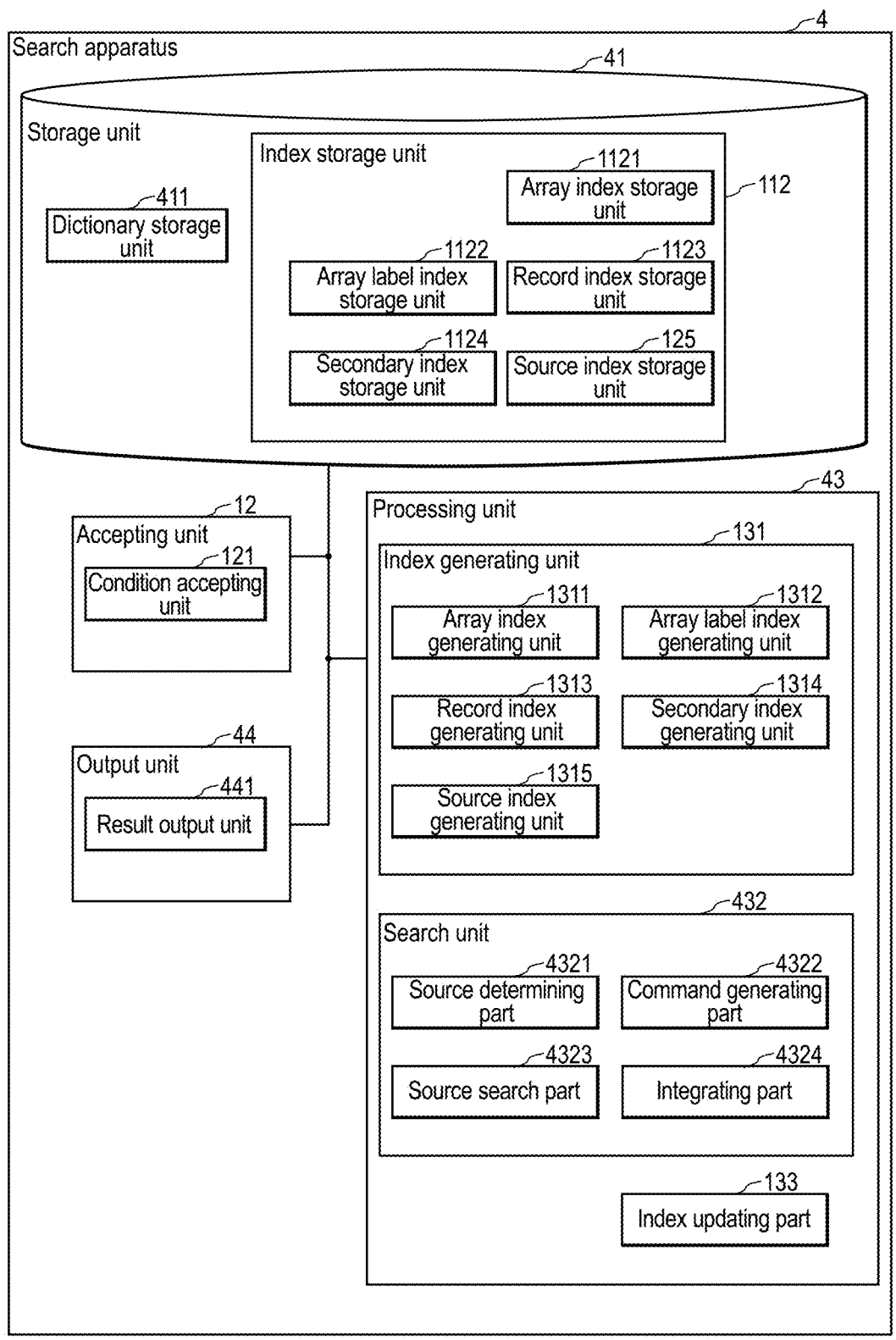
FIG. 17 is a block diagram of the search apparatus 4 in the embodiment.

FIG. 16 is a block diagram of the search system B in this embodiment. FIG. 17 is a block diagram of the search apparatus 4.

The search apparatus 4 includes a storage unit 41, an accepting unit 12, a processing unit 43, and an output unit 44. The storage unit 41 includes an index storage unit 112 and a dictionary storage unit 411. The processing unit 43 includes an index generating unit 131, a search unit 432, and an index updating unit 133. The search unit 432 include a source determining part 4321, a command generating part 4322, a source search part 4323, and an integrating part 4324. The output unit 44 includes a result output unit 441.

A data source in the data source storage unit 111 constituting the data source management apparatus 2 has one or at least two tables. A data source may be constituted by one file or two or more files. Each table may be constituted by one file, and one file may have multiple tables. The data sources and the tables may have various structures, and there is no limitation thereon.

Furthermore, data source is, for example, any one of a relational database, an object-oriented database, an XML database, a NoSQL databases, file data sources, data warehouses, data marts, directory management systems, real-time measurement data, online data services, and streaming data services, and there is no limitation on the type thereof.

Various types of information are stored in the storage unit 41 constituting the search apparatus 4. The various types of information are, for example, the above-described one or more types of indexes, or various types of information in a later-described data dictionary.

A data dictionary is stored in the dictionary storage unit 411. The data dictionary is a group of information for retrieving information from two or more data sources using a search condition input by a user, and integrating the retrieved information. The data dictionary has source layer defining information, user layer defining information, and conversion rule defining information. That is to say, the data dictionary has three-layered information.

The source layer defining information is information defining a schema of a data source. The source layer defining information has, for example, a source identifier and one or more pieces of source attribute defining information. The source layer defining information has, for example, a source identifier, a table identifier, and one or more pieces of source attribute defining information.

The source attribute defining information is information defining an attribute of a table in a data source. The source attribute defining information has a source attribute identifier. The source attribute identifier is information for identifying an attribute of a table in a data source, and is, for example, an attribute name or an ID. The source attribute defining information may have one or more attribute values of attributes of a table in a data source. The one or more attribute values of attributes are, for example, a data type or a size.

The source layer defining information is information corresponding to a table. In the case in which a data source has only one table, the source layer defining information is information corresponding to the data source.

It is preferable that the source layer defining information has data source-specific information. The data source-specific information is information unique to each data source. The data source-specific information has, for example, command base information and connection information.

The command base information is information for generating a search command for a data source. The command base information is information for configuring a search command. It is preferable that pieces of command base information respectively corresponding to the two or more data sources are different types of information. It is preferable that the two or more types of different pieces of command base information has, for example, information for generating a search command in an SQL statement, information for generating a search module, and URL syntax indicating syntax including a URL of a data source that is to be searched.

The command base information is, for example, information for configuring an SQL statement that is to be issued to a data source. The command base information is, for example, information for specifying an API of a module that is used when accessing a data source. The command base information is, for example, URL syntax, and is, for example, a string having a URL and an endpoint (table identifier).

The connection information is information for accessing a data source. The connection information contains, for example, an IP address and a URL. The connection information contains, for example, login information for logging into a data source. The login information contains, for example, a user identifier and a password. The connection information contains, for example, driver identifying information of a data source and an API key.

The user layer defining information is information defining a schema of a user table. The user table is a table that is to be searched based on a search condition input by a user. The user table is typically view, and the view contains one or more records. Such a record has one or more attribute values. It is preferable that such a record has one or more key item values.

The user layer defining information has, for example, a user table identifier and one or more pieces of user attribute defining information. The user table identifier is information for identifying a user table, and is, for example, a table name or an ID. The user attribute defining information is information defining an attribute of a user table. The user attribute defining information contains a user attribute identifier. The user attribute identifier is information for identifying an attribute of a user table. The user attribute identifier is, for example, an attribute name or an attribute ID.

The user attribute defining information typically has user attribute value base information. The user attribute value base information is information for specifying a method for retrieving a user attribute value. The user attribute value base information is information using one or more view attribute values of one or more conversion views. The user attribute value base information has, for example, a view identifier and a view attribute identifier. The user attribute value base information may have, for example, a user table identifier and a user attribute identifier.

The user attribute value base information may have an operation expression, etc. The operation expression, etc. is an operation expression or a program identifier. In the case in which the user attribute value base information has an operation expression, etc., the user attribute value base information has one or at least two identifiers of view identifiers of one or more conversion views and source identifiers of two or more data sources, and attribute identifiers that are paired with the one or at least two identifiers. The attribute identifiers that are paired with the one or more identifiers are one or more attribute identifiers out of view attribute identifiers of any one or more conversion views or source attribute identifiers of any two or more data sources. Then, the operation expression or the program identifier is an identifier of an operation expression or a program that is executed upon accepting one or more attribute values corresponding to the one or more attribute identifiers as parameters. The program identifier is, for example, a module name, a function name, or a method name.

The conversion rule defining information is information that is used by the search unit 432 for generating a search command that is to be issued to each of the two or more data sources, based on the accepted search condition, retrieving search results corresponding to the search command, and generating integrated data corresponding to the search condition.

The conversion rule defining information has one or more pieces of conversion view information. The conversion view information is information defining a conversion view that is configured using one or more data sources out of two or more data sources. The conversion view is a view expressing a corresponding relationship between a user table and one or more data sources. The conversion view may contain one or more records having one or more view attribute values. It is preferable that the one or more view attribute values include a key item value. The conversion view is typically information that is not directly targeted for search by a user. One piece of conversion view information typically corresponds to one data source.

The conversion view information has one or more pieces of view attribute defining information. The conversion view information typically has a view identifier. The view attribute defining information is information defining an attribute of a conversion view. The view attribute defining information has a view attribute identifier and view attribute defining information. The view attribute identifier is information for identifying an attribute of a conversion view. The view attribute identifier is, for example, an attribute name of a conversion view or an attribute ID of a conversion view.

The view attribute value base information is information for specifying a method for retrieving a view attribute value. The view attribute value base information has, for example, a source identifier of a data source from which a view attribute value is retrieved, and a source attribute identifier.

The view attribute value base information has one or more attribute identifiers out of source attribute identifiers of any two or more data sources and view attribute identifiers of any one or more conversion views, an operation expression in which attribute values corresponding to the one or more attribute identifiers are taken as parameters, and the like. The operation expression and the like are an operation expression or a program identifier. The program identifier is information for identifying a program that can be executed using 0 or at least one attribute value as a parameter, and retrieves a view attribute value. The program to which an attribute value that is given is 0 is, for example, "TODAY 0" that retrieves the today's date or "TIME 0" that retrieves the current time.

The conversion rule defining information may have a join method identifier. The join method identifier is information for specifying a method for joining two or more search results retrieved based on the two or more pieces of conversion view information. The join method identifier is, for example, "UNION", "CHOICE", or "LOOKUP". It is preferable that two or more join method identifiers that can be contained in the conversion rule defining information are two or more of "UNION", "CHOICE", and "LOOKUP". It is preferable that the join method identifiers that can be contained in the conversion rule defining information are three or more including "UNION", "CHOICE", and "LOOKUP".

"UNION" is information for specifying merging processing. The merging processing is processing that puts two or more search results into a group with one or at least two key items and aggregates two or more attribute values of respective one or at least two non-key items, thereby configuring one record.

The aggregating two or more attribute values is performing predetermined calculation on two or more attribute values, thereby retrieving one value. The predetermined calculation is, for example, processing that calculates the sum (SUM), calculates the average value (Average), retrieves the maximum value (MAX), retrieves the minimum (MIN), retrieves the median (MEDIAN), calculates the standard deviation, or the like.

"CHOICE" is information for specifying selection processing. The selection processing is processing that selects one or more search results out of two or more search results according to a priority order, and aggregates two or more attribute values of respective one or at least two non-key items, thereby configuring one record. The priority order is a priority order of search results from two or more conversion views or two or more data sources, and is stored in the storage unit 41, for example. The conversion rule defining information may contain the priority order.

"LOOKUP" is information for specifying complementation processing. The complementation processing is processing that specifies one search result serving as a reference source and another search result serving as a reference target according to a reference condition, adds, to an attribute value of a key item of the one search result serving as a reference source out of two or more search results, an attribute value of a key item that is included in the other search result serving as a reference target and is not included in the one search result, and aggregates two or more attribute values of respective one or at least two non-key items, thereby configuring one record. The reference condition is information for specifying one or more attribute values that re to be retrieved from a search result, and is, for example, one or more attribute identifiers.

The processing unit 43 performs various types of processing. The various types of processing are, for example, processing that is performed by the index generating unit 131, the search unit 432, and the index updating unit 133.

The search unit 432 refers to the dictionary storage unit 411, and determines two or more data sources corresponding to the search condition accepted by the accepting unit 12. The determining two or more data sources is retrieving two or more source identifiers. The determining two or more data sources does not have to be simultaneously performed.

Then, the search unit 432 generates a search command for each of the determined two or more data sources using the conversion rule defining information, and retrieves search results based on the search command. Then, the search unit 432 integrates the search results respectively corresponding to the retrieved two or more data sources using the conversion rule defining information and the user layer defining information, thereby retrieving integrated data corresponding to the search condition.

For example, in a case of retrieving a view attribute value corresponding to the view attribute value base information, the search unit 432 retrieves attribute values corresponding to the one or at least two attribute identifiers contained in the contained in the view attribute value base information, from the data sources or the conversion views. Next, the search unit 432 gives the retrieved one or at least two attribute values to the operation expression or a program identified with the program identifier, and executes the operation expression or the program, thereby retrieving a view attribute value. The one or more attribute identifiers contained in the view attribute value base information are each a source attribute identifier or a view attribute identifier. The attribute values respectively corresponding to one or more attribute identifiers contained in the view attribute value base information are each a source attribute value or a view attribute value.

For example, in a case of retrieving a user attribute value corresponding to the user attribute value base information, the search unit 432 retrieves attribute values corresponding to the one or at least two attribute identifiers contained in the user attribute value base information, from the data sources or the conversion views. Next, the search unit 432 gives the retrieved one or more attribute values to the operation expression or a program identified with the program identifier, and executes the operation expression or the program, thereby retrieving a user attribute value. The one or more attribute identifiers contained in the user attribute value base information are each a source attribute identifier or a view attribute identifier. The attribute values respectively corresponding to one or more attribute identifiers contained in the user attribute value base information are each a source attribute value or a view attribute value.

For example, the search unit 432 generates a search command for retrieving information from each of the two or more data sources according to pieces of command base information respectively corresponding to the two or more data sources. Next, the search unit 432 retrieves search results based on the search command for each of the two or more data sources, from the corresponding data sources. Next, the search unit 432 integrates the search results respectively corresponding to the two or more data sources using the conversion rule defining information and the user layer defining information, thereby retrieving integrated data corresponding to the search condition.

For example, the search unit 432 generates a search command that is an SQL statement according to command base information for a data source corresponding to the SQL statement, according to pieces of command base information respectively corresponding to the two or more data sources. For example, the search unit 432 generates a search command that is an interface of a search module according to command base information, for a data source corresponding to the search module. Then, the search unit 432 retrieves search results based on the search command, from the two or more data sources. Next, the search unit 432 integrates the search results respectively corresponding to the two or more data sources using the conversion rule defining information and the user layer defining information, thereby retrieving integrated data corresponding to the search condition.

For example, the search unit 432 accesses the data sources corresponding to the connection information using the connection information for each of the two or more data sources, and retrieves search results based on the search command from the data sources. Next, the search unit 432 integrates the search results respectively corresponding to the two or more data sources using the conversion rule defining information and the user layer defining information, thereby retrieving integrated data corresponding to the search condition.

For example, the search unit 432 retrieves a join method identifier contained in the conversion rule defining information, and joins two or more search results according to a join method specified with the join method identifier, thereby retrieving integrated data.

The search unit 432 retrieves attribute position information corresponding to the attribute identifier included in the search condition, from the array index, retrieves an attribute value corresponding to the attribute identifier included in the search condition from data sources, using the attribute position information, and configures integrated data having the attribute value. In the case in which the data source targeted for search is a data source having the structure described in Embodiment 1, and in the case in which the search unit 432 retrieves information from the data source, the search unit 432 performs the same operation as that of the search unit 132. That is to say, the search unit 432 retrieves information from the data source using one or more types of index information in the index storage unit 112. This search processing of the search unit 432 was described as the search processing of the search unit 132 in Embodiment 1, and thus a description thereof has been omitted.

The source determining part 4321 retrieves one or more user attribute identifiers included in the search condition, and retrieves user attribute value base information corresponding to the one or more user attribute identifiers. Next, the source determining part 4321 retrieves one or more view attribute identifiers corresponding to the one or more pieces of user attribute value base information. Next, the source determining part 4321 retrieves source identifiers corresponding to the one or more view attribute identifiers from the view attribute defining information. It is preferable that the source determining part 4321 performs unique processing on the retrieved source identifiers, thereby retrieving one or at least two unique source identifiers.

The command generating part 4322 generates a search command for each of data sources identified with the two or more source identifiers retrieved by the source determining part 4321, using the search condition and the view attribute value base information.

The command generating part 4322 generates a search command for each data source according to pieces of command base information respectively corresponding to the two or more data sources.

In the case in which the command base information contains syntax information of an SQL statement, the command generating part 4322 generates an SQL statement according to the syntax information of an SQL statement, based on the search condition.

In the case in which the command base information contains syntax information of an interface of a search module, the command generating part 4322 generates a search command that is a string for executing a search module according to the syntax information of an interface of a search module, based on the search condition.

In the case in which the command base information is URL syntax, the command generating part 4322 generates a search command that is a string having, in addition to a URL of URL syntax and an endpoint (table identifier), a condition portion included in the search condition, based on the search condition.

The source search part 4323 retrieves search results based on the search command retrieved by the command generating part 4322, from the two or more data sources. For example, the source search part 4323 executes two or more search command, and retrieves search results from the corresponding data sources.

The integrating part 4324 retrieves integrated data obtained by integrating the search results of the respective two or more data sources retrieved by the source search part 4323, using the search condition and the user layer defining information.

For example, the integrating part 4324 joins two or more search results according to a join method specified with the join method identifier contained in the conversion rule defining information stored in the dictionary storage unit 411, thereby retrieving integrated data.

In the case in which the join method identifier is "UNION", the integrating part 4324 selects one or more search results out of two or more search results according to a priority order, and aggregates two or more attribute values of respective one or at least two non-key items, thereby performing merging processing that configures one record.

In the case in which the join method identifier is "CHOICE", the integrating part 4324 selects an attribute value of a key item included in one or more search results out of two or more search results according to a priority order and aggregates two or more attribute values of non-key items, thereby performing selection processing that configures one record. The priority order is information for specifying one or more conversion views or one or more data sources that are to be given priority over the others in two or more conversion views or two or more data sources. The priority order is stored in the storage unit 41.

In the case in which the join method identifier is "LOOKUP", the integrating part 4324 specifies one search result serving as a reference source and another search result serving as a reference target according to a reference condition, adds, to an attribute value of a key item of the one search result serving as a reference source out of two or more search results, an attribute value of a key item that is included in the other search result serving as a reference target and is not included in the one search result, and aggregates two or more attribute values of respective one or at least two non-key items, thereby performing complementation processing that configures one record. The reference condition is information for specifying one search result serving as a reference source and another search result serving as a reference target. The reference condition is, for example, "<refer to view identifier>identifier 1 <not refer to view identifier>identifier 2". The reference condition is stored in the storage unit 41.

The output unit 44 outputs various types of information. The various types of information are, for example, integrated data. The output is typically transmission to the terminal apparatus 3, but may be a concept that encompasses display on a display screen, projection using a projector, printing by a printer, output of a sound, accumulation in a storage medium, delivery of a processing result to another processing apparatus or another program, and the like.

The result output unit 441 outputs the integrated data retrieved by the search unit 432.

Next, an operation example of the search apparatus 4 constituting the search system B will be described with reference to the flowchart in FIG. 18. In the processing of the search apparatus 4, the processing that generates an index was described in Embodiment 1, and thus a description thereof has been omitted. In this example the search processing that is performed by the search apparatus 4 will be described.

(Step S1801) The condition accepting unit 121 determines whether or not it has accepted a search condition. If it has accepted a search condition, the procedure advances to step S1802, or otherwise the procedure returns to step S1801.

(Step S1802) The source determining part 4321 retrieves a user table identifier included in the search condition accepted in step S1801. The user table identifier is an identifier of a user table targeted for search.

(Step S1803) The source determining part 4321 retrieves one or more user attribute identifiers included in the search condition accepted in step S1801.

This user attribute identifier may be located in any point in a condition portion, an extraction portion, a remaining portion, or the like in the search condition. The condition portion is a portion at which a condition is described in the search condition. The extraction portion is a portion at which an attribute value constituting integrated data is described in the search condition. The remaining portion is a portion other than the condition portion and the extraction portion.

In the case in which the search condition is "SELECT product ID, product name, SUM (sales quantity), SUM (sales total), SUM (purchase total), SUM (sales profit) FROM sales profit by product WHERE product ID=1103 GROUP BY product ID, product name", the condition portion is "product ID=1103", the extraction portion is "product ID, product name, SUM (sales quantity), SUM (sales total), SUM (purchase total), SUM (sales profit)", the remaining portion is "product ID, product name" of phrase "GROUP BY".

(Step S1804) The source determining part 4321 substitutes 1 for a counter i.

(Step S1805) The source determining part 4321 determines whether or not there is an $i^{-th}$ user attribute identifier in the user attribute identifier retrieved in step S1803. If there is an $i^{-th}$ user attribute identifier, the procedure advances to step S1806, or otherwise the procedure advances to step S1808.

(Step S1806) The source determining part 4321 retrieves user attribute value base information that is paired with the $i^{-th}$ user attribute identifier, from the source layer defining information.

(Step S1807) The source determining part 4321 increments the counter i by 1. The procedure returns to step S1805.

(Step S1808) The source determining part 4321 retrieves view identifiers from all pieces of user attribute value base information retrieved in step S1806. The one or more pieces of user attribute value base information may have not a view identifier but a user table identifier.

(Step S1809) The source determining part 4321 performs unique processing on the view identifiers retrieved in step S1808, thereby retrieving view identifiers of one or more conversion views necessary to retrieve integrated data.

(Step S1810) The source determining part 4321 substitutes 1 for a counter j.

(Step S1811) The source determining part 4321 determines whether or not there is a $j^{-th}$ view identifier in the view identifier retrieved in step S1809. If there is a $j^{-th}$ view identifier, the procedure advances to step S1812, or otherwise the procedure advances to step S1819.

(Step S1812) The source determining part 4321 substitutes 1 for a counter k.

(Step S1813) The source determining part 4321 determines whether or not there is a $k^{-th}$ view attribute identifier that is paired with the $j^{-th}$ view identifier in the user attribute value base information retrieved in step S1806. If there is a $k^{-th}$ view attribute identifier, the procedure advances to step S1814, or otherwise the procedure advances to step S1818. The $k^{-th}$ view attribute identifier is a unique view attribute identifier. That is to say, the view attribute identifiers retrieved in this step are not the same. The $k^{-th}$ view attribute identifier may be a user attribute identifier.

(Step S1814) The source determining part 4321 retrieves the $k^{-th}$ view attribute identifier that is paired with the $j^{-th}$ view identifier, from the user attribute value base information retrieved in step S1806. Next, the source determining part 4321 retrieves a $k^{-th}$ piece of view attribute value base information that is paired with the $k^{-th}$ view attribute identifier, from the conversion view information that is paired with the $j^{-th}$ view identifier in the conversion rule defining information.

The $k^{-th}$ view attribute identifier may be a user attribute identifier. In the case in which it is a user attribute identifier, the source determining part 4321 retrieves user attribute value base information that is paired with the user attribute identifier, and retrieves a view identifier contained in the user attribute value base information and view attribute value base information that is paired with the view attribute identifier.

(Step S1815) The source determining part 4321 increments the counter k by 1. The procedure returns to step S1813.

(Step S1816) The source determining part 4321 generates a search command corresponding to the $j^{-th}$ view identifier, using the one or more pieces of view attribute value base information retrieved in step S1814. Below, an example of the command generating processing will be described with reference to the flowchart in FIG. 19.

(Step S1817) The source search part 4323 retrieves a search result from the data source corresponding to the $j^{-th}$ view identifier, using the search command generated in step S1816.

(Step S1818) The source determining part 4321 increments the counter j by 1. The procedure returns to step S1811.

(Step S1819) The integrating part 4324 integrates the search results retrieved in step S1817, thereby retrieving integrated data. Below, an example of the integrating processing will be described with reference to the flowchart in FIG. 20.

(Step S1820) The result output unit 441 outputs the integrated data retrieved in step S1819. The procedure returns to step S1801.

Figure 18:
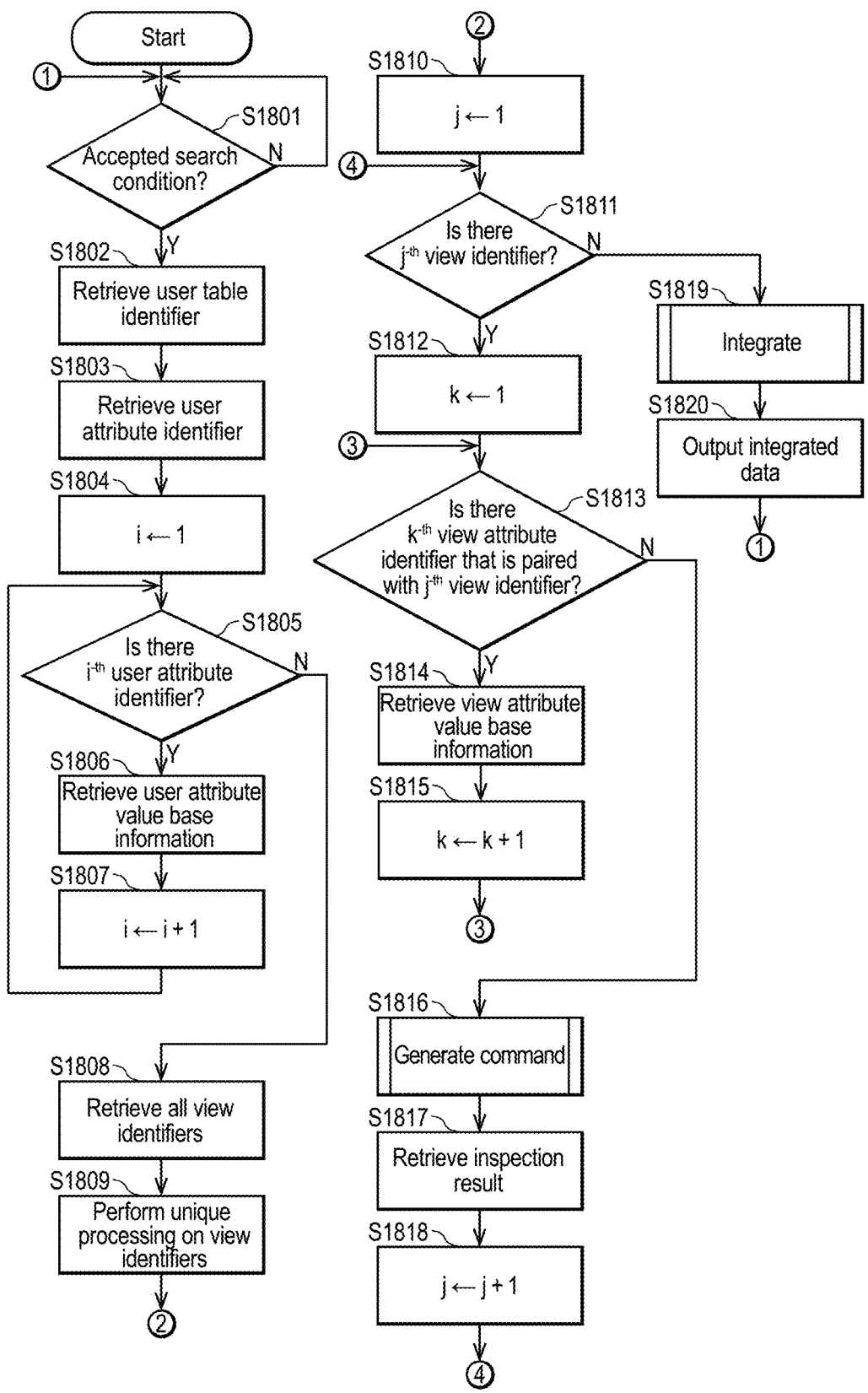
FIG. 18 is a flowchart illustrating an operation example of the search apparatus 4 in the embodiment.

In the flowchart in FIG. 18, the processing ends at power off or at an interruption of termination processing.

Figure 19:
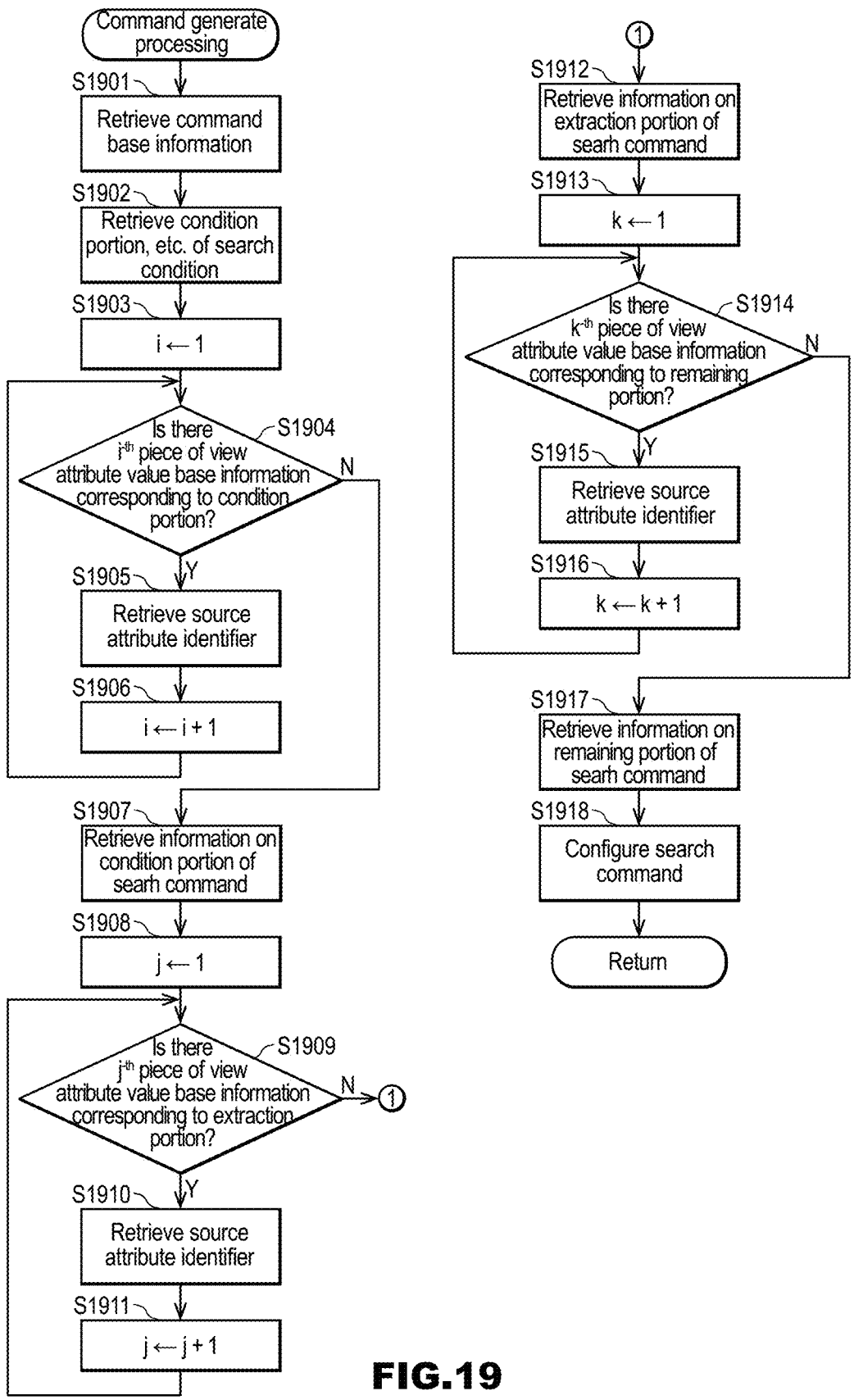
FIG. 19 is a flowchart illustrating of an example of command generating processing in the embodiment.

Next, an example of the command generating processing in step S1816 will be described with reference to the flowchart in FIG. 19.

(Step S1901) The command generating part 4322 retrieves command base information from the data source-specific information of the source layer defining information of the data source corresponding to the $j^{-th}$ view identifier in S1811.

(Step S1902) The command generating part 4322 analyzes the accepted search condition, thereby retrieving information on a condition portion, an extraction portion, and a remaining portion of the search condition.

The processing that analyzes a search condition may be realized, for example, by a known technique such as SQL statement processing software or the like.

(Step S1903) The command generating part 4322 substitutes 1 for a counter i.

(Step S1904) The command generating part 4322 determines whether or not there is an $i^{-th}$ piece of view attribute value base information corresponding to the condition portion retrieved in step S1902. If there is an $i^{-th}$ piece of view attribute value base information corresponding to the condition portion, the procedure advances to step S1905, or otherwise the procedure advances to step S1907.

(Step S1905) The command generating part 4322 retrieves a source attribute identifier contained in the $i^{-th}$ piece of view attribute value base information corresponding to the condition portion retrieved in step S1902.

(Step S1906) The command generating part 4322 increments the counter i by 1. The procedure returns to step S1904.

(Step S1907) The command generating part 4322 retrieves information on the condition portion of the search command according to the command base information retrieved in step S1901, using the one or more source attribute identifiers retrieved in step S1905 and the condition portion in the accepted search condition.

(Step S1908) The command generating part 4322 substitutes 1 for a counter j.

(Step S1909) The command generating part 4322 determines whether or not there is a $j^{-th}$ piece of view attribute value base information corresponding to the extraction portion retrieved in step S1902. If there is a $j^{-th}$ piece of view attribute value base information corresponding to the extraction portion, the procedure advances to step S1910, or otherwise the procedure advances to step S1912.

(Step S1910) The command generating part 4322 retrieves a source attribute identifier contained in the $j^{-th}$ piece of view attribute value base information corresponding to the extraction portion retrieved in step S1902.

(Step S1911) The command generating part 4322 increments the counter j by 1. The procedure returns to step S1909.

(Step S1912) The command generating part 4322 retrieves information on the extraction portion of the search command according to the command base information retrieved in step S1901, using the one or more source attribute identifiers retrieved in step S1910 and the extraction portion in the accepted search condition.

(Step S1913) The command generating part 4322 substitutes 1 for a counter k.

(Step S1914) The command generating part 4322 determines whether or not there is a $k^{-th}$ piece of view attribute value base information corresponding to the remaining portion retrieved in step S1902. If there is a $k^{-th}$ piece of view attribute value base information corresponding to the remaining portion, the procedure advances to step S1915, or otherwise the procedure advances to step S1917.

(Step S1915) The command generating part 4322 retrieves a source attribute identifier contained in the $k^{-th}$ piece of view attribute value base information corresponding to the remaining portion retrieved in step S1902.

(Step S1916) The command generating part 4322 increments the counter k by 1. The procedure returns to step S1914.

(Step S1917) The command generating part 4322 retrieves information on the remaining portion of the search command according to the command base information retrieved in step S1901, using the one or more source attribute identifiers retrieved in step S1915 and the remaining portion in the accepted search condition. The information on the remaining portion may not be retrieved.

(Step S1918) The command generating part 4322 configures a search command based on the command base information retrieved in step S1901, using the information on the condition portion retrieved in step S1907, the information on the extraction portion retrieved in step S1912, and the information on the remaining portion retrieved in step S1917. The procedure returns to the upper-level processing.

In the case in which information on the remaining portion is not retrieved in step S1917, the command generating part 4322 configures a search command using the information on the condition portion retrieved in step S1907 and the information on the extraction portion retrieved in step S1912.

Figure 20:
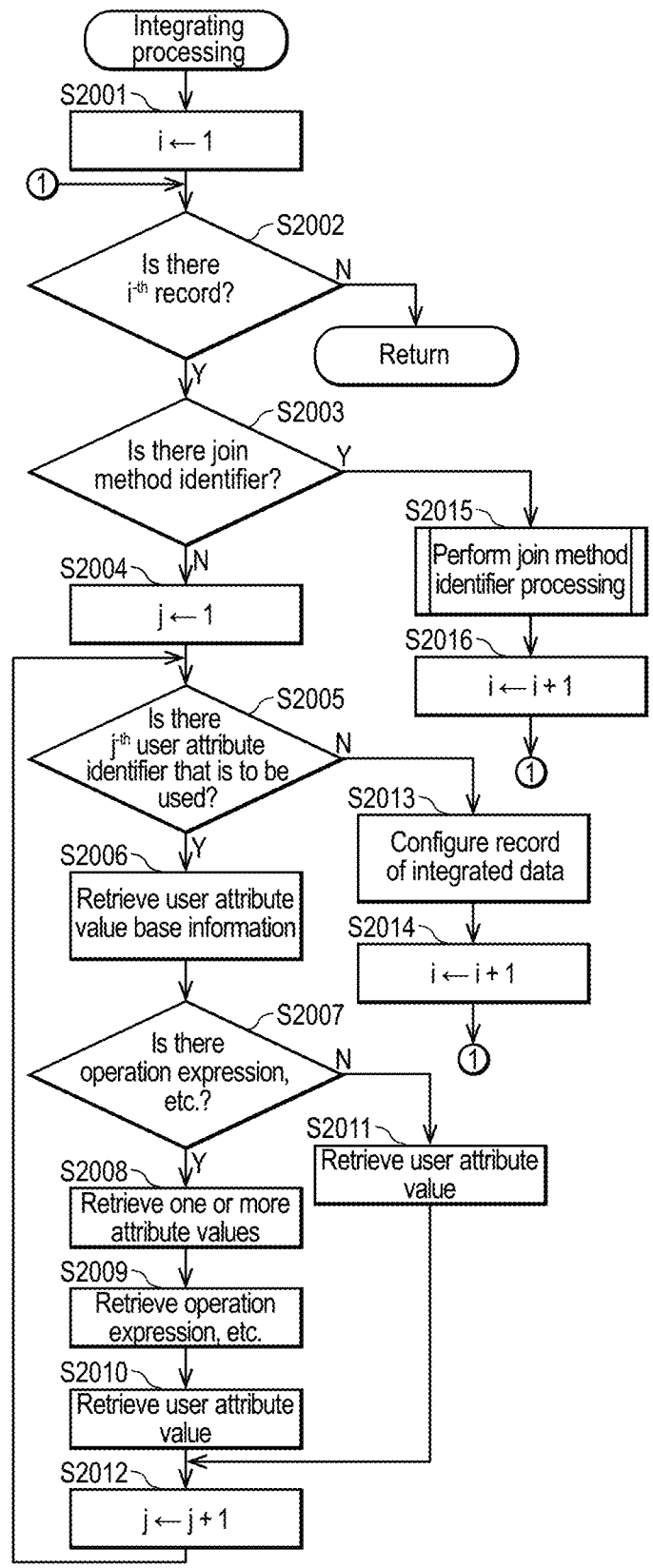
FIG. 20 is a flowchart illustrating of an example of integrating processing in the embodiment.

Next, an example of the integrating processing in step S1819 will be described with reference to the flowchart in FIG. 20.

(Step S2001) The integrating part 4324 substitutes 1 for a counter i.

(Step S2002) The integrating part 4324 determines whether or not search results that are to be joined to each other include an $i^{-th}$ record. If they include an $i^{-th}$ record, the procedure advances to step S2003, or otherwise the procedure returns to the upper-level processing.

(Step S2003) The integrating part 4324 determines whether or not the conversion rule defining information contains a join method identifier. If it does not contain a join method identifier, the procedure advances to step S2004, or otherwise the procedure advances to step S2015.

(Step S2004) The integrating part 4324 substitutes 1 for a counter j.

(Step S2005) The integrating part 4324 determines whether or not there is a $j^{-th}$ user attribute identifier that is to be used for integrated data. If there is a $j^{-th}$ user attribute identifier, the procedure advances to step S2004, or otherwise the procedure advances to step S2013.

(Step S2006) The integrating part 4324 retrieves user attribute value base information that is paired with the $j^{-th}$ user attribute identifier, from the user layer defining information.

(Step S2007) The integrating part 4324 determines whether or not there is an operation expression, etc. in the user attribute value base information retrieved in step S2006. If there is an operation expression, etc., the procedure advances to step S2008, or otherwise the procedure advances to step S2011.

(Step S2008) The integrating part 4324 retrieves one or more view attribute identifiers in the user attribute value base information retrieved in step S2006. Next, the integrating part 4324 retrieves attribute values respectively corresponding to one or more attribute identifiers, from the $i^{-th}$ record of the search result retrieved in S1817. The one or more attribute identifiers include one or more view attribute identifiers. The one or more attribute identifiers may include one or more user attribute identifiers.

(Step S2009) The integrating part 4324 retrieves the operation expression, etc. in the user attribute value base information retrieved in step S2006.

(Step S2010) The integrating part 4324 substitutes each of the one or more attribute values retrieved in step S2008 for the operation expression, etc. retrieved in step S2009, executes the operation expression, etc., thereby retrieving a user attribute value. The procedure advances to step S2010.

(Step S2011) The integrating part 4324 retrieves a user attribute value from the $i^{-th}$ record of the search result.

(Step S2012) The integrating part 4324 increments the counter j by 1. The procedure returns to step S2005.

(Step S2013) The integrating part 4324 retrieves a view attribute identifier of the user attribute value base information retrieved in step S2006. Next, the integrating part 4324 retrieves a view attribute value corresponding to the view attribute identifier from the $i^{-th}$ record of the search result retrieved in S1817, and configures a record of integrated data.

(Step S2014) The integrating part 4324 increments the counter i by 1. The procedure returns to step S2002.

(Step S2015) The integrating part 4324 performs join method identifier processing, thereby integrating the search results. Below, an example of the join method identifier processing will be described with reference to the flowcharts in FIGS. 21 and 22.

(Step S2016) The integrating part 4324 increments the counter i by 1. The procedure returns to step S2002.

Figure 21:
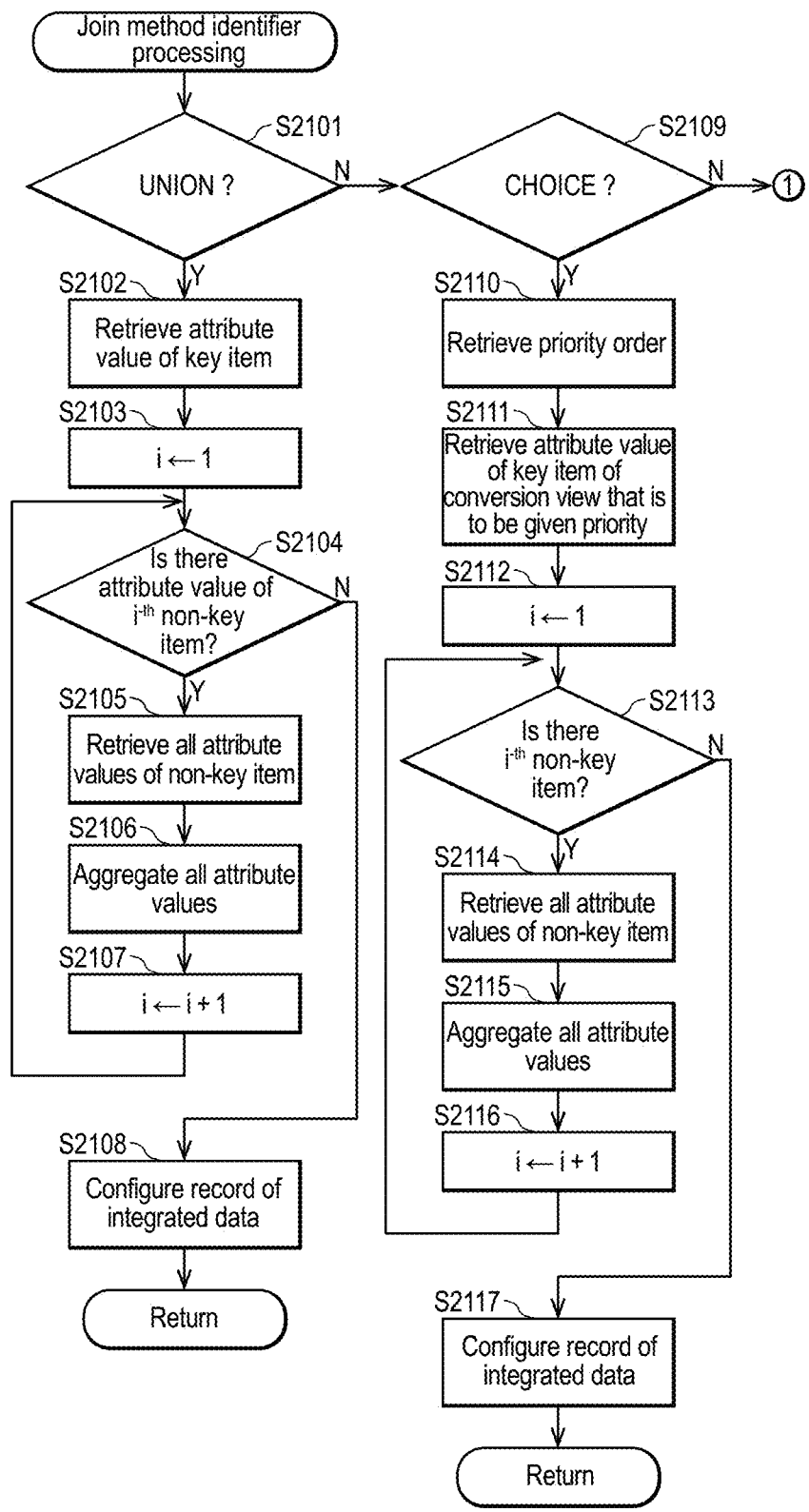
FIG. 21 is a flowchart illustrating of an example of join method identifier processing in the embodiment.
Figure 22:
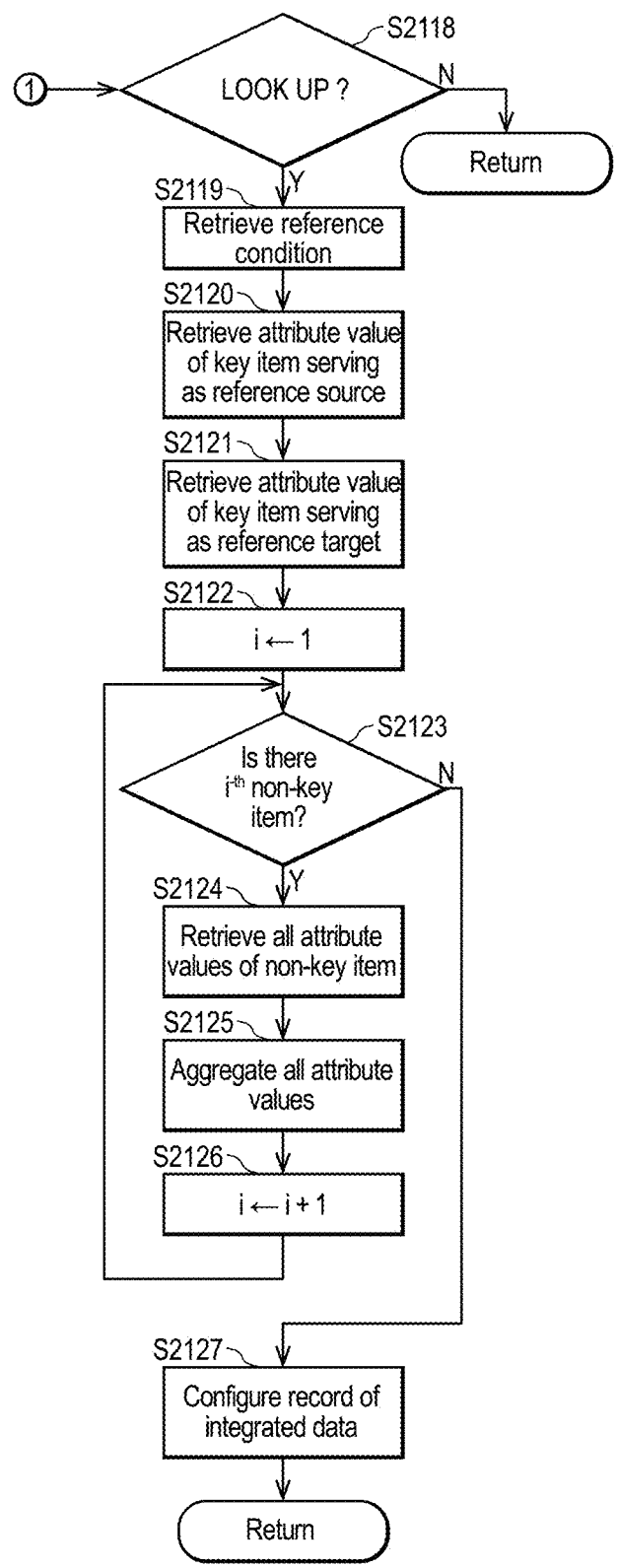
FIG. 22 is a flowchart illustrating of an example of join method identifier processing in the embodiment.

Next, an example of the join method identifier processing in step S2012 will be described with reference to the flowcharts in FIGS. 21 and 22. This join method identifier processing is processing corresponding to the currently focused $i^{-th}$ record (the $i^{-th}$ record in S2002).

(Step S2101) The integrating part 4324 determines whether or not the join method identifier contained in the conversion rule defining information is "UNION". If it is "UNION", the procedure advances to step S2102, or otherwise the procedure advances to step S2113.

(Step S2102) The integrating part 4324 retrieves a group of attribute values of one or more key items from the search result.

(Step S2103) The integrating part 4324 substitutes 1 for a counter i.

(Step S2104) The integrating part 4324 determines whether or not there is an $i^{-th}$ non-key item. If there is an $i^{-th}$ non-key item, the procedure advances to step S2105, or otherwise the procedure advances to step S2108.

(Step S2105) The integrating part 4324 retrieves all attribute values for the $i^{-th}$ non-key item.

(Step S2106) The integrating part 4324 aggregates all attribute values retrieved in step S2105, thereby retrieving an attribute value for the $i^{-th}$ non-key item contained in the integrated data.

(Step S2107) The integrating part 4324 increments the counter i by 1. The procedure returns to step S2104.

(Step S2108) The integrating part 4324 configures a record having the attribute value retrieved in step S2102 and the attribute value retrieved in step S2106 and constituting integrated data. The procedure returns to the upper-level processing.

(Step S2109) The integrating part 4324 determines whether or not the join method identifier contained in the conversion rule defining information is "CHOICE". If it is "CHOICE", the procedure advances to step S2110, or otherwise the procedure advances to step S2118.

(Step S2110) The integrating part 4324 retrieves a priority order from the storage unit 41.

(Step S2111) The integrating part 4324 determines a conversion view that is to be given priority over the others, using the priority order retrieved in step S2110, and retrieves attribute values of one or more key items of the conversion view.

(Step S2112) The integrating part 4324 substitutes 1 for a counter i.

(Step S2113) The integrating part 4324 determines whether or not there is an $i^{-th}$ non-key item. If there is an $i^{-th}$ non-key item, the procedure advances to step S2114, or otherwise the procedure advances to step S2117.

(Step S2114) The integrating part 4324 retrieves all attribute values for the $i^{-th}$ non-key item.

(Step S2115) The integrating part 4324 aggregates all attribute values retrieved in step S2114, thereby retrieving an attribute value for the i-th non-key item contained in the integrated data.

(Step S2116) The integrating part 4324 increments the counter i by 1. The procedure returns to step S2113.

(Step S2117) The integrating part 4324 configures a record having the attribute value retrieved in step S2111 and the attribute value retrieved in step S2115 and constituting integrated data. The procedure returns to the upper-level processing.

(Step S2118) The integrating part 4324 determines whether or not the join method identifier contained in the conversion rule defining information is "LOOKUP". If it is "LOOKUP", the procedure advances to step S2119, or otherwise the procedure returns to the upper-level processing.

(Step S2119) The integrating part 4324 retrieves a reference condition from the storage unit 41.

(Step S2120) The integrating part 4324 determines a conversion view serving as a reference source of the reference condition. Then, the integrating part 4324 retrieves attribute values of one or more key items of the conversion view.

(Step S2121) The integrating part 4324 determines a conversion view serving as a reference target of the reference condition. Then, the integrating part 4324 retrieves attribute values of one or more key items of the conversion view serving as a reference source of the reference condition, the attribute values not being included in a group of attribute values of the conversion view serving as a reference source.

(Step S2122) The integrating part 4324 substitutes 1 for a counter i.

(Step S2123) The integrating part 4324 determines whether or not there is an $i^{-th}$ non-key item. If there is an $i^{-th}$ non-key item, the procedure advances to step S2124, or otherwise the procedure advances to step S2127.

(Step S2124) The integrating part 4324 retrieves all attribute values for the $i^{-th}$ non-key item.

(Step S2125) The integrating part 4324 aggregates all attribute values retrieved in step S2124, thereby retrieving an attribute value for the $i^{-th}$ non-key item contained in the integrated data.

(Step S2126) The integrating part 4324 increments the counter i by 1. The procedure returns to step S2123.

(Step S2127) The integrating part 4324 configures a record having the attribute values retrieved in steps S2120, S2121, and S2125 and constituting integrated data. The procedure returns to the upper-level processing.

Hereinafter, a specific operation example of the search system B in this embodiment will be described. This operation example is an example of processing in which the search apparatus 4 retrieves search results from the data sources stored in two data source management apparatuses 2, and integrates the search results, thereby retrieving integrated data. It is assumed that, in this example, the two data source management apparatuses 2 are apparatuses different from the search apparatus 4, and the two data source management apparatuses 2 are different apparatuses.

Figure 23:
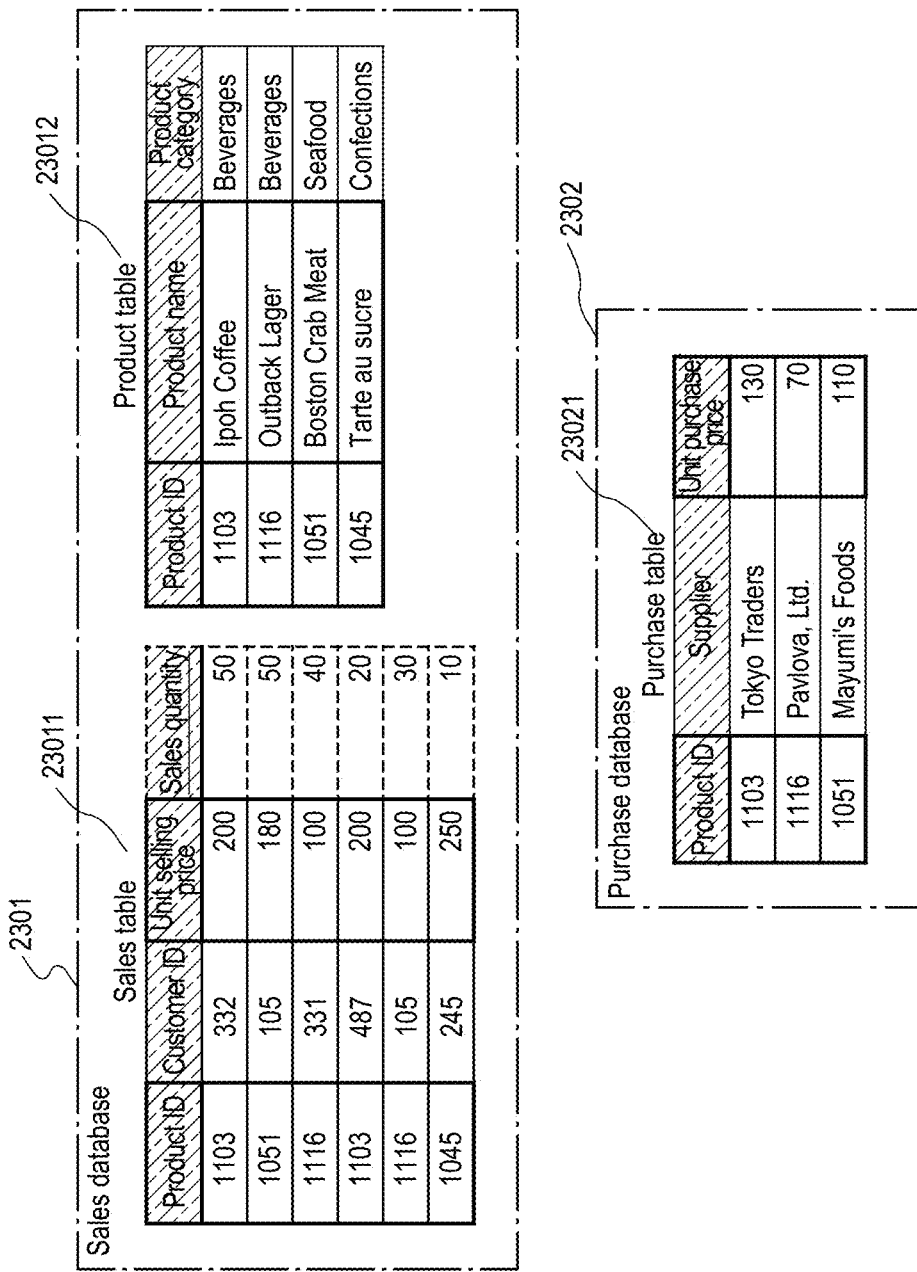
FIG. 23 is a diagram showing an example of a data source in the embodiment.

It is assumed that a sales database denoted by 2301 in FIG. 23 is stored in the data source storage unit 111 of the first data source management apparatus 2. The sales database has a sales table (23011) and a product table (23012). The sales table (23011) manages one or more records each having "product ID", "customer ID", "unit selling price", and "sales quantity". The product table (23012) manages one or more records each having "product ID", "product name", and "product category".

Furthermore, it is assumed that a purchase database denoted by 2302 in FIG. 23 is stored in the data source storage unit 111 of the second data source management apparatus 2. The purchase database in this example has a purchase table (23021). The purchase table (23021) manages one or more records each having "product ID", "supplier", and "unit purchase price".

Furthermore, a data dictionary having three-layered defining information shown in FIGS. 24 to 30 is stored in the dictionary storage unit 411 of the search apparatus 4. This data dictionary is, for example, is information input by an administrator who operates the search apparatus 4.

FIG. 24 shows information defining the schema of the sales table (23011) contained in the source layer defining information. FIG. 24 includes a source identifier "sales database", a table identifier "sales table", and one or more pieces of source attribute defining information. The source attribute defining information is identified with "ID" in the table in FIG. 24. The source attribute defining information in this example has "source attribute identifier", "data type", and "size". The sales database is, for example, a relational database.

FIG. 25 shows information defining the schema of the product table (23012) contained in the source layer defining information. FIG. 25 includes a source identifier "sales database", a table identifier "product table", and one or more pieces of source attribute defining information. The source attribute defining information is identified with "ID" in the table in FIG. 25. The source attribute defining information in this example has "source attribute identifier", "data type", and "size".

FIG. 26 shows information defining the schema of the purchase table (23021) contained in the source layer defining information. FIG. 26 includes a source identifier "purchase database", a table identifier "purchase table", and one or more pieces of source attribute defining information. The source attribute defining information is identified with "ID" in the table in FIG. 26. The source attribute defining information in this example has "source attribute identifier". The purchase database is, for example, the file described in Embodiment 1.

FIG. 27 shows data source-specific information contained in the source layer defining information. 2701 in FIG. 27 is data source-specific information of the sales database. 2702 is data source-specific information of the purchase database.

FIG. 28 shows conversion view information of a sales view, which is one of the conversion views. The conversion view information is contained in the conversion rule defining information. The conversion view information has a view identifier "sales view" and one or more pieces of view attribute defining information. The view attribute defining information is identified with "ID" in the table in FIG. 28.

The view attribute defining information with "ID=1" in FIG. 28 shows that, in the case of retrieving a view attribute identifier "product ID", an attribute value of the source attribute identifier "product ID" of the source identifier "sales table" or an attribute value of the source attribute identifier "product ID" of the source identifier "product table" may be retrieved. That is to say, it is shown that information that is paired with the source attribute identifier "product ID" of the source identifier "sales table" and information that is paired with the source attribute identifier "product ID", which has the same attribute value as that of the above-mentioned "product ID", of the source identifier "product table" are information regarding the same product.

The view attribute defining information with "ID=6" in FIG. 28 means that, in the case of retrieving a view attribute value "sales total", a parameter P1 is multiplied by a parameter P2 as indicated by an operation expression, etc. "P1×P2". "ID=6" in FIG. 28 shows that the parameter P1 is an attribute value of the source attribute identifier "unit selling price" of the source identifier "sales table". Also, it is shown that the parameter P2 is an attribute value of the source attribute identifier "sales quantity" of the source identifier "sales table".

FIG. 29 shows conversion view information of a purchase view, which is one of the conversion views. The conversion view information is contained in the conversion rule defining information. The conversion view information has a view identifier "purchase view" and one or more pieces of view attribute defining information. The view attribute defining information is identified with "ID" in the table in FIG. 29.

FIG. 30 shows information defining the schema of the user table contained in the user layer defining information. The user layer defining information has a user table identifier "product sales profit table" and one or more pieces of user attribute defining information. The user attribute defining information is identified with "ID" in the table in FIG. 30.

The user attribute defining information with "ID=1" in FIG. 30 shows that, in the case of retrieving a user attribute identifier "product ID", an attribute value of the view attribute identifier "product ID" of the view identifier "sales view" or an attribute value of the view attribute identifier "product ID" of the view identifier "purchase view" may be retrieved. That is to say, it is shown that information that is paired with the view attribute identifier "product ID" of the view identifier "sales view" and information that is paired with the view attribute identifier "product ID", which has the same attribute value as that of the above-mentioned "product ID", of the view identifier "purchase view" are information regarding the same product.

Furthermore, in the view attribute defining information with "ID=7" in FIG. 30, the operation expression, etc. "P1×P2" indicates that an attribute value of the user attribute identifier "purchase total" is retrieved by multiplying the parameter P1 the parameter P2. It is shown that the parameter P1 is an attribute value of the view attribute identifier "sales quantity" of the view identifier "sales view". Also, it is shown that the parameter P2 is an attribute value of the view attribute identifier "unit purchase price" of the view identifier "purchase view".

Furthermore, the operation expression, etc. "sub (P1, P2)" in the view attribute defining information with "ID=8" in FIG. 30 indicates that an attribute value of the user attribute identifier "sales profit" is retrieved by substituting values of the two parameters P1 and P2 for a function "sub" (a function that provides a result obtained by subtracting two parameters) and executing the function. It is shown that the parameter P1 is an attribute value of the view attribute identifier "sales total" of the view identifier "sales view". Also, it is shown that the parameter P2 is an attribute value of the view attribute identifier "purchase total" of the user table identifier "product sales profit table".

Figure 31:
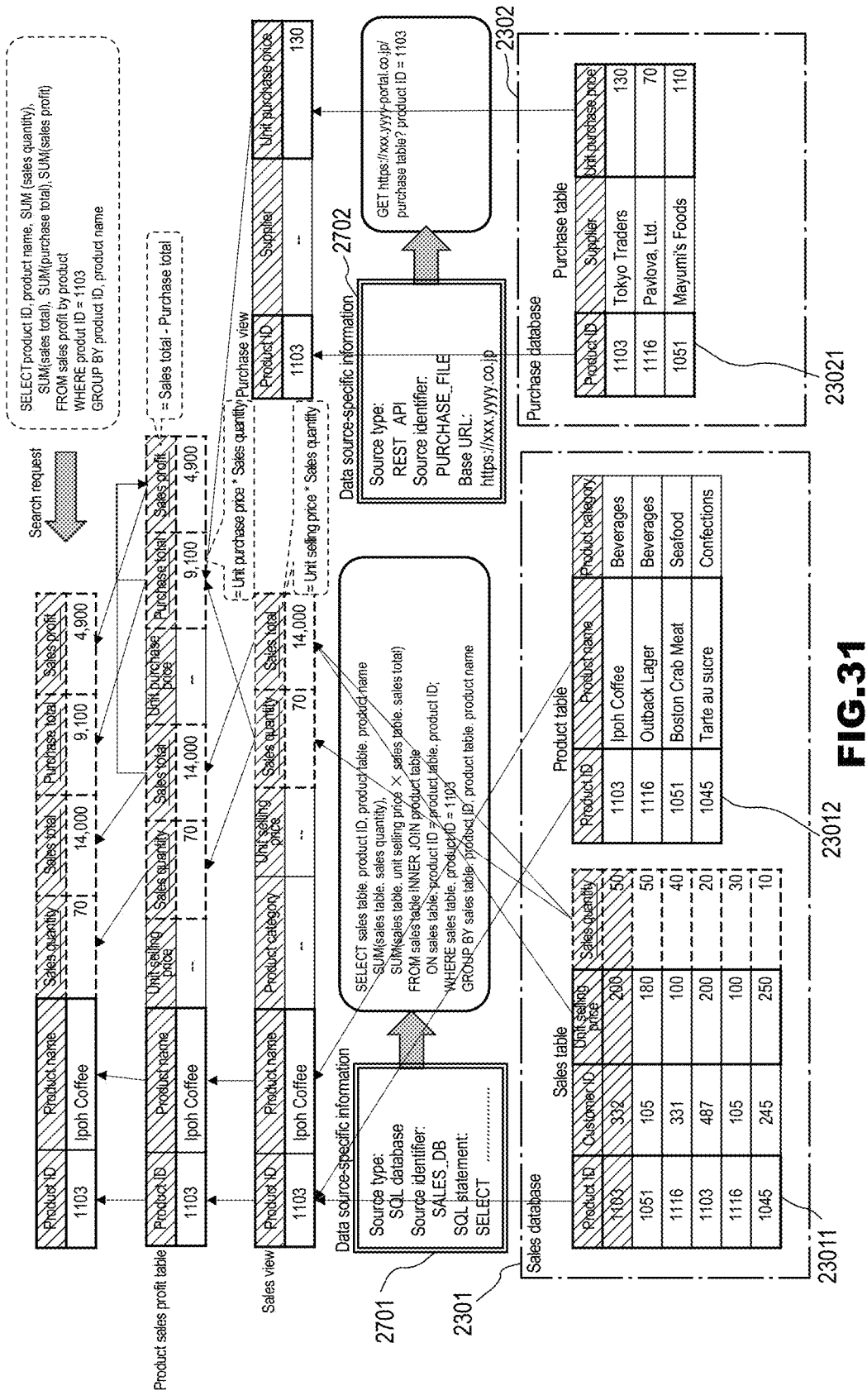
FIG. 31 is a diagram illustrating an operation example of the search apparatus 4 in the embodiment.

Below, an operation example of the search apparatus 4 will be described with reference to FIG. 31. First, it is assumed that a user inputs a search condition:

"SELECT product ID, product name, SUM (sales quantity), SUM (sales total), SUM (purchase total), SUM (sales profit)
FROM sales profit by product
WHERE product ID=1103
GROUP BY product ID, product name", to the terminal apparatus 3. Next, the terminal apparatus 3 accepts the search condition and transmits it to the search apparatus 4.

Next, the condition accepting unit 121 of the search apparatus 4 receives the above-mentioned search condition (SQL statement).

Next, the source determining part 4321 retrieves the user table identifier "sales profit by product" included in the search condition. The source determining part 4321 retrieves the user attribute identifiers "product ID", "product name", "sales quantity", "sales total", "purchase total", and "sales profit" included in the search condition.

Next, the source determining part 4321 retrieves user attribute defining information that is paired with the retrieved user attribute identifiers from the user layer defining information in FIG. 30.

Next, the source determining part 4321 retrieves view identifiers contained in the retrieved user attribute defining information, performs unique processing on the view identifiers, thereby retrieving two view identifiers "sales view" and "purchase view".

Next, the source determining part 4321 retrieves user attribute identifiers "product ID", "product name", "sales quantity", and "sales total" corresponding to the view identifier "sales view" from the retrieved user attribute defining information. Next, the source determining part 4321 retrieves the view attribute identifiers "product ID", "product name", "sales quantity", and "sales total" corresponding to the retrieved user attribute identifiers and the view identifier "sales view".

Next, the source determining part 4321 refers to the conversion view information in FIG. 28, and retrieves view attribute value base information that is paired with the retrieved view attribute identifiers.

Next, the command generating part 4322 retrieves command base information (information that is paired with the tag <command base information> of 2701) corresponding to the view identifier "sales view", from the data source-specific information in FIG. 27.

Next, the command generating part 4322 analyzes the accepted search condition, thereby retrieving a condition portion "product ID=1103", extraction portion "product ID, product name, SUM (sales quantity), SUM (sales total), SUM (purchase total), SUM (sales profit)", and information on the remaining portion "GROUP BY product ID, product name" of the search condition.

Next, the command generating part 4322 retrieves "sales view. product ID" from the user attribute identifier "product ID" of the condition portion "product ID=1103, using the retrieved user attribute value base information. The command generating part 4322 retrieves "sales table. product ID" from "sales view. product ID", using the retrieved view attribute value base information. Then, the command generating part 4322 retrieves a condition portion "sales table. product ID" for configuring a search command that is to be issued to a data source from the condition portion "product ID=1103" of the search command.

Next, in a similar manner, the command generating part 4322 retrieves "sales table. product ID" from "product ID" of the extraction portion "product ID, product name, SUM (sales quantity), SUM (sales total), SUM (purchase total), SUM (sales profit)". The command generating part 4322 retrieves "product table. product name" from "product name" constituting the extraction portion. The command generating part 4322 retrieves "SUM (sales table. sales quantity)" from "SUM (sales quantity)" constituting the extraction portion. The command generating part 4322 retrieves "SUM (sales table. unit selling price×sales table. sales total)" from "SUM (sales total)" constituting the extraction portion.

Next, the command generating part 4322 retrieves "GROUP BY sales table. product ID, product table. product name" from information on the remaining portion "GROUP BY product ID, product name".

Next, the command generating part 4322 retrieves a table identifier "sales table" corresponding to the variable "$ table identifier 1$" and a table identifier "product table" corresponding to the variable "$ table identifier 2$", the variables being contained in "FROM $ table identifier 1$ INNER JOIN $ table identifier 2$" of the command base information.

Next, the command generating part 4322 retrieves a table attribute name "product ID" corresponding to the variable "$ table attribute identifier 1$" and a table attribute name "product ID" corresponding to the variable "$ table attribute identifier 2$", the variables being contained in "ON $ table identifier 1$. $ table attribute identifier 1$=$ table identifier 2$. $ table attribute identifier 2$" of the command base information.

Next, the command generating part 4322 replaces each variable in the command base information;

"SELECT $ extraction portion $
FROM $ table identifier 1$
INNER JOIN $ table identifier 2$
ON $ table identifier 1$. $ table attribute identifier $=$ table identifier 2$. $ table attribute identifier $
WHERE $ condition portion $ $ remaining portion $"
with the retrieved corresponding string to configure a search command;

"SELECT sales table. product ID, product table. product name,
SUM (sales table. sales quantity),
SUM (sales table. unit selling price×sales table. sales total)
FROM sales table INNER JOIN product table
ON sales table. product ID=product table. product ID;
WHERE sales table. product ID=1103
GROUP BY sales table. product ID, product table. product name".

Next, the source search part 4323 retrieves connection information "<JDBC connection URL>jdbc:oracle:thin:@localhost:1521:AAA <driver class>oracle.jdbc.driver.OracleDriver" of 2701 in FIG. 27. Then, the source search part 4323 accesses an SQL database "sales database" using the connection information, and retrieves a search result from the data source "sales database" corresponding to the view identifier, using the generated search command. Then, the source search part 4323 acquires a search result "<product ID>1103 <product name>Ipoh Coffee <sales quantity>70 <sales total>14000".

Next, the command generating part 4322 retrieves "purchase view. product ID" from the user attribute identifier "product ID" of the condition portion "product ID=1103", using the retrieved user attribute value base information. The command generating part 4322 retrieves "purchase table. product ID" from "purchase view. product ID", using the retrieved view attribute value base information. Then, the command generating part 4322 retrieves a condition portion "purchase table. product ID" for configuring a search command that is to be issued to the data source "purchase database", from the condition portion of the search command "product ID=1103".

Furthermore, the command generating part 4322 retrieves "SUM (sales table. sales quantity×purchase table. unit purchase price)" from "SUM (purchase total)" constituting the extraction portion. Next, the command generating part 4322 retrieves information "purchase table. unit purchase price" corresponding to the data source "purchase database" of the extraction portion "SUM (sales table. sales quantity×purchase table. unit purchase price)".

Next, the command generating part 4322 configures a search command "GET https://xxx.yyyy-portal.co.jp/purchase table? product ID=1103" according to command base information "base URL+"/"+endpoint" and a base URL "https://xxx.yyyy-portal.co.jp" (2702 in FIG. 27) of the connection information.

Next, the source search part 4323 searches the purchase table (23021) of the purchase database using the connection information "<API key>XXXXXXXX" of 2701 in FIG. 27 and the search command "GET https://xxx.yyyy-portal.co.jp/purchase table? product ID=1103", and acquires a search result "<product ID>1103 <unit purchase price>130".

Next, the integrating part 4324 acquires integrated data "<product ID>1103 <product name>Ipoh Coffee <sales quantity>70 <sales total>14000 <purchase total>9100 <sales profit>4900" with reference to the retrieved extraction portion "product ID, product name, SUM (sales quantity), SUM (sales total), SUM (purchase total), SUM (sales profit)", using the attribute values of the search result "<product ID>1103 <product name>Ipoh Coffee <sales quantity>70 <sales total>14000" and the search result "<product ID>1103 <unit purchase price>130".

The <purchase total>9100 is an attribute value retrieved by executing the operation expression "sales view. sales quantity×purchase view. unit purchase price" with reference to the user attribute value base information with "ID=7" in FIG. 30.

Furthermore, the <sales profit>4900 is an attribute value retrieved by substituting "sales view. sales total×product sales profit table. purchase total" for program "sub 0" and executing the expression with reference to the user attribute value base information with "ID=8" in FIG. 30.

Then, the result output unit 441 transmits the retrieved integrated data to the terminal apparatus 3.

Next, the terminal apparatus 3 receives and outputs the integrated data. This integrated data is "<product ID>1103 <product name>Ipoh Coffee <sales quantity>70 <sales total>14000 <purchase total>9100 <sales profit>4900".

As described above, according to this embodiment, it is possible to properly search two or more data sources for information and integrate search results, using three-layered defining information consisting of source layer defining information, conversion rule defining information, and user layer defining information.

Furthermore, according to this embodiment, it is possible to search for information at high speed, by using an index including an array index.

The software that realizes the search apparatus 4 in this embodiment is the following sort of program. Specifically, this program is a program for causing a computer capable of accessing a data dictionary and two or more data sources, the data dictionary having: source layer defining information, which is information defining each of two or more data sources including one or more records having one or more attribute values, and is information having a source identifier, which is an identifier of a data source, and one or more pieces of source attribute defining information each containing a source attribute identifier, which is an attribute identifier of a data source; user layer defining information, which is information defining a user table that is to be searched based on a search condition and that includes one or more records having one or more attribute values, and is information having a user table identifier for identifying the user table and one or more pieces of user attribute defining information each containing a user attribute identifier, which is an attribute identifier of the user table; and conversion rule defining information, which is information for generating a search command that is to be issued to each of the two or more data sources, based on the search condition, retrieving search results corresponding to the search command, and generating integrated data corresponding to the search condition using the two or more search results, to function as: a condition accepting unit that accepts a search condition for the user table; a search unit that determines two or more data sources corresponding to the search condition referring to the data dictionary, generates a search command for each of the two or more data sources, using the conversion rule defining information, retrieves search results based on the search command, and integrates the search results respectively corresponding to the two or more data sources using the conversion rule defining information and the user layer defining information, thereby retrieving integrated data corresponding to the search condition; and a result output unit that outputs the integrated data retrieved by the search unit.

Embodiment 3

In this embodiment, a search system including a search apparatus that searches a data source for information using multiple record indexes will be described.

Furthermore, in this embodiment, a search system including a search apparatus that searches a data source for information using two or more types of indexes including a record index will be described. The two or more types of indexes are constituted by, in addition to the record index, for example, one or more types of indexes out of an array index, an array label index, a secondary index, and a source index.

Moreover, in this embodiment, a search system including a search apparatus that generates multiple record indexes will be described.

Figure 32:
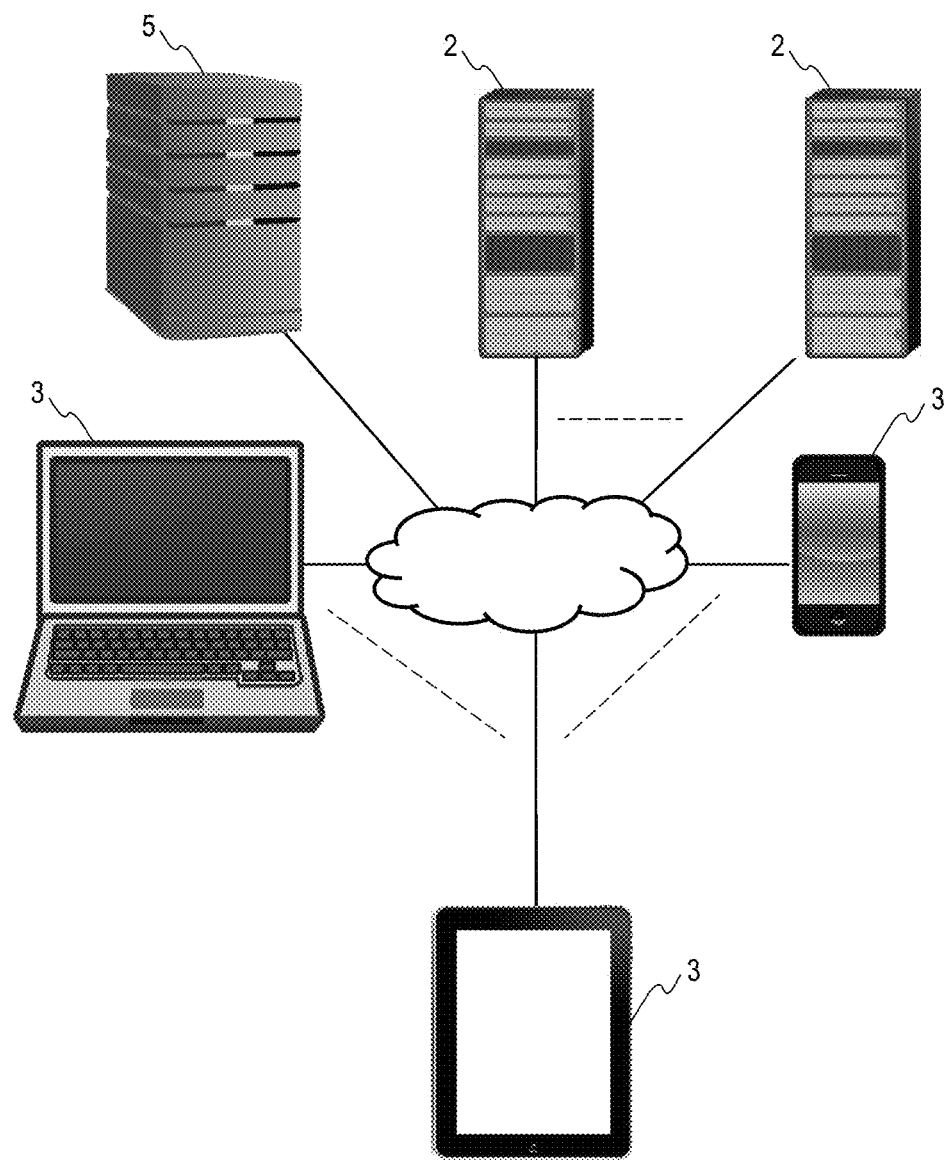
FIG. 32 is a conceptual diagram of the search system B in Embodiment 3.

FIG. 32 is a conceptual diagram of the search system B in this embodiment. The search system B includes a search apparatus 4, one or at least two data source management apparatuses 2, and one or at least two terminal apparatuses 3.

The search apparatus 4 is an apparatus that searches a data source for information. The search apparatus 4 is, for example, a so-called server such as a cloud server, an ASP server, or the like. There is no limitation on the type of the search apparatus 4. The search apparatus 4 may search a data source for information stored in the data source management apparatuses 2 that are external apparatuses, or may search a data source for information inside the search apparatus 4. The one or at least two data source management apparatuses 2 are typically apparatuses different from the search apparatus 4.

Moreover, the search apparatus 4 and the one or more data source management apparatuses 2 can communicate with each other through a network such as the Internet or a LAN. The search apparatus 4 and the terminal apparatuses 3 can communicate with each other through a network such as the Internet or a LAN.

Figure 33:
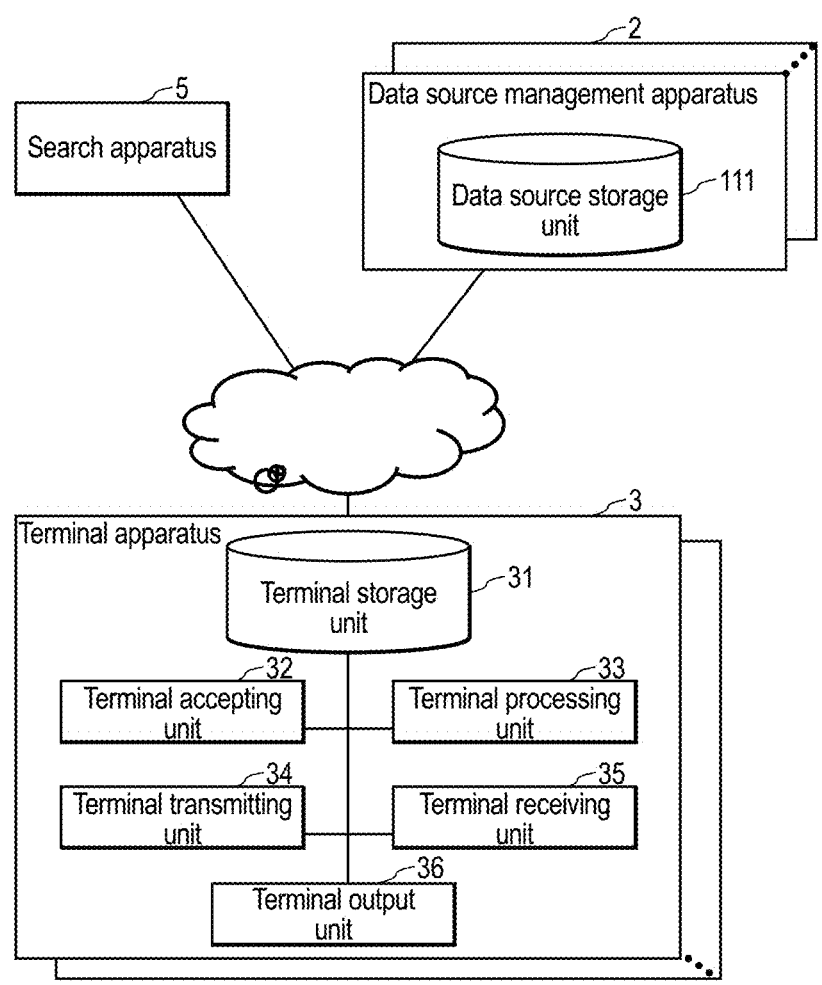
FIG. 33 is a block diagram of the search system B in the embodiment.
Figure 34:
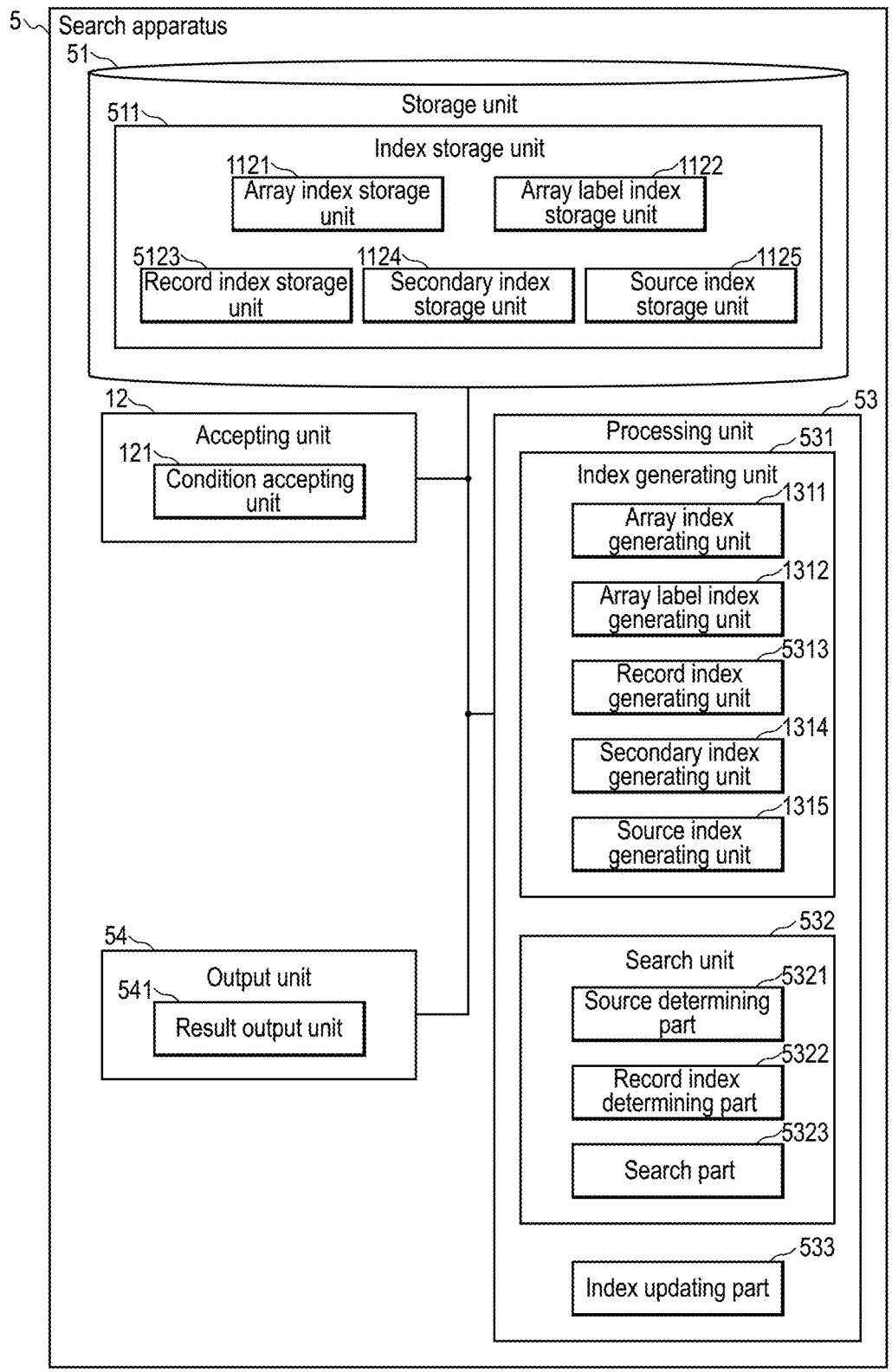
FIG. 34 is a block diagram of the search apparatus 4 in the embodiment.

FIG. 33 is a block diagram of the search system B in this embodiment. FIG. 34 is a block diagram of a search apparatus 5.

The search apparatus 5 includes a storage unit 51, an accepting unit 12, a processing unit 53, and an output unit 54. The storage unit 51 includes an index storage unit 511. The storage unit 51 may include the data source storage unit 111. The index storage unit 511 includes an array index storage unit 1121, an array label index storage unit 1122, a record index storage unit 5113, a secondary index storage unit 1124, and a source index storage unit 1125. The accepting unit 12 includes a condition accepting unit 121. The processing unit 53 includes an index generating unit 531, a search unit 532, and an index updating unit 533. The index generating unit 531 includes an array index generating unit 1311, an array label index generating unit 1312, a record index generating unit 5313, a secondary index generating unit 1314, and a source index generating unit 1315. The search unit 532 includes a source determining part 5321, a record index determining part 5322, and a search part 5323. The output unit 54 includes a result output unit 541.

It is preferable that the search apparatus 5 has the same function as that of the search apparatus 1, except that it can generate multiple record indexes or can search for information using multiple record indexes.

The data source management apparatus 2 includes the data source storage unit 111.

Each terminal apparatus 3 includes the terminal storage unit 31, the terminal accepting unit 32, the terminal processing unit 33, the terminal transmitting unit 34, the terminal receiving unit 35, and the terminal output unit 36.

Various types of information are stored in the storage unit 51 constituting the search apparatus 5. The various types of information are, for example, the above-described one or more types of indexes, data source, or one or more search conditions.

One or more search conditions are associated with a data source. One or more search conditions are a search condition input by a user for searching for information.

The above-described one or more types of indexes are stored in the index storage unit 511. Two or more record indexes are stored in the index storage unit 511. The indexes in the index storage unit 511 may have an index structure such as a secondary index, a BTREE, or an inverted index.

An array index is stored in the array index storage unit 1121. There may be an array index each of two or more record indexes. That is to say, two or more array indexes are stored in the array index storage unit 1121. Note that it is preferable that only one array index is stored in the array index storage unit 1121. This one array index is information corresponding to all of two or more record indexes.

Two or more record indexes are stored in the record index storage unit 5113. One or at least two record indexes are stored in the record index storage unit 1123 typically for each data source. In the case in which there are two or more record indexes corresponding to one data source, these two or more record indexes are record indexes respectively corresponding to combinations of different key items.

Each of two or more record indexes has one or more record index records. A record index record is a group of combinations of one or more key item values and record position information.

In the case in which two or more record indexes correspond to one array index, the record index record may be configured as a group of combinations of one or more key item values and position information of a record of the array index, and have record position information such that each record of the array index corresponds to a record of a data source. In this case as well, record position information of a data source is associated with a record index record, and thus the record index record may be considered to have the record position information.

Furthermore, the record index record corresponds to a record of a data source. One or more key item values included in such a record index record correspond to a combination of one or more key items. The combination of one or more key items is one key item or a combination of two or more key items.

It is preferable that the record index records in the record index are sorted in the ascending order or the descending order using one or more key items as a key. It is preferable that the number of record index records in the record index matches the number of all records included in the corresponding data source. Moreover, in the case in which the record index corresponds to two or more key items, the two or more key items are ordered.

It is preferable that schema information of record indexes corresponding to two or more record indexes is stored in the record index storage unit 5113. The schema information of record indexes typically has key item identifiers (attribute identifiers) respectively corresponding to one or more key item values included in the record indexes.

The record indexes in the record index storage unit 5113 may have an index structure such as a secondary index, a BTREE, or an inverted index.

The processing unit 53 performs various types of processing. The various types of processing are, for example, processing that is performed by the index generating unit 531, the search unit 532, and the index updating unit 533.

The index generating unit 531 generates an index from each of the one or at least two data sources. The indexes generated by the index generating unit 531 include two or more record indexes. It is preferable that the indexes generated by the index generating unit 531 include an array index, an array label index, a secondary index, and a source index.

The record index generating unit 5313 generates one or at least two record indexes for each data source. The processing performed in the case in which the record index generating unit 5313 generates one record index for one data source is the same as that of the record index generating unit 1313, and thus a description thereof has been omitted.

In this example, a case in which the record index generating unit 5313 generates two or more record indexes for each of one or more data sources will be described.

The record index generating unit 5313 refers to a data source, generates two or more record indexes, and accumulates them in the record index storage unit 5113. The two or more record indexes are respectively two or more record indexes each corresponding to a combination of one or more different key items.

More specifically, the record index generating unit 5313 retrieves information of two or more combinations for specifying a combination of one or more key items. Next, the record index generating unit 5313 retrieves, for each of the two or more combinations, a record index record having a key item value (attribute value) corresponding to each of one or more key items corresponding to each combination and record position information, for each record of a data source. Then, the record index generating unit 5313 sorts, for each of the two or more combinations, the record index records using one or more key items as a key, configures a record index, which is a group of the sorted record index records, and accumulates it in the record index storage unit 5113.

That is to say, for example, the record index generating unit 5313 determines two or more combinations of one or more key items that satisfy a selecting condition, generates a record index, which is a combination of a key item value and record position information of each of two or more records corresponding to a combination of one or more key items of each of the two or more combinations, and accumulates it in the record index storage unit 5113. The selecting condition is a condition for automatically determining a combination of key items. A specific example of the selecting condition will be described later.

Examples of the method in which the record index generating unit 5313 retrieves information of a combination of one or more key items as described above include (1) a method through designation by a user and (2) a method through automatic retrieval. Furthermore, (2) the method through automatic retrieval includes, for example, (2-1) a method using a search condition, (2-2) a method using a variance, and the like. Hereinafter, each method will be described.

(1) Method Through Designation by User

The record index generating unit 5313 retrieves two or more combinations of one or more key item identifiers designated by a user. The information of the two or more combinations is contained in an index generating instruction input by a user. The information of the two or more combinations is one key item identifier or a group of two or more key item identifiers.

(2) Method Through Automatic Retrieval

The record index generating unit 5313 retrieves information of two or more combinations that satisfy a selecting condition.

(2-1) Method Using Search Condition

For example, the record index generating unit 5313 retrieves, as a key item identifier, an attribute identifier whose appearance frequency satisfies a selecting condition in previous one or more search conditions. The appearance frequency may be the number of times of appearance or the appearance ratio in previous one or more search conditions. The selecting condition is, for example, that the appearance frequency is greater than or equal to a threshold or is greater than the threshold.

For example, the record index generating unit 5313 retrieves, as a combination of key item identifiers, a combination of two or more attribute identifiers whose co-occurrence frequency satisfies a selecting condition in previous one or more search conditions. The co-occurrence frequency may be the number of times of co-occurrence or the co-occurrence ratio in previous one or more search conditions. The selecting condition is, for example, that the co-occurrence frequency is greater than or equal to a threshold or is greater than the threshold.

(2-2) Method Using Variance

For example, the record index generating unit 5313 retrieves, as key item identifiers, attribute identifiers of two or more attributes whose variance of attribute values included in two or more records of a data source for which an index is to be generated satisfies a selecting condition. The selecting condition is that attribute values have a variance that is greater than or equal to a threshold or is greater than the threshold.

For example, the record index generating unit 5313 retrieves, as a combination of one or more key item identifiers, a combination of N or less attribute identifiers (N is a natural number of 1 or more) out of the attribute identifiers of two or more attributes whose variance of attribute values included in two or more records of a data source for which an index is to be generated satisfies a selecting condition.

The search unit 532 selects one record index out of the two or more record indexes using the search condition accepted by the condition accepting unit 121, retrieves record position information that is paired with the key item value included in the search condition, from the selected record index, and retrieves an attribute value in a record corresponding to a position specified with the record position information, from the data source. The retrieved attribute value is, for example, an attribute value corresponding to an attribute identifier designated with the search condition or all attribute values in a record. The key item value may be considered to be an attribute value.

The method in which the search unit 532 performs search using the search condition is as follows. That is to say, the search unit 532 selects one record index corresponding to a combination of one or more key items including a key item corresponding to the key item value included in the search condition. The processing that selects one record index will be described later in detail as processing of the record index determining part 5322.

For example, the search unit 532 retrieves attribute position information corresponding to the attribute identifier included in the search condition, from the array index, and retrieves an attribute value corresponding to the attribute identifier included in the search condition, from the data source, using the attribute position information.

For example, the search unit 532 selects one record index corresponding to a combination of one or more key items including a key item corresponding to the key item value included in the search condition accepted by the condition accepting unit 121, out of the two or more record indexes, retrieves record position information that is paired with the key item value included in the search condition, from the selected record index, and determines a record corresponding to a position specified with the record position information. Next, the search unit 532 retrieves attribute position information corresponding to the attribute identifier included in the search condition, from the array index, and retrieves an attribute value corresponding to the attribute identifier included in the search condition, from the determined record, using the attribute position information.

For example, in the case in which a key item at a beginning of a record index matches a key item corresponding to the key item value included in the search condition, the search unit 532 selects the record index out of the two or more record indexes, retrieves record position information that is paired with the key item value included in the search condition, from the selected record index, and retrieves an attribute value in a record corresponding to a position specified with the record position information, from the data source.

In the case in which there are two or more record indexes in which a key item at a beginning of a record index matches a key item corresponding to the key item value included in the search condition, the search unit 532 determines whether or not a key item following the two or more record indexes matches the key item included in the search condition, selects one record index in which the largest number of key items from the beginning of the record index are included in the key item included in the search condition, retrieves record position information that is paired with the key item value included in the search condition, from the selected record index, and retrieves an attribute value in a record corresponding to a position specified with the record position information, from the data source.

The source determining part 5321 retrieves a source identifier that matches the key item value included in the search condition or that is paired with the smallest key item value and the largest key item value between which the key item value is located, from the source index.

The record index determining part 5322 determines one record index that is to be used for search processing, out of the two or more record indexes. For example, the record index determining part 5322 determines one record index out of the two or more record indexes that are paired with the source identifier retrieved by the source determining part 5321.

For example, the record index determining part 5322 selects one record index corresponding to a combination of one or more key items including a key item included in the search condition accepted by the condition accepting unit 121, out of the two or more record indexes. The key item included in the search condition may be considered to be a key item corresponding to a key item value included in the search condition. The key item included in the search condition may be considered to be a key item identifier included in the search condition.

For example, in the case in which a key item at the beginning of one record index matches a key item included in the search condition, the record index determining part 5322 selects the record index out of the two or more record indexes. For example, in the case in which there are two or more record indexes in which a key item at the beginning of the record index matches a key item included in the search condition, the record index determining part 5322 determines whether or not a key item following the two or more record indexes matches a key item included in the search condition, and selects one record index in which the largest number of key items from the beginning of the record index are included in the key item included in the search condition, out of the two or more record indexes.

The search part 5323 retrieves record position information that is paired with the key item value included in the search condition, from the record index selected by the record index determining part 5322. Next, the search part 5323 retrieves one or more attribute values in a record corresponding to a position specified with the record position information, from the data source. The one or more attribute values may be attribute values corresponding to attribute identifiers included in the search condition, all attribute values of a record at a position specified with the record position information, or the like.

In the case in which the search part 5323 retrieves record position information that is paired with the key item value included in the search condition from the record index, the search part 5323 may perform, for example, binary search in the record index, thereby retrieving record position information. For example, the search part 5323 may search a record index having an index structure for record position information using the index structure.

The search part 5323 retrieves record position information that is paired with the key item value included in the search condition, from the record index selected by the record index determining part 5322. Next, for example, the search part 5323 retrieves attribute position information corresponding to the attribute identifier included in the search condition, from the array index. Then, for example, the search part 5323 retrieves an attribute value included in a record at a position specified with the record position information and located at a position specified with the attribute position information.

The search part 5323 may retrieve position information of a record of an array index from the record index selected by the record index determining part 5322, retrieve record position information of a data source from the record indicated by the position information of the record of the array index, and retrieve an attribute value included in a record at a position specified with the record position information and located at a position specified with the attribute position information corresponding to the attribute identifier included in the search condition.

In the case in which the record index determining part 5322 does not select a record index, the search part 5323 typically performs sequential search in a data source targeted for search, thereby retrieving one or more attribute values corresponding to the search condition.

Furthermore, in the case in which the key item at the beginning of a record index is not included in the search condition and the 2-nd value and subsequent key items are included in the search condition, the search part 5323 preferably scans the entire record index, thereby retrieving record position information corresponding to the search condition. In this case as well, it is possible to perform search typically at higher speed than the case of performing sequential search in the entire data source.

In the case in which a predetermined condition is satisfied, the index updating unit 533 determines whether or not the last updated time indicated by the last updated time information retrieved from the data source is after the generated time indicated by the generated time information corresponding to each of the one or more types of indexes, and, in the case in which the last updated time is after the generated time, the index updating unit operates the index generating unit 531 to configure each of the one or more types of indexes. The index updating unit 533 typically overwrites old indexes in the index storage unit 511 to the configured respective one or more types of indexes. The one or more types of indexes are one or more of an array index, an array label index, a record index, a secondary index, and a source index. The predetermined condition is, for example, that an instruction from a user has been accepted, that it has reached predetermined time, or that it has a data source has been updated.

For example, in the case in which a predetermined condition is satisfied by one data source, the index updating unit 533 updates two or more record indexes of the data source.

The output unit 54 outputs various types of information. The various types of information are, for example, a later-described search result. The output is typically transmission to the terminal apparatus 3, but may be a concept that encompasses display on a display screen, projection using a projector, printing by a printer, accumulation in a storage medium, delivery of a processing result to another processing apparatus or another program, and the like.

The result output unit 541 outputs a search result including the one or more attribute values retrieved by the search unit 532.

The storage unit 51, the index storage unit 511, and the record index storage unit 5113 are preferably non-volatile storage media, but can also be realized by volatile storage media.

There is no limitation on the procedure in which information is stored in the storage unit 51 and the like. For example, information may be stored in the storage unit 51 and the like via a storage medium, information transmitted via a communication line or the like may be stored in the storage unit 51 and the like, or information input via an input device may be stored in the storage unit 11 and the like.

The processing unit 53, the index generating unit 531, the search unit 532, the index updating unit 533, the record index generating unit 5313, the source determining part 5321, the record index determining part 5322, and the search part 5323 may be realized typically by processors, memories, or the like. Typically, the processing procedure of the processing unit 13 and the like is realized by software, and the software is stored in a storage medium such as a ROM. Note that the processing procedure may be realized by hardware (a dedicated circuit). The processors are, for example, CPUs, MPUs, or GPUs, but there is no limitation on the type thereof.

The output unit 54, and the result output unit 541 are typically realized by wired or wireless communication parts, but may also be realized by broadcasting parts.

Next, an operation example of the search system B will be described. First, an operation example of the search apparatus 5 will be described with reference to the flowchart in FIG. 35. In the flowchart in FIG. 35, a description of the same steps as those in the flowchart in FIG. 5 has been omitted.

(Step S3501) The index generating unit 531 generates an index corresponding to the $i^{-th}$ data source. Below, an example of index generating processing will be described with reference to the flowchart in FIG. 19.

Figure 36:
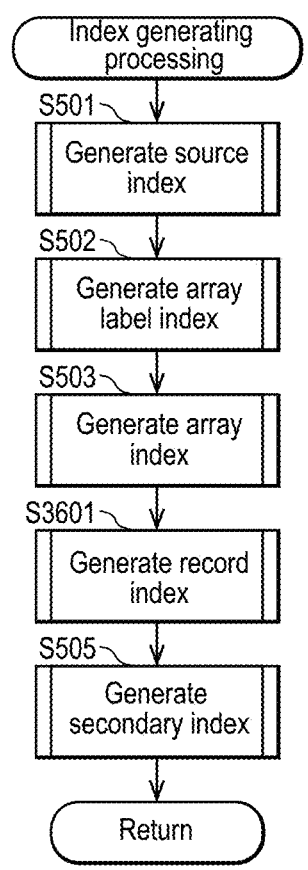
FIG. 36 is a flowchart illustrating of an example of index generating processing in the embodiment.

(Step S3502) The index updating unit 533 instructs the index generating unit 531 to operate. As a result, the index generating unit 531 generates an index, and accumulates the index in association with the $i^{-th}$ data source. Through this processing, the index corresponding to the $i^{-th}$ data source is updated. The flowchart in FIG. 36 shows an example of the index generating processing.

(Step S3503) The search unit 532 performs search using the search condition. Below, an example of this search processing will be described with reference to the flowchart in FIGS. 41 and 42.

Figure 35:
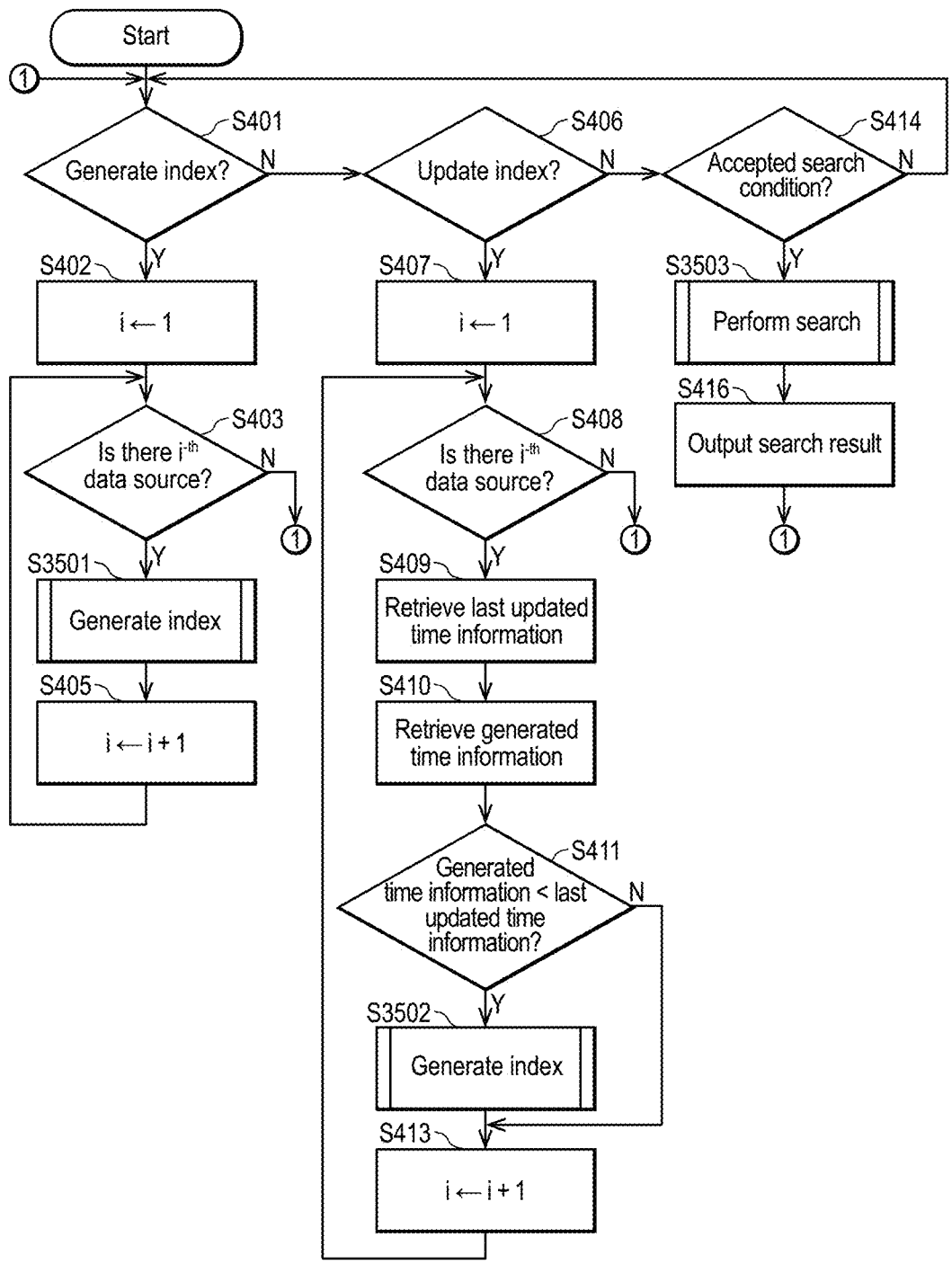
FIG. 35 is a flowchart illustrating an operation example of the search apparatus 4 in the embodiment.

In the flowchart in FIG. 35, it is preferable that the search condition accepted in in step S414 is accumulated in the storage unit 51 in association with the data source targeted for search.

Furthermore, in the flowchart in FIG. 35, the processing ends at power off or at an interruption of termination processing.

Next, step S3501, an example of the index generating processing in step S3502 will be described with reference to the flowchart in FIG. 36. In the flowchart in FIG. 36, a description of the same steps as those in the flowchart in FIG. 5 has been omitted.

(Step S3601) The record index generating unit 5313 generates one or at least two record indexes. Below, an example of the record index generating processing will be described with reference to the flowchart in FIG. 37.

Next, an example of the record index generating processing in step S3601 will be described with reference to the flowchart in FIG. 37. In the flowchart in FIG. 37, a description of the same steps as those in the flowchart in FIG. 4 has been omitted.

(Step S3701) The record index generating unit 5313 determines one or more key item groups corresponding to a record index that is to be generated. Below, an example of the key item group determining processing will be described with reference to the flowchart in FIG. 38. The key item group is constituted by one or at least two key items. That processing that determines a key item group is typically processing that retrieves one or at least two key item identifiers.

(Step S3702) The record index generating unit 5313 substitutes 1 for a counter i.

(Step S3703) The record index generating unit 5313 determines whether or not there is an $i^{-th}$ key item group in the key item group retrieved in step S3701. If there is an $i^{-th}$ key item group, the procedure advances to step S3704, or otherwise the procedure returns to the upper-level processing.

(Step S3704) The record index generating unit 5313 substitutes 1 for a counter j.

(Step S3705) The record index generating unit 5313 determines whether or not there is a $j^{-th}$ record in the data source targeted for search. If there is a $j^{-th}$ record, the procedure advances to step S3706, or otherwise the procedure advances to step S3712.

(Step S3706) The record index generating unit 5313 retrieves record position information of the $j^{-th}$ record.

(Step S3707) The record index generating unit 5313 retrieves key item values, which are one or more key item values of the $j^{-th}$ record and values (attribute values) of one or more key items included in the $i^{-th}$ key item group.

(Step S3708) The record index generating unit 5313 retrieves position information of a $j^{-th}$ record index record.

(Step S3709) The record index generating unit 5313 configures a $j^{-th}$ record index record having record position information, one or more key item values, and position information of the record index record.

(Step S3710) The record index generating unit 5313 adds the $j^{-th}$ record index record configured in step S3709 to an $i^{-th}$ record index (Step S3711) The record index generating unit 5313 increments the counter j by 1. The procedure returns to step S3705.

(Step S3712) The record index generating unit 5313 retrieves and accumulates the schema information of the $i^{-th}$ record index. The schema information has one or more key item identifiers (attribute identifiers) included in the $i^{-th}$ key item group.

(Step S3713) The record index generating unit 5313 accumulates the $i^{-th}$ record index in the record index storage unit 5113. It is preferable that the record index generating unit 5313 accumulates the schema information of the $i^{-th}$ record index as well in association with the $i^{-th}$ record index.

(Step S3714) The record index generating unit 5313 increments the counter i by 1. The procedure returns to step S3703.

Figure 37:
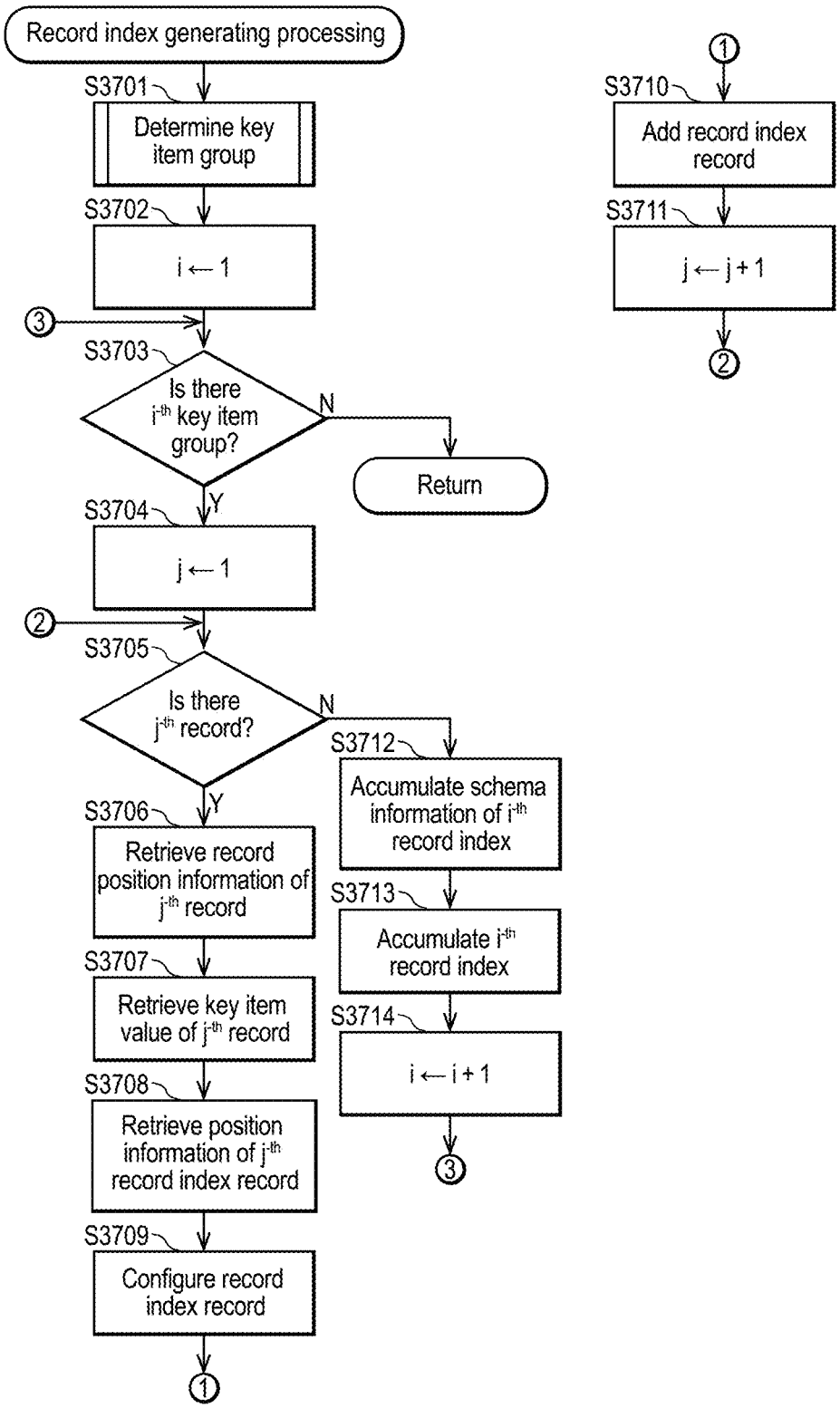
FIG. 37 is a flowchart illustrating of an example of record index generating processing in the embodiment.

In the flowchart in FIG. 37, in the case in which there is no secondary index, step S3708 is not necessary, and, in step S3709, the record index generating unit 5313 configures a $j^{-th}$ record index record having record position information and one or more key item values.

Figure 38:
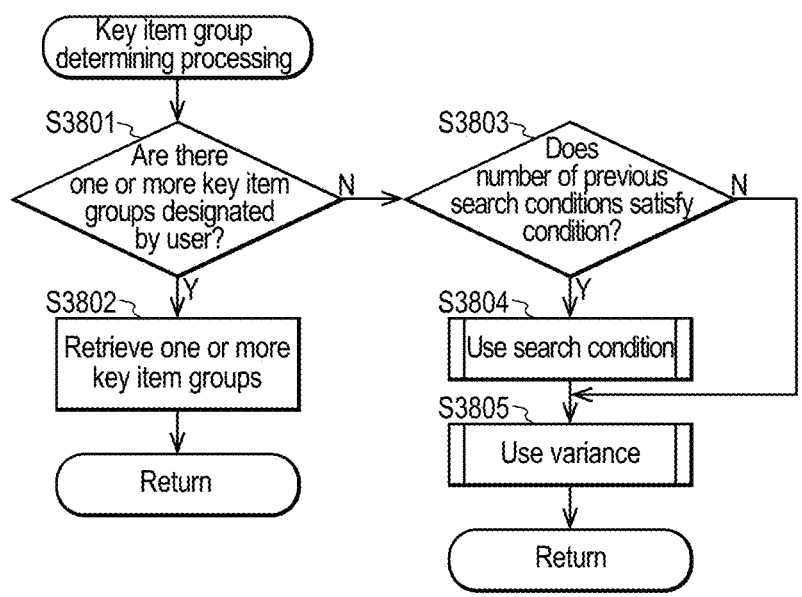
FIG. 38 is a flowchart illustrating of an example of key item group determining processing in the embodiment.

Next, an example of the key item group determining processing in step S3701 will be described with reference to the flowchart in FIG. 38.

(Step S3801) The record index generating unit 5313 determines whether or not there are one or more key item groups designated by a user. If there are one or more key item groups designated by a user, the procedure advances to step S3802, or otherwise the procedure advances to step S3803.

(Step S3802) The record index generating unit 5313 retrieves one or more key item groups designated by a user, and temporarily accumulates them in an unshown buffer. The procedure returns to the upper-level processing.

(Step S3803) The record index generating unit 5313 determines whether or not the number of previous search conditions stored in the storage unit 51, the previous search conditions being for a data source targeted for search, is large enough to satisfy a condition. If the number is large enough to satisfy a condition, the procedure advances to step S3804, or otherwise the procedure advances to step S3805. The condition is, for example, the number of search conditions is greater than or equal to a threshold or is greater than the threshold.

(Step S3804) The record index generating unit 5313 determines one or at least two key item groups, using a search condition in the storage unit 51. Below, an example of the search condition-using processing will be described with reference to the flowchart in FIG. 39.

(Step S3805) The record index generating unit 5313 determines one or at least two key item groups using a variance of attribute values of each attribute in a data source. The procedure returns to the upper-level processing. Below, an example of the variance-using processing will be described with reference to the flowchart in FIG. 40.

The processing that retrieves one or more key item groups designated by a user, the processing that retrieves one or more key item groups using previous search conditions, and processing that retrieves one or more key item groups using a variance of attribute values were described with reference to FIG. 38. In FIG. 38, it is also possible to retrieve one or more key item groups by performing two or more types of processing out of the three types of processing. In this case, the same key item group is not retrieved in a duplicated manner.

Figure 39:
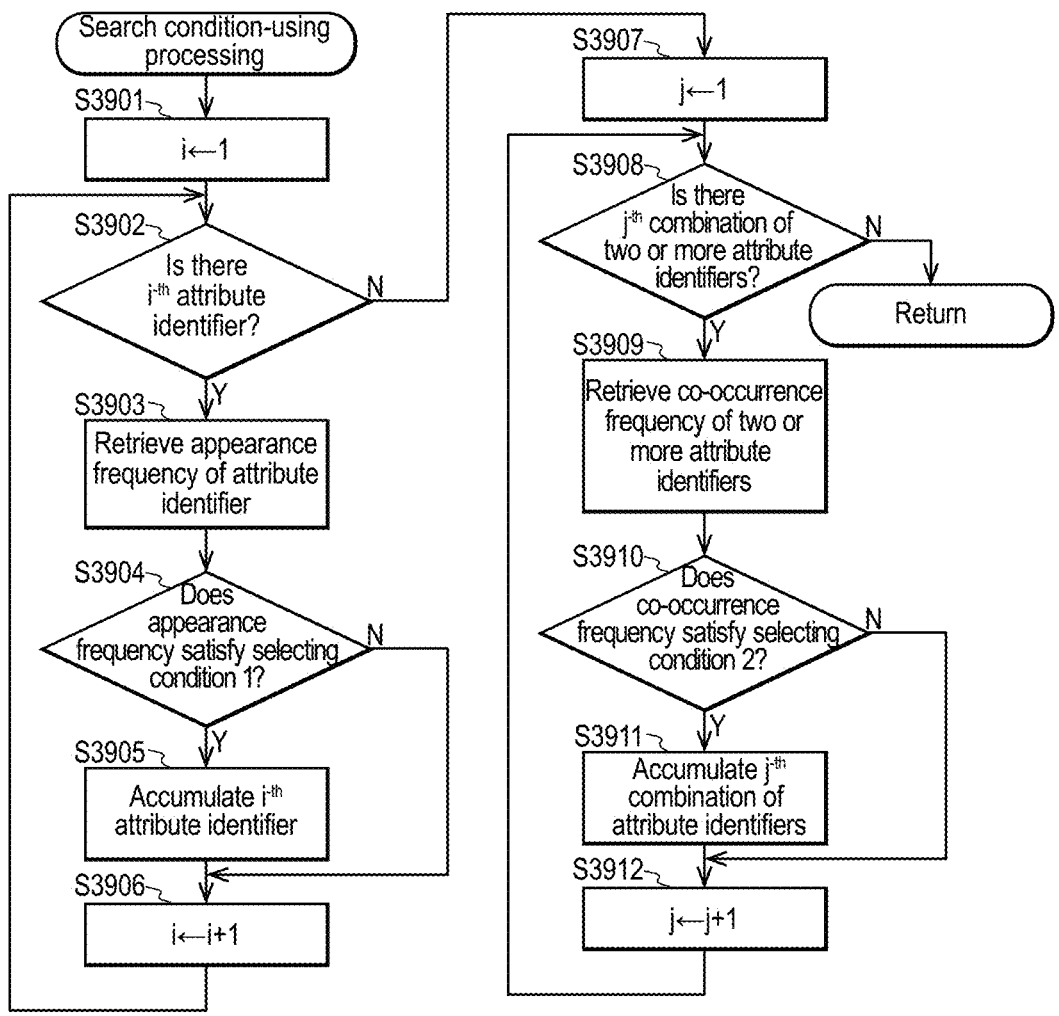
FIG. 39 is a flowchart illustrating of an example of search condition-using processing in the embodiment.

Next, an example of the search condition-using processing in step S3804 will be described with reference to the flowchart in FIG. 39.

(Step S3901) The record index generating unit 5313 substitutes 1 for a counter i.

(Step S3902) The record index generating unit 5313 determines whether or not there is an $i^{-th}$ attribute identifier. If there is an $i^{-th}$ attribute identifier in the one or more attribute identifiers of the data source targeted for search, the procedure advances to step S3903, or otherwise the procedure advances to step S3907. The one or more attribute identifiers of the data source may be key item identifiers.

(Step S3903) The record index generating unit 5313 retrieves an appearance frequency of the $i^{-th}$ attribute identifier of the data source targeted for search, in the search conditions in the storage unit 51. The appearance frequency may be the number of times of appearance or the appearance ratio.

(Step S3904) The record index generating unit 5313 determines whether or not the appearance frequency retrieved in step S3903 satisfies a selecting condition 1. If it satisfies the selecting condition 1, the procedure advances to step S3905, or otherwise the procedure advances to step S3906. The selecting condition 1 is, for example, that the appearance frequency is greater than or equal to a threshold or is greater than the threshold.

The selecting condition 1 may be, for example, that the appearance frequency is within the top N (N is a natural number of 1 or more) in the two or more attribute identifiers, or the like. In the case of this condition, the record index generating unit 5313 retrieves appearance frequencies of all attribute identifiers, and then determines an attribute identifier that is to be accumulated in an unshown buffer.

(Step S3905) The record index generating unit 5313 accumulates the $i^{-th}$ attribute identifier in an unshown buffer. The $i^{-th}$ attribute identifier is a key item group for which a record index is to be configured. This key item group is one attribute identifier.

(Step S3906) The record index generating unit 5313 increments the counter i by 1. The procedure returns to step S3902.

(Step S3907) The record index generating unit 5313 substitutes 1 for a counter j.

(Step S3908) The record index generating unit 5313 determines whether or not there is a $j^{-th}$ combination of two or more attribute identifiers. If there is a $j^{-th}$ combination of two or more attribute identifiers, the procedure advances to step S3909, or otherwise the procedure returns to the upper-level processing.

(Step S3909) The record index generating unit 5313 retrieves a co-occurrence frequency of the $j^{-th}$ combination of two or more attribute identifiers, in the search conditions. The co-occurrence frequency the number of search conditions in which all of the two or more attribute identifiers are included, or the ratio thereof.

(Step S3910) The record index generating unit 5313 determines whether or not the co-occurrence frequency retrieved in step S3909 satisfies a selecting condition 2. If it satisfies the selecting condition 2, the procedure advances to step S3911, or otherwise the procedure advances to step S3912. The selecting condition 2 is, for example, that the co-occurrence frequency is greater than or equal to a threshold or is greater than the threshold.

The selecting condition 2 may be, for example, that the co-occurrence frequency is within the top N (N is a natural number of 1 or more) in the two or more combinations of attribute identifiers, or the like. In the case of this condition, the record index generating unit 5313 retrieves co-occurrence frequencies of all combinations of attribute identifiers, and then determines a combination of attribute identifiers that is to be accumulated in an unshown buffer.

(Step S3911) The record index generating unit 5313 accumulates the $j^{-th}$ combination of two or more attribute identifiers in an unshown buffer. The $j^{-th}$ combination of two or more attribute identifiers is a key item group for which a record index is to be configured. This key item group is constituted by two or more attribute identifiers.

(Step S3912) The record index generating unit 5313 increments the counter j by 1. The procedure returns to step S3908.

Figure 40:
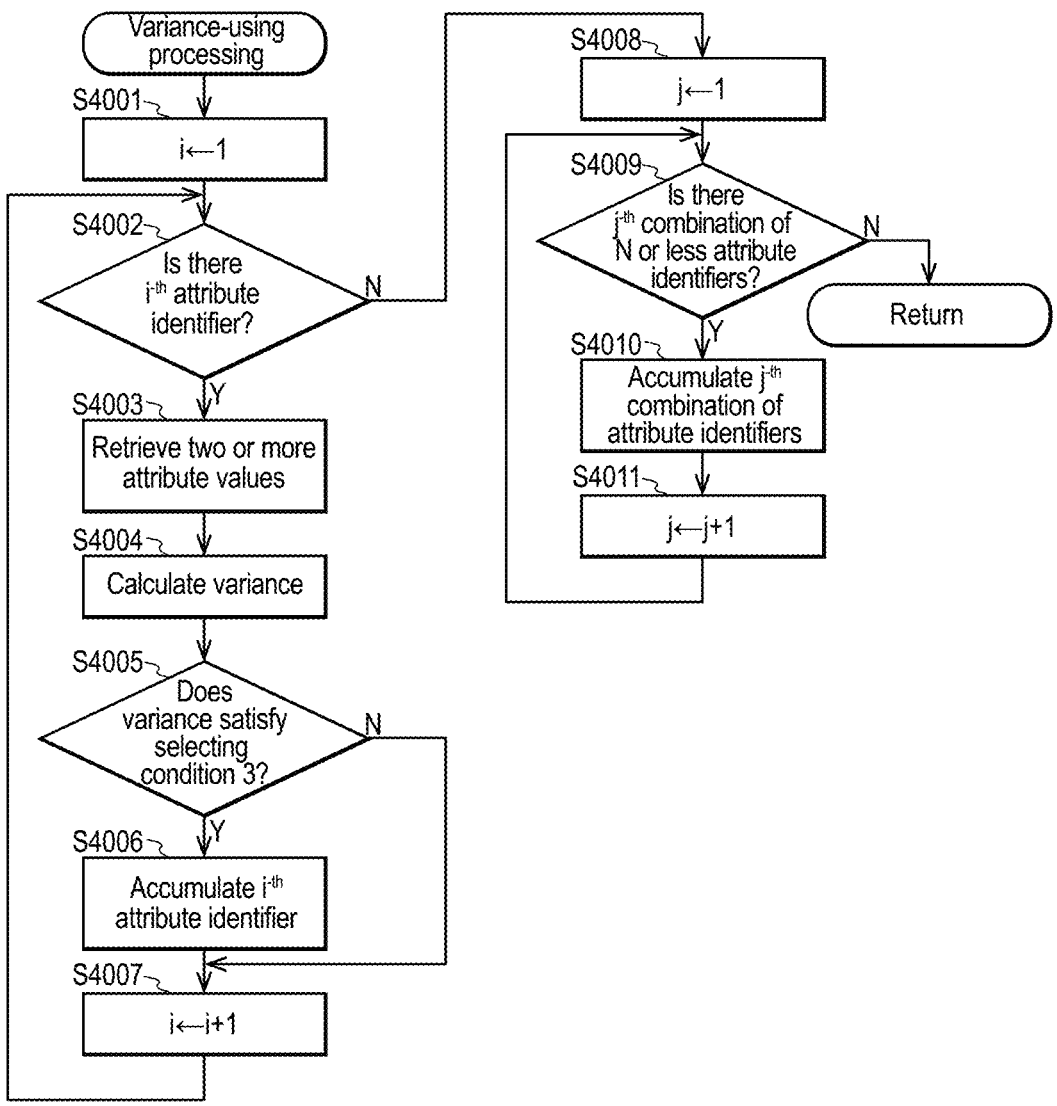
FIG. 40 is a flowchart illustrating of an example of variance-using processing in the embodiment.

Next, an example of the variance-using processing in step S3805 will be described with reference to the flowchart in FIG. 40.

(Step S4001) The record index generating unit 5313 substitutes 1 for a counter i.

(Step S4002) The record index generating unit 5313 determines whether or not there is an $i^{-th}$ attribute identifier. If there is an $i^{-th}$ attribute identifier in the one or more attribute identifiers of the data source targeted for search, the procedure advances to step S4003, or otherwise the procedure advances to step S4008. The one or more attribute identifiers of the data source may be key item identifiers.

(Step S4003) The record index generating unit 5313 retrieves attribute values corresponding to the $i^{-th}$ attribute identifier of the respective records in the data source targeted for search.

(Step S4004) The record index generating unit 5313 calculates a variance of the two or more attribute values retrieved in step S4003.

(Step S4005) The record index generating unit 5313 determines whether or not the variance calculated in step S4004 satisfies a selecting condition 3. If it satisfies the selecting condition 3, the procedure advances to step S4006, or otherwise the procedure advances to step S4007. The selecting condition 3 is, for example, that the variance is greater than or equal to a threshold or is greater than the threshold. The selecting condition 3 may be, for example, that the variance is within the top N (N is a natural number of 1 or more), or the like.

(Step S4006) The record index generating unit 5313 accumulates the $i^{-th}$ attribute identifier in an unshown buffer. The $i^{-th}$ attribute identifier is a key item group for which a record index is to be configured. This key item group is one attribute identifier.

(Step S4007) The record index generating unit 5313 increments the counter i by 1. The procedure returns to step S4002.

(Step S4008) The record index generating unit 5313 substitutes 1 for a counter j.

(Step S4009) The record index generating unit 5313 determines whether or not there is a $j^{-th}$ combination of N or less attribute identifiers (N is a natural number of 2 or more) in the group of the attribute identifiers accumulated in step S4006. If there is a $j^{-th}$ combination of attribute identifiers, the procedure advances to step S4010, or otherwise the procedure returns to the upper-level processing.

(Step S4010) The record index generating unit 5313 accumulates the $j^{-th}$ combination of attribute identifiers in an unshown buffer. The $j^{-th}$ combination of two or more attribute identifiers is a key item group for which a record index is to be configured. This key item group is constituted by two or more attribute identifiers.

(Step S4011) The record index generating unit 5313 increments the counter j by 1. The procedure returns to step S4009.

Figure 41:
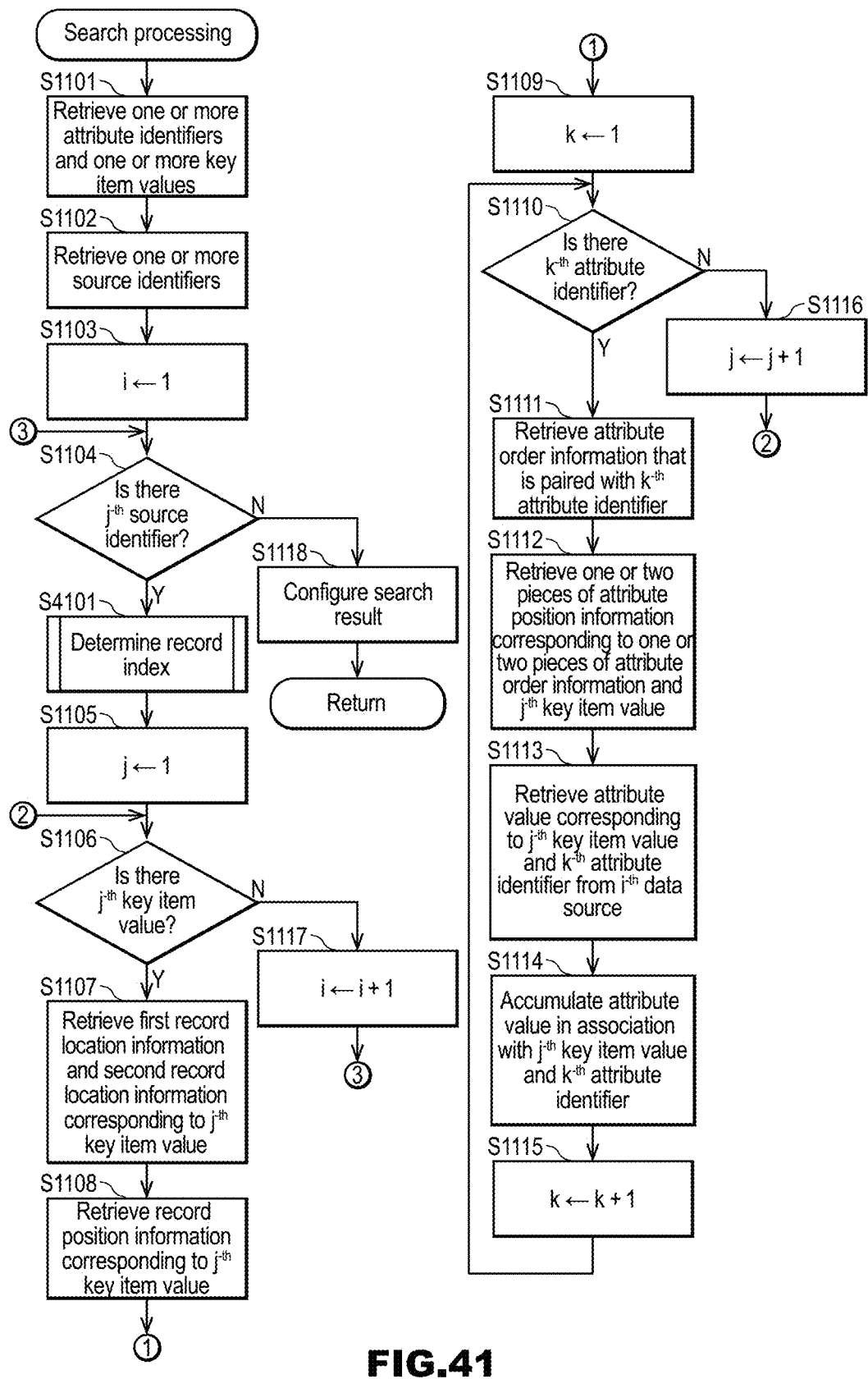
FIG. 41 is a flowchart illustrating of a first example of search processing in the embodiment.

Next, a first example of the search processing in step S3503 will be described with reference to the flowchart in FIG. 41. In the flowchart in FIG. 41, a description of the same steps as those in the flowchart in FIG. 11 has been omitted.

(Step S4101) The record index determining part 5322 determines a record index that is to be used for search.

Below, an example of the processing that determines a record index will be described with reference to the flowchart in FIG. 43.

Figure 43:
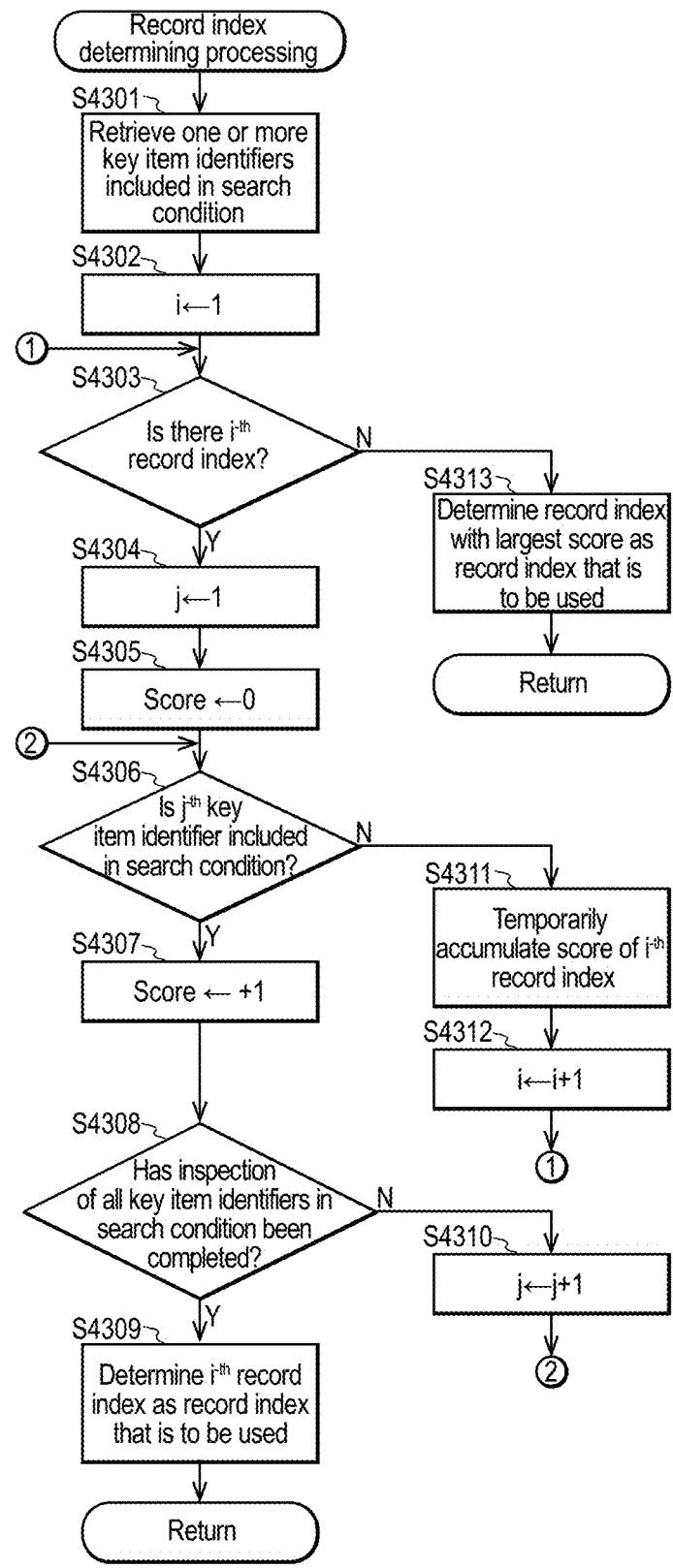
FIG. 43 is a flowchart illustrating of an example of record index determining processing in the embodiment.

In the flowchart in FIG. 43, in step S1108, the search unit 532 retrieves record position information using the record index determined in step S4101.

Figure 42:
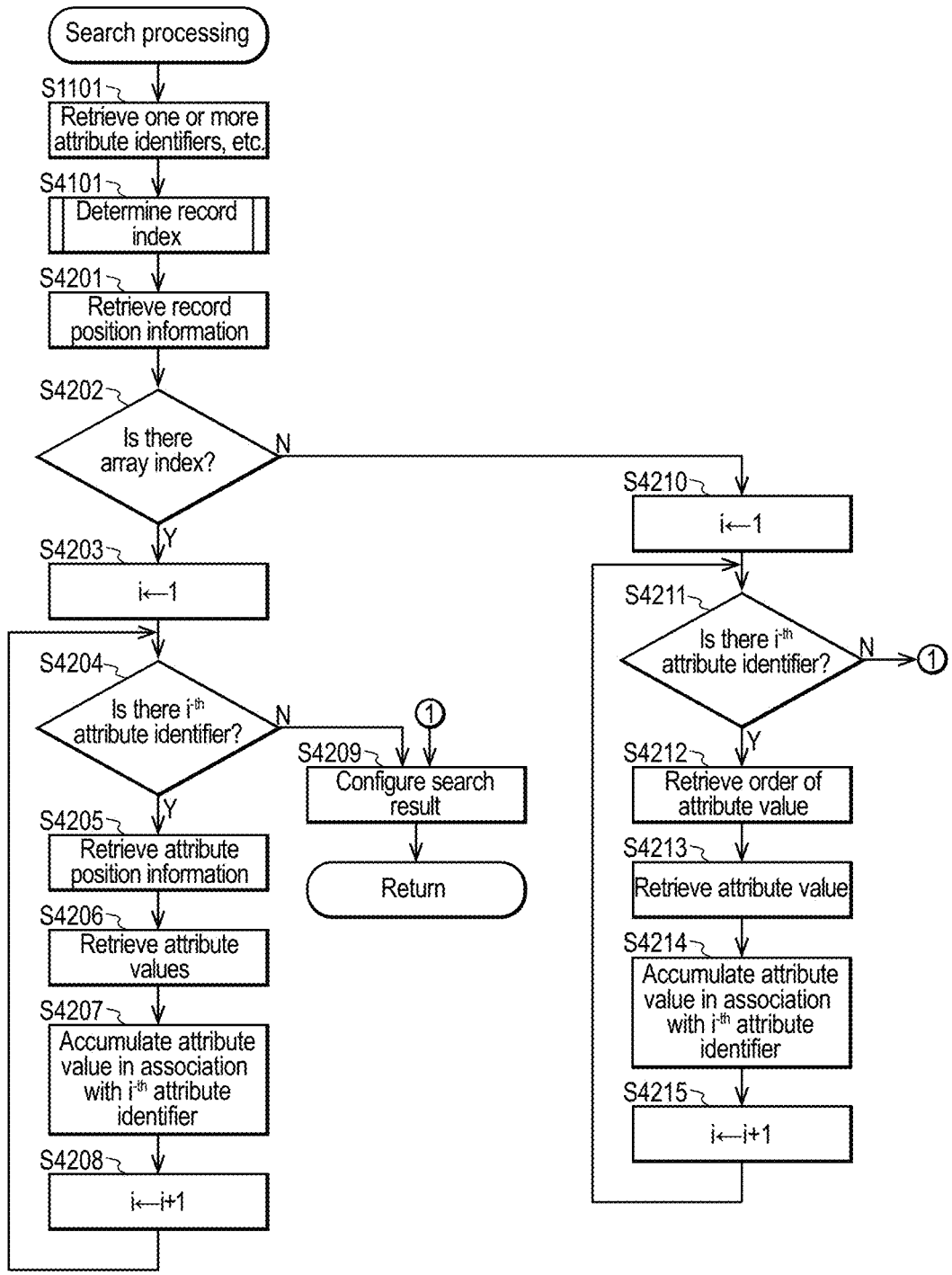
FIG. 42 is a flowchart illustrating of a second example of search processing in the embodiment.

Next, a second example of the search processing in step S3503 will be described with reference to the flowchart in FIG. 42. In the flowchart in FIG. 42, a description of the same steps as those in the flowchart in FIGS. 11 and 41 has been omitted.

(Step S4201) The search part 5323 searches the record index determined in step S4101, determines a record index record corresponding to the key item value included in the search condition, and retrieves record position information included in the record index record.

(Step S4202) The search part 5323 determines whether or not there is an array index corresponding to the data source targeted for search. If there is an array index, the procedure advances to step S4203, or otherwise the procedure advances to step S4210.

(Step S4203) The search part 5323 substitutes 1 for a counter i.

(Step S4204) The search part 5323 determines whether or not there is an $i^{-th}$ attribute identifier included in the search condition (retrieved through search). If there is an $i^{-th}$ attribute identifier, the procedure advances to step S4204, or otherwise the procedure advances to step S4209.

(Step S4205) The search part 5323 retrieves attribute position information corresponding to the $i^{-th}$ attribute identifier from the array index.

(Step S4206) The search part 5323 retrieves an attribute value specified with the attribute position information retrieved in step S4205, in the record specified with the record position information retrieved in step S4201, from the data source.

(Step S4207) The search part 5323 temporarily accumulates the attribute value retrieved in step S4206 in an unshown buffer in association with the $i^{-th}$ attribute identifier.

(Step S4208) The search part 5323 increments the counter i by 1. The procedure returns to step S4204.

(Step S4209) The search part 5323 configures a search result using the attribute value and the like temporarily accumulated in the unshown buffer. The procedure returns to the upper-level processing.

(Step S4210) The search part 5323 substitutes 1 for a counter i.

(Step S4211) The search part 5323 determines whether or not there is an $i^{-th}$ attribute identifier included in the search condition (retrieved through search). If there is an $i^{-th}$ attribute identifier, the procedure advances to step S4212, or otherwise the procedure advances to step S4209.

(Step S4212) The search part 5323 retrieves the order of the attribute of the $i^{-th}$ attribute identifier, in the data source. This order is the order at which the attribute value corresponding to the $i^{-th}$ attribute identifier is stored, and the order of the attribute value in the record. The information on the order may be in the data source or the storage unit 51.

(Step S4213) The search part 5323 retrieves an attribute value at the position indicated by the order retrieved in step S4212, in the record specified with the record position information retrieved in step S4201.

(Step S4214) The search part 5323 temporarily accumulates the attribute value retrieved in step S4213 in an unshown buffer in association with the $i^{-th}$ attribute identifier.

(Step S4215) The search part 5323 increments the counter i by 1. The procedure returns to step S4211.

Next, an example of the processing that determines a record index in step S4101 will be described with reference to the flowchart in FIG. 43.

(Step S4301) The record index determining part 5322 retrieves one or more key item identifiers corresponding to the key item attribute value included in the search condition. The one or more key item identifiers may be included in the search condition.

(Step S4302) The record index determining part 5322 substitutes 1 for a counter i.

(Step S4303) The record index determining part 5322 determines whether or not there is an $i^{-th}$ record index. If there is an $i^{-th}$ record index, the procedure advances to step S4304, or otherwise the procedure advances to step S4313.

(Step S4304) The record index determining part 5322 substitutes 1 for a counter j.

(Step S4305) The record index determining part 5322 substitutes 0 (initial value) for a score for the $i^{-th}$ record index.

(Step S4306) The record index determining part 5322 refers to the schema information of the $i^{-th}$ record index, and determines whether or not a $j^{-th}$ key item identifier contained in the schema information is included in the key item identifiers retrieved in step S4301. If it is included, the procedure advances to step S4307, or otherwise the procedure advances to step S4311.

(Step S4307) The record index determining part 5322 adds 1 to the score for the $i^{-th}$ record index.

(Step S4308) The record index determining part 5322 determines whether or not it was determined that all key item identifiers retrieved in step S4301 are included in the schema information of the $i^{-th}$ record index. If it was determined that all key item identifiers are included, the procedure advances to step S4309, or otherwise the procedure advances to step S4310.

(Step S4309) The record index determining part 5322 determines the $i^{-th}$ record index as a record index that is to be used for search. The procedure returns to the upper-level processing. This determination is, for example, reading the $i^{-th}$ record index, retrieving an identifier of the $i^{-th}$ record index, or the like.

(Step S4310) The record index determining part 5322 increments the counter j by 1. The procedure returns to step S4306.

(Step S4311) The record index determining part 5322 temporarily accumulates the score of the $i^{-th}$ record index in an unshown buffer in association with the $i^{-th}$ record index.

(Step S4312) The record index determining part 5322 increments the counter i by 1. The procedure returns to step S4303.

(Step S4313) The record index determining part 5322 refers to the unshown buffer, and determines a record index corresponding to the largest score, as a record index that is to be used for search. The procedure returns to the upper-level processing.

Hereinafter, a specific operation example of the search system B in this embodiment will be described.

It is assumed that one data source (X) shown in FIG. 44 is stored in the data source storage unit 111 of the data source management apparatus 2. The structure of the data source in FIG. 44 is substantially similar to the structure of the data source in FIG. 12, except that "Region" is included in the label record.

The label record in this example is the first row of a file. The label record is a group of attribute identifiers. Some attribute identifiers of the group of attribute identifiers may be key item identifiers. In FIG. 44, [No.] is a record ID, and has a value of [1], [2], [3], or the like in FIG. 44. Note that (Pos.) below [No.] is record position information of each record (an offset of the beginning of the record in the data source, in this example). "PID" is a user identifier. "Age" is the age of a user. "Region" is a region in which a user lives (a prefecture, in this example).

In this situation, the following two specific examples will be described. Specific Example 1 is an example of the processing that generates two or more record indexes. Specific Example 2 is an example of the processing that selects one record index out of two or more record indexes and performs search using the record index.

Specific Example 1

It is assumed that an administrator of the search apparatus 5 inputs an index generating instruction to the terminal apparatus 3. This index generating instruction contains information for specifying the data source (X) and information for specifying a group of one or more key items. Specifically, the index generating instruction contains "<data source>X <key item group> (Age, PID) <key item group> (Region, Age) <key item group> (PID)".

Next, the terminal apparatus 3 accepts the index generating instruction and transmits the index generating instruction to the search apparatus 5.

Next, the accepting unit 12 of the search apparatus 5 receives the index generating instruction from the terminal apparatus 3. Next, the index generating unit 131 generates a record index of the data source (X) as follows.

That is to say, the record index generating unit 5313 retrieves a key item group "<key item group> (Age, PID) <key item group> (Region, Age) <key item group> (PID)" contained in the index generating instruction.

Next, the record index generating unit 5313 accesses the data source management apparatus 2 in which the data source (X) is stored using "<data source>X" and "<key item group> (Age, PID)", and reads the data source (X). Next, the record index generating unit 5313 retrieves, for each record of the data source (X), a record index record including an attribute value of "Age", an attribute value "PID", and record position information of the record of the data source (X). Next, the record index generating unit 5313 sorts the record index records using the two attribute values "Age" and "PID" as a key, and configures a record index that is to be accumulated. Then, the record index generating unit 5313 accumulates the record index in the record index storage unit 5113.

In this record index, sorting is performed in the ascending order or the descending order using the two attribute values consisting of a first key "Age" and a second key "PID" as a key. The record index generating unit 5313 accumulates the schema information (Age, PID) of the record index in the record index storage unit 5113 in association with the record index. In this example, the schema information contains one or more attribute identifiers. In the case in which schema information has two or more attribute identifiers, the two or more attribute identifiers are ordered. The accumulated record index is taken as a record index (1) (see FIG. 45).

Next, the record index generating unit 5313 accesses the data source management apparatus 2 in which the data source (X) is stored using "<data source>X" and "<key item group> (Region, Age)", and retrieves, for each record of the data source (X), a record index record including an attribute value of "Region", an attribute value "Age", and record position information of the record of the data source (X). Next, the record index generating unit 5313 sorts the record index records using the two attribute values "Region" and "Age" as a key, and configures a record index that is to be accumulated. Then, the record index generating unit 5313 accumulates the record index in the record index storage unit 5113.

In this record index, sorting is performed in the ascending order or the descending order using the two attribute values consisting of a first key "Region" and a second key "Age" as a key. The record index generating unit 5313 accumulates the schema information (Region, Age) of the record index in the record index storage unit 5113 in association with the record index. The accumulated record index is taken as a record index (2) (see FIG. 45).

Next, the record index generating unit 5313 accesses the data source management apparatus 2 in which the data source (X) is stored using "<data source>X" and "<key item group> (PID)", and retrieves, for each record of the data source (X), a record index record including an attribute value of "PID" and record position information of the record of the data source (X). Next, the record index generating unit 5313 sorts the record index records using the attribute "PID" as a key, and configures a record index that is to be accumulated. Then, the record index generating unit 5313 accumulates the record index in the record index storage unit 5113.

Furthermore, the record index generating unit 5313 accumulates the schema information (PID) of the record index in association with the record index in the record index storage unit 5113. The accumulated record index is taken as a record index (3) (see FIG. 45).

Figure 45:
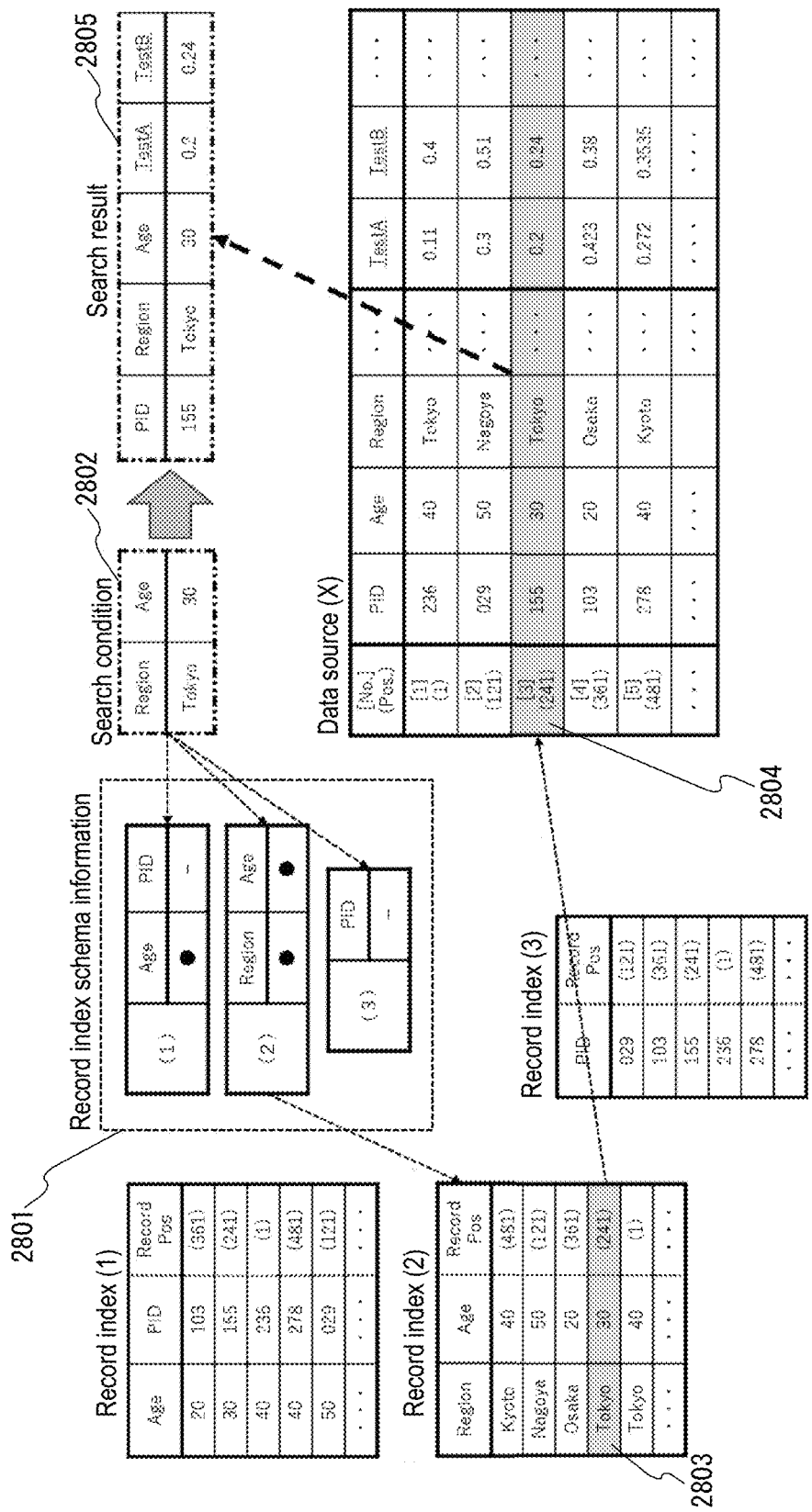
FIG. 45 is a diagram illustrating an example of search processing in the embodiment.

Through the above-described processing, the record indexes (1), (2), and (3), and the record index schema information 2801 in FIG. 45 are accumulated in the record index storage unit 5113.

Specific Example 2

It is assumed that a user of the search apparatus 5 inputs a search condition "Select PID, Region, Age, Test A, Test B where Region=Tokyo AND Age=30 from the data source (X)" to the terminal apparatus 3. Information indicating a where phrase in the search condition is denoted by 2802 in FIG. 45.

Then, the terminal apparatus 3 accepts the search condition and transmits the search condition to the search apparatus 5.

Next, the condition accepting unit 121 of the search apparatus 5 receives the search condition from the terminal apparatus 3.

Next, the record index determining part 5322 inspects the schema information (2801 in FIG. 45) of the record indexes using "Region=Tokyo AND Age=30" included in the search condition, and determines a record index (2) including both attribute identifiers "Region" and "Age", as a record index that is to be used for search.

Next, the search part 5323 searches the record index (2) for a record index record 2803 corresponding to the where phrase "Region=Tokyo AND Age=30". Then, the search part 5323 retrieves record position information (Record Pos) "241" included in the record 2803 from the record index (2).

Next, the search part 5323 reads the data source (X), and moves the file pointer to the position of the record (see 2804 in FIG. 45) corresponding to the record position information "241". Next, the search part 5323 retrieves an attribute identifier "PID, Region, Age, Test A, Test B" targeted for search included in the search condition, from the record 2804. Next, the search part 5323 refers to the schema information (not shown) of the data source (X), and retrieves the order "1" of the attribute identifier "PID", the order "3" of the attribute identifier "Region", the order "2" of the attribute identifier "Age", the order "Y (Y is a natural number of 4 or more)" of the attribute identifier "Test A", and the order "Y+1" of the attribute identifier "Test B". Then, the search part 5323 sequentially scans the attribute values of the record specified with the record position information "241", retrieves attribute values indicated by the orders for the respective attribute identifiers, and accumulates the attribute values in association with the attribute identifiers. Then, the search part 5323 acquires a search result "<PID>155 <Region>Tokyo <Age>30 <Test A>0.2 <Test B>0.24".

Next, the result output unit 141 transmits the retrieved search result to the terminal apparatus 3 of the user.

Next, the terminal apparatus 3 receives and outputs the search result. An output example of this search result is denoted by 2805 in FIG. 45.

As described above, according to this embodiment, it is possible to search for information at high speed for a wide variety of search conditions, by searching a data source for information using two or more record indexes.

Furthermore, according to this embodiment, it is possible to generate two or more proper record indexes.

The processing in this embodiment may be realized by software. The software may be distributed by software downloads or the like. Furthermore, the software may be distributed in a form where the software is stored in a storage medium such as a CD-ROM. The same applies to other embodiments in this specification. The software that realizes the search apparatus 5 in this embodiment is the following sort of program. Specifically, this program is a program for causing a computer capable of accessing a record index storage unit in which two or more record indexes respectively corresponding to combinations of different key items are stored, the record indexes being indexes corresponding to records of a data source including two or more records having key item values respectively corresponding to two or more key items and attribute values respectively corresponding to one or more attribute identifiers, and being two or more record indexes constituting a group of combinations of one or more key item values corresponding to a combination of one or more key items and record position information for specifying a position of a record including the one or more key item values, to function as: a condition accepting unit that accepts a search condition having a key item value; a search unit that selects one record index corresponding to a combination of one or more key items including a key item corresponding to the key item value included in the search condition, out of the two or more record indexes, retrieves record position information that is paired with the key item value included in the search condition, from the selected record index, and retrieves an attribute value in a record corresponding to a position specified with the record position information, from the data source; and a result output unit that outputs a search result including the attribute value retrieved by the search unit.

Figure 46:
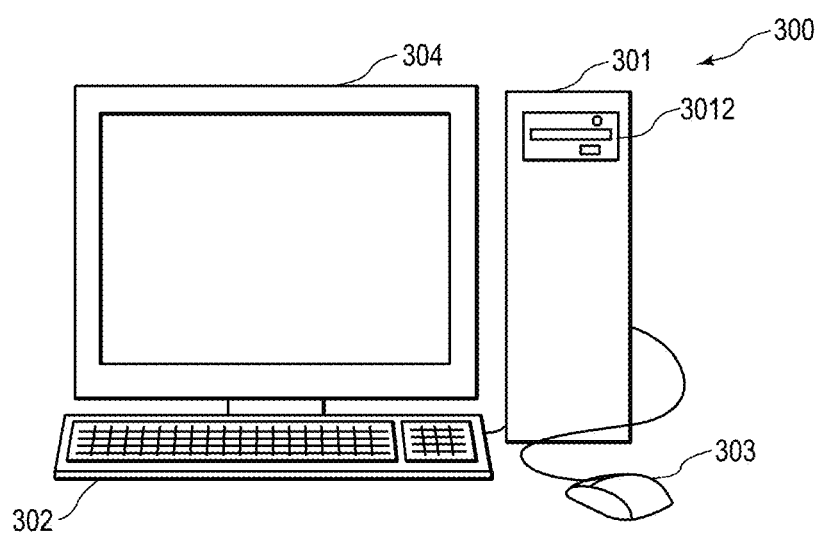
FIG. 46 is a schematic view of a computer system in the foregoing embodiments.
Figure 47:
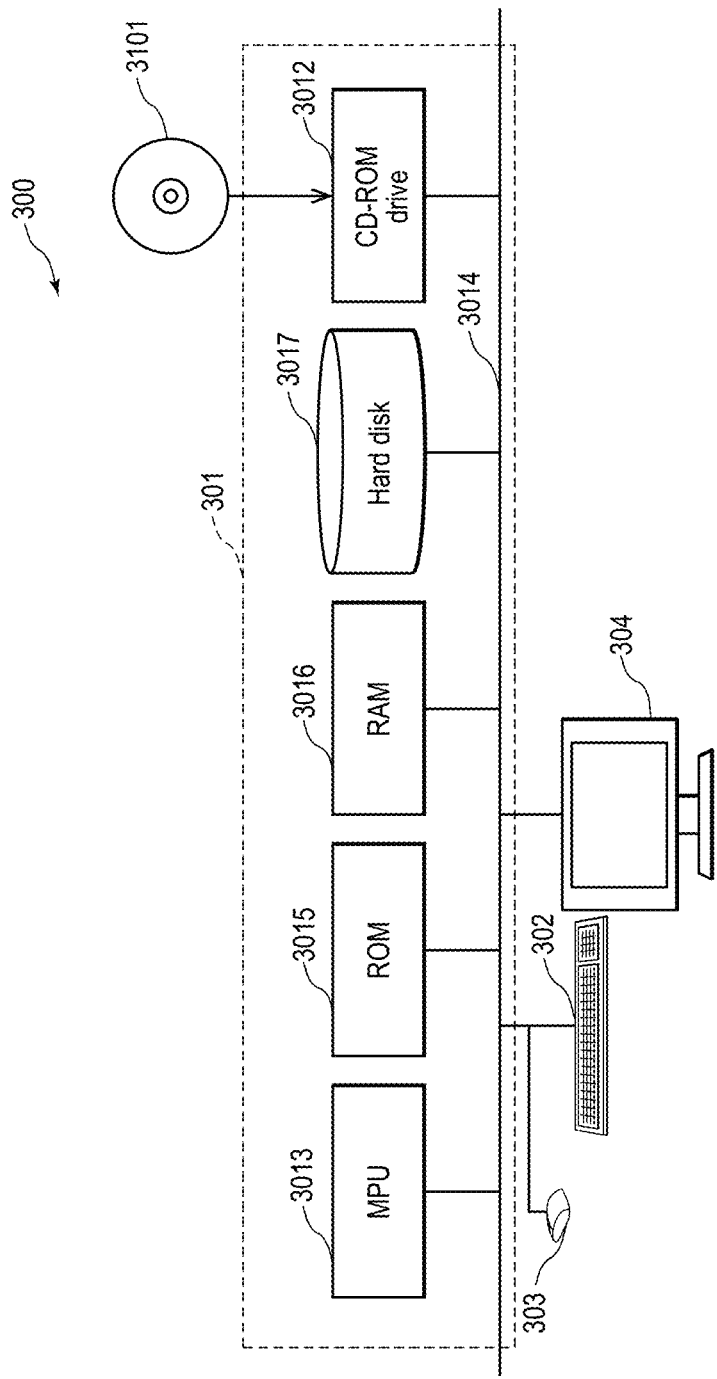
FIG. 47 is a block diagram of the computer system in the embodiments.

FIG. 46 shows the external appearance of a computer that executes the program described in this specification to realize the search apparatus 1 and the like in the foregoing various embodiments. The foregoing embodiments may be realized using computer hardware and a computer program executed thereon. FIG. 46 is a schematic view of a computer system 300. FIG. 47 is a block diagram of the system 300.

In FIG. 46, the computer system 300 includes a computer 301 including a CD-ROM drive, a keyboard 302, a mouse 303, and a monitor 304.

In FIG. 47, the computer 301 includes, in addition to the CD-ROM drive 3012, an MPU 3013, a bus 3014 connected to the CD-ROM drive 3012 and the like, a ROM 3015 in which a program such as a boot up program is stored, a RAM 3016 that is connected to the MPU 3013 and is a memory in which a command of an application program is temporarily stored and a temporary storage area is provided, and a hard disk 3017 in which an application program, a system program, and data are stored. Although not shown, the computer 301 may further include a network card that provides connection to a LAN.

The program for causing the computer system 300 to execute the functions of the search apparatus 1 and the like in the foregoing embodiments may be stored in a CD-ROM 3101 that is inserted into the CD-ROM drive 3012, and be transmitted to the hard disk 3017. Alternatively, the program may be transmitted via a network (not shown) to the computer 301 and stored in the hard disk 3017. At the time of execution, the program is loaded into the RAM 3016. The program may be loaded from the CD-ROM 3101, or directly from a network.

The program does not necessarily have to include, for example, an operating system (OS) or a third party program to cause the computer 301 to execute the functions of the search apparatus 1 and the like in the foregoing embodiments. The program may only include a command portion to call an appropriate function (module) in a controlled mode and obtain desired results. The manner in which the computer system 300 operates is well known, and thus a detailed description thereof has been omitted.

It should be noted that, in the program, in a step of transmitting information, a step of receiving information, or the like, processing that is performed by hardware, for example, processing performed by a modem or an interface card in the transmitting step (processing that can be performed only by hardware) is not included.

Furthermore, the computer that executes the program may be a single computer, or may be multiple computers. That is to say, centralized processing may be performed, or distributed processing may be performed.

Furthermore, in the foregoing embodiments, it will be appreciated that at least two communication parts in one apparatus may be physically realized by one medium.

In the foregoing embodiments, each process may be realized as centralized processing using a single apparatus, or may be realized as distributed processing using multiple apparatuses.

The present invention is not limited to the embodiment set forth herein. Various modifications are possible within the scope of the present invention.

INDUSTRIAL APPLICABILITY

As described above, the search apparatus according to the present invention has an effect that it is possible to search for information at high speed, and thus this apparatus is useful as a search apparatus and the like.

The invention claimed is:

1. A search apparatus for searching a plurality of data sources in which attribute values are stored with respect to a plurality of records and a plurality of attribute identifiers, the plurality of data sources each associated with a source identifier for identifying a data source, the plurality of data sources being stored in a data source storage unit, the search apparatus comprising:
   an array index storage unit in which an array index having attribute position information indicating a range of a position in the data source at which an attribute value is located is stored for each of one or more records out of a plurality of records and for each of a plurality of attributes of each record of the data source;
   an array label index storage unit in which an array label index having attribute order information for specifying an order of the attribute identifiers in the data source in which attribute position information of an attribute value is located is stored for each of the plurality of attributes and for each of the plurality of data sources;
   a source index storage unit in which a source index having the source identifier, a smallest key item value included in a data source identified with the source identifier, and a largest key item value included in the data source identified with the source identifier is stored for each of the plurality of data sources; and
   a processor that:
      accepts a search condition including an attribute identifier and a key item value;
      retrieve a source identifier that matches the key item value included in the search condition or that is paired with the smallest key item value and the largest key item value between which the key item value is located, from the source index,
      by referring to an array label index corresponding to the retrieved source identifier, retrieves attribute order information corresponding to the attribute identifier included in the search condition, from the array label indexes corresponding to the retrieved source identifier,
      retrieves attribute position information corresponding to the attribute identifier included in the search condition, from the array index, using the attribute order information,
      retrieves an attribute value corresponding to the attribute identifier included in the search condition, using the attribute position information, from the data source storage unit; and
      outputs a search result including the attribute value retrieved.

2. The search apparatus according to claim 1, wherein:
   the array index comprises first attribute position information corresponding to an attribute identifier for identifying an attribute value located before an attribute value identified with the attribute identifier included in the search condition and second attribute position information corresponding to an attribute identifier for identifying an attribute value located after the attribute value identified with the attribute identifier included in the search condition, and
   the processor
      retrieves the first attribute position information and the second attribute position information, by using the attribute identifier included in the search condition, and
      retrieves the attribute value by using the first attribute position information and the second attribute position information, from the data source.

3. The search apparatus according to claim 1, further comprising:
   a record index storage unit in which a plurality of record indexes are stored, wherein:

each of the plurality of record indexes is an index corresponding to a record of the data source and is a combination of the key item value and record position information for specifying a position of the record including the key item value, each of the plurality of records of the data source includes the key item value and the attribute values, the processor:
retrieves record position information that is paired with the key item value included in the search condition, from the record indexes,
determines a record corresponding to a position specified with the record position information, and
retrieves the attribute value included in the record and corresponding to the attribute identifier included in the search condition, from the data source.

4. The search apparatus according to claim 3, further comprising:
a secondary index storage unit in which a secondary index is stored, wherein:
the secondary index comprises a plurality of key item values each paired with record index record position information for specifying a portion that is included in the plurality of record indexes and at which record position information is located,
the processor:
retrieves first record index record position information and second record index record position information corresponding to the key item value included in the search condition, from the secondary index,
determines record index record position information between the first record index record position information and the second record index record position information, from the plurality of record indexes,
retrieves record position information that is paired with the record index record position information, from the plurality of record indexes,
determines a record corresponding to a position specified with the record position information, and
retrieves the attribute value included in the record and corresponding to the attribute identifier included in the search condition, from the data source.

5. The search apparatus according to claim 1, wherein:
the processor:
generates the array label index having the attribute order information, and accumulates the array label index in the array label index storage unit;
refers to the plurality of data sources, generates a record index, which is a combination of the key item value and record position information of each of a plurality of records of the plurality of data sources, and accumulates the record index in the record index storage unit;
retrieves a combination of record index record position information for specifying a portion at which record position information is located and the key item value of the record, for each of one or more records constituting part of the plurality of records, generates a secondary index, and accumulates the secondary index in a secondary index storage unit, and
retrieves the source identifier, the smallest key item value included in the data source identified with the source identifier, and the largest key item value included in the data source identified with the source identifier, for each of the plurality of data sources, generates the source index having the source identifier, the smallest key item value, and the largest key item value, and accumulates the source index in the source index storage unit.

6. The search apparatus according to claim 1,
wherein last updated time information for specifying a last updated time is associated with the data source,
generated time information for specifying a time at which an array index is generated is associated with the array index, and
the processor, in a case in which a predetermined condition is satisfied, determines whether or not the last updated time indicated by the last updated time information is after the generated time indicated by the generated time information, and, in a case in which the last updated time is after the generated time, operates to configure the array index.

7. The search apparatus according to claim 1,
wherein the search apparatus searches for information referring to a data dictionary having:
source layer defining information, which is information defining each of a plurality of data sources each including one or more records having one or more attribute values, and is information having a source identifier, which is an identifier of a data source, and one or more pieces of source attribute defining information each containing a source attribute identifier, which is an attribute identifier of a data source among the plurality of data sources;
user layer defining information, which is information defining a user table that is to be searched based on a search condition and that includes one or more records having one or more attribute values, and is information having a user table identifier for identifying the user table and one or more pieces of user attribute defining information each containing a user attribute identifier, which is an attribute identifier of the user table; and
conversion rule defining information, which is information for generating a search command that is to be issued to each of the plurality of data sources, based on the search condition, retrieving search results corresponding to the search command, and generating integrated data corresponding to the search condition using two or more search results,
the processor accepts a search condition for the user table,
the processor determines two or more data sources corresponding to the search condition referring to the data dictionary, generates a search command for each of the plurality of data sources, using the conversion rule defining information, retrieves search results based on the search command, and integrates the search results respectively corresponding to the plurality of data sources using the conversion rule defining information and the user layer defining information, thereby retrieving integrated data corresponding to the search condition, and
the processor outputs the integrated data retrieved.

8. The search apparatus according to claim 1, further comprising:
a record index storage unit in which a plurality of record indexes respectively corresponding to combinations of different key items are stored, the plurality of record indexes being indexes corresponding to records of a data source including a plurality of records having key item values respectively corresponding to a plurality of key items and attribute values respectively corresponding to one or more attribute identifiers, and being plurality of record indexes constituting a group of combinations of one or more key item values corresponding to a combination of one or more key items and record position information for specifying a position of a record including the one or more key item values, wherein the processor accepts a search condition having a key item value, the processor selects one record index corresponding to a combination of one or more key items including a key item corresponding to the key item value included in the search condition, out of the plurality of record indexes, retrieves record position information that is paired with the key item value included in the search condition, from the selected record index, and retrieves an attribute value in a record corresponding to a position specified with the record position information, from the data source, and the processor outputs a search result including the attribute value retrieved.

9. A search method for searching a plurality of data sources in which attribute values are stored with respect to a plurality of records and a plurality of attribute identifiers, the plurality of data sources each associated with a source identifier for identifying a data source, the plurality of data sources being stored in a data source storage unit, by accessing an array index storage unit in which an array index having attribute position information indicating a range of a position in the data source at which an attribute value is located is stored for each of one or more records out of a plurality of records and for each of a plurality of attributes of each record of the data source; an array label index storage unit in which an array label index having attribute order information for specifying an order of the attribute identifiers in the data source in which attribute position information of an attribute value is located is stored for each of the plurality of attributes and for each of the plurality of data sources; and a source index storage unit in which a source index having the source identifier, a smallest key item value included in a data source identified with the source identifier, and a largest key item value included in the data source identified with the source identifier is stored for each of the plurality of data sources, the method comprising:

accepting, by a processor, a search condition including an attribute identifier and a key item value;

retrieving a source identifier that matches the key item value included in the search condition or that is paired with the smallest key item value and the largest key item value between which the key item value is located, from the source index;

by referring to an array label index corresponding to the retrieved source identifier, retrieving, by the processor, attribute order information corresponding to the attribute identifier included in the search condition, from the array label indexes corresponding to the retrieved source identifier;

retrieving, by the processor, attribute position information corresponding to the attribute identifier included in the search condition, from the array index, using the attribute order information;

retrieving, by the processor, an attribute value corresponding to the attribute identifier included in the search condition, from the data source, using the attribute position information; and outputting, by the processor, a search result including the attribute value.

10. The search apparatus according to claim 1, further comprising:

an array index generating unit that retrieves attribute position information for specifying a position at which each of one or more attribute values is located, for each of one or more records out of two or more records in the data sources and for each attribute, generates the array index having the attribute position information, and accumulates the array index in the array index storage unit.

11. A non-transitory computer readable storage medium storing a program for searching a plurality of data sources in which attribute values are stored with respect to a plurality of records and a plurality of attribute identifiers, the plurality of data sources each associated with a source identifier for identifying a data source, the plurality of data sources being stored in a data source storage unit, by accessing an array index storage unit in which an array index having attribute position information indicating a range of a position in the data source at which an attribute value is located is stored for each of one or more records out of a plurality of records and for each of a plurality of attributes of each record of the data source; an array label index storage unit in which an array label index having attribute order information for specifying an order of the attribute identifiers in the data source in which attribute position information of an attribute value is located is stored for each of the plurality of attributes and for each of the plurality of data sources; and a source index storage unit in which a source index having the source identifier, a smallest key item value included in a data source identified with the source identifier, and a largest key item value included in the data source identified with the source identifier is stored for each of the plurality of data source, wherein the program, when executed by a processor, causes the processor to perform:

accepting a search condition including an attribute identifier and a key item value;

retrieving a source identifier that matches the key item value included in the search condition or that is paired with the smallest key item value and the largest key item value between which the key item value is located, from the source index;

by referring to an array label index corresponding to the retrieved source identifier, retrieving attribute order information corresponding to the attribute identifier included in the search condition, from the array label indexes corresponding to the retrieved source identifier;

retrieving attribute position information corresponding to the attribute identifier included in the search condition, from the array index, using the attribute order information;

retrieving an attribute value corresponding to the attribute identifier included in the search condition, from the data source, using the attribute position information; and outputting a search result including the attribute value.

* * * * *